United States Patent
El-Deiry et al.

(10) Patent No.: US 10,654,801 B2
(45) Date of Patent: May 19, 2020

(54) PRODIGIOSIN ANALOGS

(71) Applicant: Institute For Cancer Research, Philadelphia, PA (US)

(72) Inventors: Wafik S. El-Deiry, Philadelphia, PA (US); Xiaobing Tian, Philadelphia, PA (US); Shengliang Zhang, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 16/091,701

(22) PCT Filed: Apr. 10, 2017

(86) PCT No.: PCT/US2017/026748
§ 371 (c)(1),
(2) Date: Oct. 5, 2018

(87) PCT Pub. No.: WO2017/177216
PCT Pub. Date: Oct. 12, 2017

(65) Prior Publication Data
US 2019/0119207 A1    Apr. 25, 2019

Related U.S. Application Data

(60) Provisional application No. 62/319,882, filed on Apr. 8, 2016.

(51) Int. Cl.
*C07D 207/36* (2006.01)
*A61P 35/00* (2006.01)
*A61K 31/4025* (2006.01)
*C07D 403/14* (2006.01)

(52) U.S. Cl.
CPC ........ *C07D 207/36* (2013.01); *A61K 31/4025* (2013.01); *A61P 35/00* (2018.01); *C07D 403/14* (2013.01)

(58) Field of Classification Search
None
See application file for complete search history.

(56) References Cited

U.S. PATENT DOCUMENTS

| | | |
|---|---|---|
| 6,291,509 B1 | 9/2001 | Ferrari et al. |
| 6,638,968 B1 | 10/2003 | Kim et al. |
| 2005/0267073 A1 | 12/2005 | Dairi et al. |
| 2008/0076739 A1 | 3/2008 | Viallet et al. |
| 2008/0318902 A1 | 12/2008 | Attardo et al. |

OTHER PUBLICATIONS

Valverde et al, J. Org. Chem. 2012, 77, 6538-6544.*
Hong et al., "Prodigiosin rescues deficient p53 signaling and anti-tumor effects via up-regulating p73 and disrupting its interaction with mutant p53", Cancer Res, 2014, 74(4), pp. 1153-1165.
Prabhu et al., "Small-molecule Prodigiosin Restores p53 Tumor Suppressor Activity in Chemoresistant Colorectal Cancer Stem Cells via c-Jun-Mediated delta Np73 Inhibition and p73 Activation", Caner Res, 2016, 76(7), pp. 1989-1999.

* cited by examiner

*Primary Examiner* — Kamal A Saeed
(74) *Attorney, Agent, or Firm* — Stradley Ronon Stevens & Young, LLP

(57) ABSTRACT

Prodigiosin analogs which reactivate the p53 pathway are provided, as well as compositions of these compounds, and methods for reactivation of the p53 pathway using these compounds are provided. The prodigiosin analogs may be used to treat cancer in which p53 mutation plays a role, including prostate cancer, breast cancer, kidney cancer, ovarian cancer, lymphoma, leukemia, and glioblastoma, among others.

8 Claims, 50 Drawing Sheets
Specification includes a Sequence Listing.

SW480

HCT116

| cell lines | IC 50 (μM) of the analogs | | | | | |
|---|---|---|---|---|---|---|
| | HCT116 | HCT116-P53null | SW480 | DLD-1 | Wi38 | MRC5 |
| P01 | 0.05599 | 0.05196 | 0.03877 | 0.04108 | 0.09716 | 0.2338 |
| P301 | 0.1966 | 0.2606 | 0.1598 | 0.2192 | 0.3524 | 0.6382 |
| P303 | 0.4628 | 0.7936 | 0.2877 | | | |

|  | HT29 | MB468 | SW480 | DLD1 | HCT116 p53-null |
|---|---|---|---|---|---|
| IC50(nM) | 66.26 | 97.6 | 95.28 | 53.98 | 41.14 |

|  | FaDu | CAL-27 | PANC-1 | ASPC-1 | U251 | H1975 | MB-231 | MRC5 |
|---|---|---|---|---|---|---|---|---|
| IC50(nM) | 66.02 | 33.88 | 135.5 | 39.19 | 100.2 | 190.4 | 242.3 | 172.6 |

P2A

5'-GCCGCTCGTACTGTGCGTTG-3'

HT29-P2A

Decomposition window

HT29-P2A

Indel Spectrum

1H NMR spectrum of compound 4 (PG3-Oc)

PRODIGIOSIN ANALOGS

REFERENCE TO GOVERNMENT GRANTS

This invention was made with government support under Grant No. CA176289 awarded by the National Institutes of Health. The government has certain rights in the invention.

FIELD

The present disclosure relates generally to the field of formulation chemistry. More particularly, the present disclosure relates to compounds, compositions, and methods for treating cancer, specifically by restoring of the p53 pathway and inducing the expression of the p73 protein.

BACKGROUND

Various publications, including patents, published applications, technical articles and scholarly articles are cited throughout the specification. Each of these cited publications is incorporated by reference herein, in its entirety and for all purposes.

Prodigiosin (represented by tautomeric Formulas (A1) and (A2)) is the parent member of the tripyrrole alkaloid family of natural products that shows potent anti-cancer activity against tumors with mutated p53 proteins.

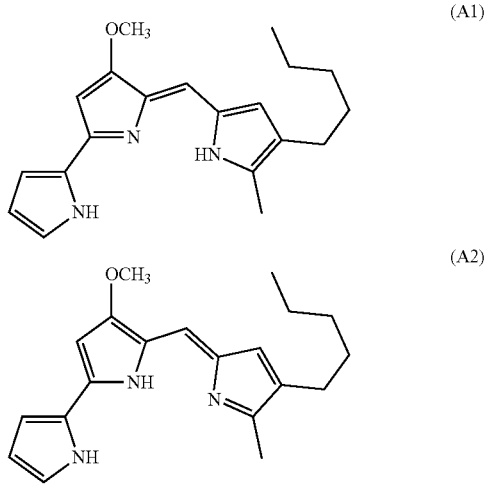

Activation of p53 can induce cell-cycle arrest and apoptosis through transcriptional regulation of specific target genes. However, p53 is mutated in in more than 50% of humor tumors, making functional reactivation of the p53 pathway an attractive strategy for cancer therapy development. Prodigiosin is able is further able to induce the expression of the p73 protein and disrupt its interaction with mutant p53, thereby rescuing p53 pathway deficiency and promoting anti-tumor effects. Accordingly, it is desirable to identify and synthesize prodigiosin analogs that are suitable as cancer treatments through restoration of the p53 pathway and inducing the expression of the p73 protein.

SUMMARY

The present disclosure provides prodigiosin analogs that are believed to reactivate the p53 pathway in mutated cancer cells. Compositions of such prodigiosin analogs are also provided, which compositions comprise the inhibitor and a carrier such as a pharmaceutically acceptable carrier, with the inhibitor can be in an amount effective to reactivate the p53 pathway, such as in a cancer cell in which p53 mutation plays a role. The prodigiosin analog may have the formula of any of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa) disclosed below.

The disclosure also provides methods for reactivation of the p53 pathway, comprising contacting a cell with mutated p53 with an amount of a compound according to any of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof.

In accordance with the methods, the compound may be present in a composition comprising a carrier. The method may be carried out in vivo, in vitro, in situ, or ex vivo. The methods may be carried out using a cell, for example, by contacting a cell with the compound, or pharmaceutically acceptable salt thereof, or composition thereof. The cell may be a cancer cell. The cancer cell may be a prostate cancer cell, a breast cancer cell, a kidney cancer cell, an ovarian cancer cell, a lymphoma cell, a melanoma cell, a leukemia cell, or a glioblastoma cell.

Cancer treatment methods are also provided. The methods may comprise administering to a cancer patient in need thereof a treatment-effective amount of a compound according to any of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof. The cancer patient may be a prostate cancer patient and the cancer may comprise prostate cancer, the cancer patient may be a breast cancer patient and the cancer may comprise breast cancer, the cancer patient may be a kidney cancer patient and the cancer may comprise kidney cancer, the cancer patient may be an ovarian cancer patient and the cancer may comprise ovarian cancer, the cancer patient may be a glioblastoma patient and the cancer may comprise glioblastoma, the cancer patient may be a melanoma patient and the cancer may comprise melanoma, the cancer patient may be a lymphoma patient and the cancer may comprise lymphoma, or cancer patient may be a leukemia patient and the cancer may comprise leukemia.

DESCRIPTION OF EMBODIMENTS

Figure 1:
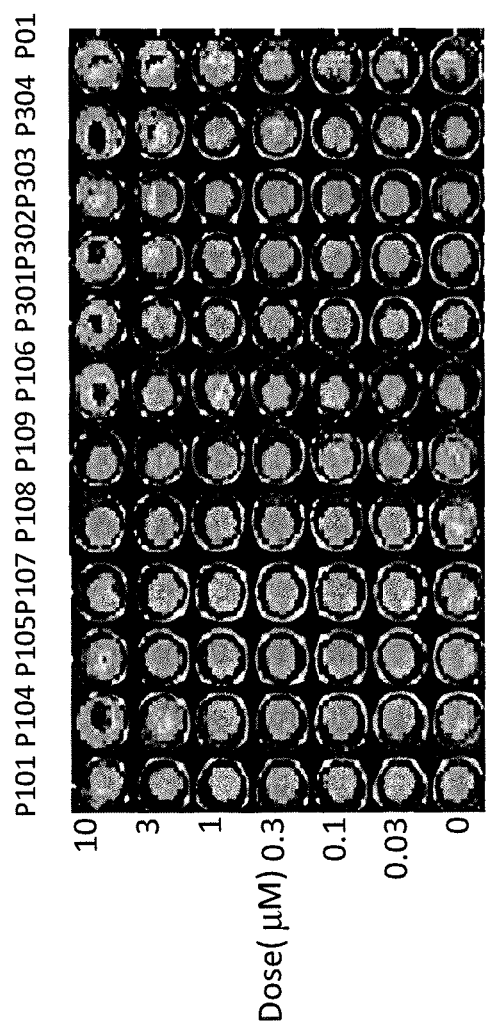
FIG. 1 depicts various aspects of a p53-responsive Luciferase Reporter Assay experiment conducted using prodigio sin analogs.

Various terms relating to aspects of the present disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

As used herein, "alkyl" refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. An alkyl group can be substituted (i.e., optionally substituted) with one or more substituents or can be multi-cyclic as set forth below.

As used herein, "ether" and "ether group" refer to a functional group comprising two hydrocarbon groups covalently linked by an oxygen.

As used herein, "ring structure" includes aryl, cycloalkyl, heteroaryl, and heterocyclyl.

As used herein, "aryl" is art-recognized and refers to a carbocyclic aromatic group. Representative aryl groups include, but are not limited to, phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, heteroaryl, —$CF_3$, —CN, or the like. "Aryl" also includes polycyclic ring systems having two or more carbocyclic rings in which two or more carbons are common to two adjoining rings (the rings are "fused rings") wherein at least one of the rings is aromatic, and the other ring(s) may be, for example, cycloalkyl, cycloalkenyl, cycloalkynyl, and/or aryl. "Haloaryl" refers to an aryl group that is substituted with at least one halogen. In some embodiments, the aromatic group is not substituted (i.e., it is unsubstituted).

As used herein, "cycloalkyl" means a non-aromatic mono- or multi-cyclic ring system of about 3 to about 10 carbon atoms, or about 5 to about 10 carbon atoms. Suitable cycloalkyl rings contain about 5 to about 6 ring atoms. The cycloalkyl can be optionally substituted with one or more "ring system substituents" which may be the same or different, and are as defined herein. Representative monocyclic cycloalkyls include, but are not limited to, cyclopentyl, cyclohexyl, cycloheptyl, and the like. Representative multicyclic cycloalkyl include, but are not limited to, 1-decalin, norbornyl, adamantyl, and the like. In such cycloalkyl groups and, including the $C_5$-$C_7$ cycloalkyl groups, one or two of the carbon atoms forming the ring can optionally be replaced with a hetero atom, such as sulfur, oxygen or nitrogen. Examples of such groups include, but are not limited to, piperidinyl, piperazinyl, morpholinyl, pyrrolidinyl, imidazolidinyl, oxazolidinyl, perhydroazepinyl, perhydrooxazapinyl, oxepanyl, perhydrooxepanyl, tetrahydrofuranyl, and tetrahydropyranyl. $C_3$ and $C_4$ cycloalkyl groups having a member replaced by nitrogen or oxygen include, but are not limited to, aziridinyl, azetidinyl, oxetanyl, and oxiranyl.

As used herein, "heteroaryl" is art-recognized and refers to aromatic groups that include at least one ring heteroatom. In some embodiments, a heteroaryl group contains 1, 2, 3, or 4 ring heteroatoms. Representative examples of heteroaryl groups includes, but are not limited to, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl, —CF$_3$, —CN, or the like. "Heteroaryl" also includes polycyclic ring systems having two or more rings in which two or more carbons are common to two adjoining rings (the rings are "fused rings") wherein at least one of the rings is heteroaromatic, and the other ring(s) may be, for example, cycloalkyl, cycloalkenyl, cycloalkynyl, and/or aryl.

As used herein, "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, but are not limited to, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In some embodiments, the heterocyclyl group is not substituted (i.e., it is unsubstituted).

As used herein, "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof.

As used herein, "subject" and "patient" are used interchangeably. A subject may be any animal, including mammals such as companion animals, laboratory animals, and non-human primates. In some embodiments, the subject is a human.

Embodiments of the present disclosure include prodigiosin analogs which have anti-cancer activity against tumors with mutated p53 proteins. Without intending to be bound to any particular theory or mechanism of action, it is believed that the prodigio sin analogs result in functional reactivation of the p53 pathway in cells with mutated p53 proteins as well as induced expression of the p73 protein and disruption of the interaction between p73 and mutant p53.

Prodigiosin analogs have been developed including various side groups on the three rings of the Prodigiosin core molecule: the A-ring, the B-ring, and the C-ring, as depicted in Formula (B).

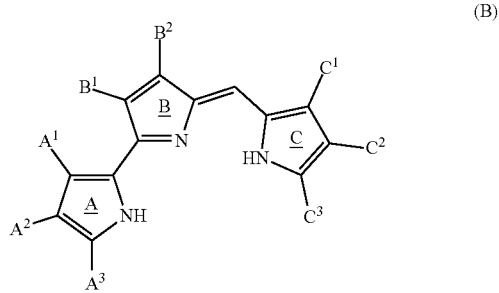

(B)

Prodigiosin analogs may include side groups attached to the core molecule at positions $A^1$, $A^2$, or $A^3$ of the A-Ring, $B^1$ or $B^2$ of the B-Ring, and $C^1$, $C^2$, or $C^3$ of the C-Ring. Embodiments of the present disclosure include prodigiosin analogs with side groups on at least the C-ring of the prodigiosin core molecule, particularly at position $C^2$. In some embodiments, the side group includes a carbonyl group. In some embodiments, the carbonyl side group is an ethyl ester ($CH_2CH_2COR$) or an ethyl secondary amide ($CH_2CH_2CONHR$).

In some embodiments, the prodigiosin analog has the structure of Formula (I) or Formula (II)

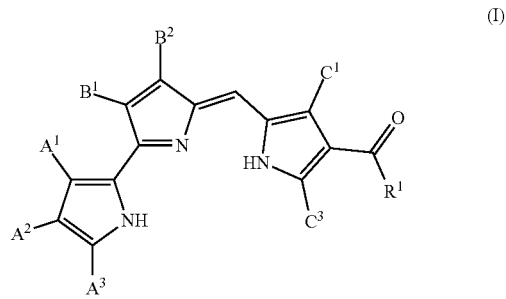

(I)

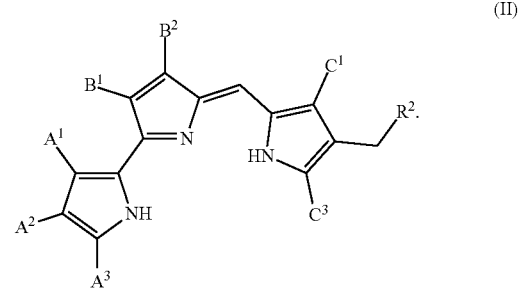

(II)

Formula (I) and Formula (II) are prodigiosin analogs according to Formula (B) wherein $C^2$ is $COR^1$ and $CH_2R^2$, respectively. Formula (I) and Formula (II) may also be represented by tautomeric Formulas (Ia) and (IIa), respectively.

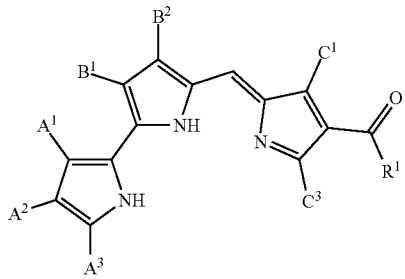

(Ia)

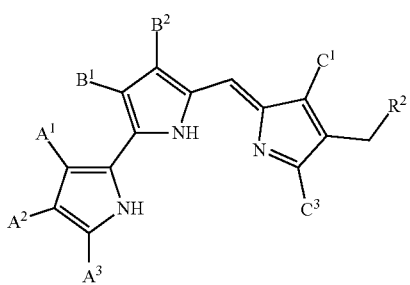

(IIa)

Further prodigio sin analogs according to embodiments of the disclosure are described with respect to Formula (I) and Formula (II). However, one of ordinary skill in the art will understand that each analog could also be expressed as a form of Formula (Ia) or Formula (IIa), the respective tautomers of Formula (I) and Formula (II).

$A^1$, $A^2$, and $A^3$ in Formulas (I) and (II) are, independently, hydrogen, phenyl, $C_1$-$C_{20}$ alkyl or $C_2$-$C_{20}$ alkenyl, wherein the alkyl and alkenyl groups are unsubstituted or substituted by 1 to 3 substituents chosen, independently, from halogen, $C_1$-$C_6$ alkoxy, hydroxy, aryl, and aryloxy. In some embodiments, $A^1$, $A^2$, and $A^3$ are hydrogen. In some embodiments, $B^1$ is hydrogen, $C_1$-$C_6$ alkyl, cyano, carboxy or ($C_1$-$C_6$ alkoxy) carbonyl. In some embodiments, $B^2$ is halogen, hydroxy or $C_1$-$C_{11}$ alkoxy unsubstituted or substituted by phenyl. In some embodiments, $B^1$ is hydrogen and $B^2$ is methoxy. In some embodiments, $C^1$ and $C^3$ are, independently, hydrogen, phenyl, $C_1$-$C_{20}$ alkyl, $C_2$-$C_{20}$ alkenyl, $C_2$-$C_{20}$ alkynyl, or $C_1$-$C_{20}$ alkoxy. In some embodiments, $C^1$ and $C^3$ are methyl.

In some embodiments, the prodigiosin analog has the structure of Formula (III) or Formula (IV)

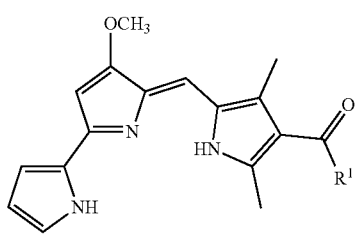

(III)

(IV)

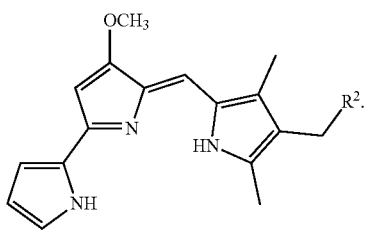

Formula (III) and Formula (IV) are Formula (I) and Formula (II), respectively, where $A^1$, $A^2$, $A^3$, and $B^1$ are hydrogen, $B^2$ is methoxy, and $C^1$ and $C^3$ are methyl.

In some embodiments, the prodigiosin analog has the structure of Formula (V) or Formula (VI)

(V)

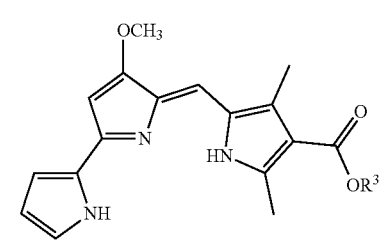

(VI)

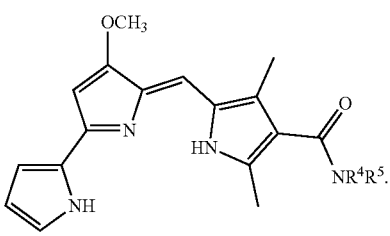

Formula (V) and Formula (VI) are Formula (III), where $R_1$ is $OR_3$ and $NR_4R_5$, respectively.

In some embodiments, the prodigiosin analog has the structure of Formula (Va), (Vb), (Vc), (Vd), or (Ve)

(Va)

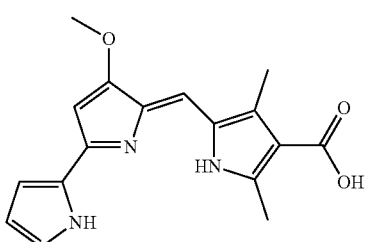

(Vb)

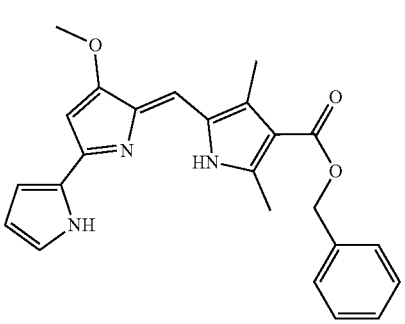

-continued (Vc)

(Vd)

(Ve)

Formula (Va) is Formula (V) where $R^3$ is hydrogen. Formula (Vb) is Formula (V) where $R^3$ is benyzl. Formula (Vc) is Formula (V) where $R^3$ is n-butyl. Formula (Vd) is Formula (V) where $R_3$ is n-octyl. Formula (Ve) is Formula (V) where $R^3$ is 1-pentyne.

In some embodiments, the prodigio sin analog has the structure of Formula (VIa)

(VIa)

Formula (VIa) is Formula (VI), where $R^4$ is hydrogen and $R^5$ is n-butyl.

In some embodiments, the prodigio sin analog has the structure of Formula (VII)

(VII)

Formula (VII) is Formula (III) where $R_2$ is hydrogen.

In some embodiments, the prodigiosin analog has the structure of Formula (VIII)

(VIII)

Formula (VIII) is Formula (III) where $R_2$ is $COR_6$.

In some embodiments, the prodigiosin analog has the structure of Formula (IX) or Formula (X)

(IX)

(X)

Formula (IX) and Formula (X) are Formula (VIII) where $R^6$ is $OR^7$ or $NR^8R^9$, respectively.

In some embodiments, the prodigiosin analog has the structure of Formula (IXa), Formula (IXb), Formula (IXc), or Formula (IXd)

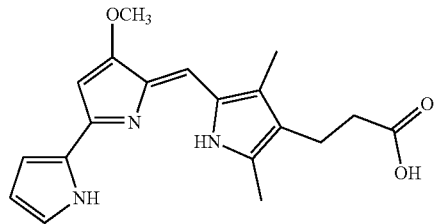
(IXa)

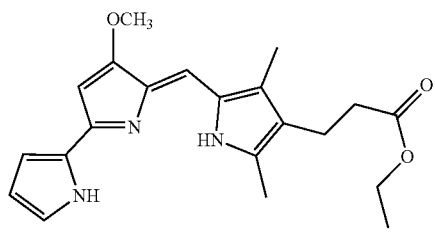
(IXb)

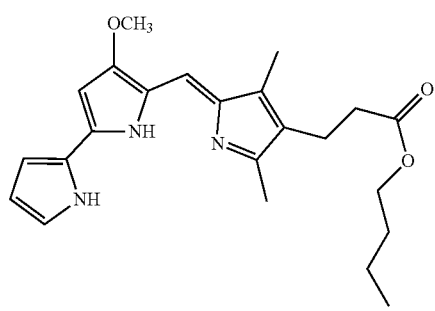
(IXc)

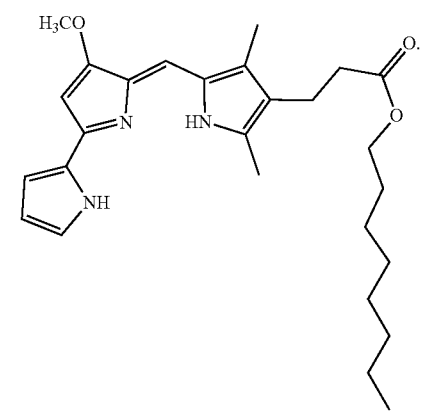
(IXd)

Formula (IXa) is Formula (IX) where $R^7$ is hydrogen. Formula (IXb) is Formula (IX) where $R^7$ is ethyl. Formula (IXc) is Formula (IX) where $R^7$ is n-butyl. Formula (IXd) (PG3-Oc) is Formula (IX) where $R^7$ is n-octyl.

In some embodiments, the prodigiosin analog has the structure of Formula (Xa)

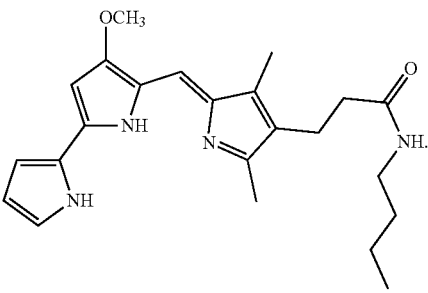
(Xa)

Formula (Xa) is Formula (X) where $R^8$ is hydrogen and $R^9$ is n-butyl.

The compounds may be formulated as a composition, for example, with a carrier. Compositions may comprise a compound of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof. The composition may include more than one compound, including any combination, of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa). The composition may also include one or more other anti-cancer drugs.

Pharmaceutically acceptable salts may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

In some embodiments, the carrier is a pharmaceutically acceptable carrier. Pharmaceutically acceptable carriers include, but are not limited to, aqueous vehicles such as water, alcohol (e.g., ethanol or glycol), saline solutions, dextrose solutions, and balanced salt solutions, as well as nonaqueous vehicles such as alcohols and oils, including plant or vegetable-derived oils such as olive oil, cottonseed oil, corn oil, canola oil, sesame oil, and other non-toxic oils. The compositions may also comprise one or more pharmaceutically acceptable excipients.

In some embodiments, the compositions comprise an effective amount of the compound such as a compound having Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or any combination thereof.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administration. The compositions may be formulated in a suitable controlled-release vehicle, with an adjuvant, or as a depot formulation.

Preparations for parenteral administration include, but are not limited to, sterile solutions ready for injection, sterile dry soluble products ready to be combined with a solvent just prior to use, including, but not limited to, hypodermic tablets, sterile suspensions ready for injection, sterile dry insoluble products ready to be combined with a vehicle just prior to use and sterile emulsions.

Solid dosage forms include, but are not limited to, tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration. Solid dosage forms may be prepared for immediate release, controlled release, or any combination thereof. Controlled release includes, but is not limited to, delayed release, sustained release, timed pulsatile release, and location-specific pulsatile release, and combinations thereof.

Liquid dosage forms include, but are not limited to, aqueous solutions, emulsions, suspensions, solutions and/or suspensions reconstituted from non-effervescent granules and effervescent preparations reconstituted from effervescent granules. Aqueous solutions include, but are not limited to, elixirs and syrups. Emulsions may be oil-in water or water-in-oil emulsions.

Pharmaceutically acceptable excipients utilized in solid dosage forms include, but are not limited to, coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include, but are not limited to, sugar coatings and polymer coatings. Sweetening agents are useful in the formation of chewable tablets and lozenges. Pharmaceutically acceptable excipients used in liquid dosage forms include, but are not limited to, solvents, suspending agents, dispersing agents, emulsifying agents, surfactants, emollients, coloring agents, flavoring agents, preservatives, and sweeteners.

Suitable examples of binders include, but are not limited to, glucose solution, acacia mucilage, gelatin solution, sucrose and starch paste. Suitable examples of lubricants include, but are not limited to, talc, starch, magnesium or calcium stearate, lycopodium and stearic acid. Suitable examples of diluents include, but are not limited to, lactose, sucrose, starch, kaolin, salt, mannitol and dicalcium phosphate. Suitable examples of disintegrating agents include, but are not limited to, corn starch, potato starch, bentonite, methylcellulose, agar and carboxymethylcellulose. Suitable examples of emulsifying agents include, but are not limited to, gelatin, acacia, tragacanth, bentonite, and surfactants such as polyoxyethylene sorbitan monooleate. Suitable examples of suspending agents include, but are not limited to, sodium carboxymethylcellulose, pectin, tragacanth, veegum and acacia.

Suitable examples of coloring agents include, but are not limited to, any of the approved certified water soluble FD and C dyes, mixtures thereof, and water insoluble FD and D dyes suspended on alumina hydrate. Suitable examples of sweetening agents include, but are not limited to, dextrose, sucrose, fructose, lactose, mannitol and artificial sweetening agents such as saccharin, aspartame, sucralose, acelsulfame potassium, and other artificial sweeteners. Suitable examples of flavoring agents include, but are not limited to, synthetic flavors and natural flavors extracted from plants such as fruits and mints, and synthetic blends of compounds which produce a pleasant sensation. Suitable examples of wetting agents include, but are not limited to, propylene glycol monostearate, sorbitan monooleate, diethylene glycol monolaurate and polyoxyethylene laural ether. Suitable examples of enteric-coatings include, but are not limited to, fatty acids, fats, waxes, shellac, ammoniated shellac and cellulose acetate phthalates. Suitable examples of film coatings include, but are not limited to, hydroxyethylcellulose, sodium carboxymethylcellulose, polyethylene glycol 4000 and cellulose acetate phthalate. Suitable examples of preservatives include, but are not limited to, glycerin, methyl and propylparaben, ethylparaben, butylparaben, isobutylparaben, isopropylparaben, benzylparaben, citrate, benzoic acid, sodium benzoate and alcohol.

Suitable examples of elixirs include, but are not limited to, clear, sweetened, hydroalcoholic preparations. Pharmaceutically acceptable carriers used in elixirs include solvents. Suitable examples of syrups include, but are not limited to, concentrated aqueous solutions of a sugar, for example, sucrose, and may contain a preservative. An emulsion is a two-phase system in which one liquid is dispersed throughout another liquid. Pharmaceutically acceptable carriers used in emulsions can also include emulsifying agents and preservatives. Suspensions may use pharmaceutically acceptable suspending agents and preservatives. Pharmaceutically acceptable substances used in non-effervescent granules, to be reconstituted into a liquid oral dosage form, include, but are not limited to, diluents, sweeteners, and wetting agents. Pharmaceutically acceptable substances used in effervescent granules, to be reconstituted into a liquid oral dosage form, include, but are not limited to, organic acids and a source of carbon dioxide. Sources of carbon dioxide include, but are not limited to, sodium bicarbonate and sodium carbonate. Coloring and flavoring agents may be used in all such dosage forms.

Additional excipients that may be included in any dosage forms include, but are not limited to, antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Suitable examples of commonly used antimicrobial agents include, but are not limited to, phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Suitable examples of isotonic agents include, but are not limited to, sodium chloride and dextrose. Suitable examples of buffers include, but are not limited to, phosphate and citrate buffers. A non-limiting example of a chelating agent for metal ions is EDTA.

The disclosure also provides methods for reactivation of the p53 pathway. Such methods may comprise treatment methods, by which reactivation of the p53 pathway treats any condition in which the p53 pathway plays a role, including cancer.

In some embodiments, the methods comprise contacting a cell with mutated p53 with an effective amount of a compound or composition comprising Formula I, Formula II, Formula III, Formula IV, Formula V, Formula VI, Formula VI, or Formula VIII, or any combination thereof, or any pharmaceutically acceptable salt thereof. The composition may comprise any dosage form and/or any excipients, including those described or exemplified herein.

In some embodiments, the methods comprise contacting a cancer cell with an effective amount of a compound or composition comprising any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or any combination thereof, or any pharmaceutically acceptable salt thereof. The composition may comprise any dosage form and/or any excipients, including those described or exemplified herein.

In some embodiments, the methods comprise contacting a cell having a p53 mutation with an effective amount of a compound or composition comprising any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or any combination thereof, or any pharmaceutically acceptable salt thereof. The composition may comprise any dosage form and/or any excipients, including those described or exemplified herein. In contacting the cell in this manner, the compound or composition reactivates the p53 pathway. The cell may be within the body of a subject. The cell may be a cancer cell, such as a prostate cancer cell, a breast cancer cell, a kidney cancer cell, an ovarian cancer cell, a lymphoma cell, a melanoma cell, a leukemia cell, or a glioblastoma cell.

In some embodiments, methods for treating a cancer patient comprise administering to the patient a compound or composition comprising any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or any combination thereof, or any pharmaceutically acceptable salt thereof, in an amount effective to treat the cancer. In some embodiments, the effective amount is an amount effective to reactivate the p53 pathway in cancer cells within the patient's body. In some embodiments, the patient is a human cancer patient. The cancer may be any cancer in which the p53 pathway is mutated including, but are not limited to, prostate cancer, breast cancer, kidney cancer, ovarian cancer, lymphoma, leukemia, melanoma, or glioblastoma.

Administration may be according to any technique or route suitable to the cancer being treated or the patient's needs. Administration may be, for example, oral, parenteral, or via direct injection. Administration may be directly to the tumor or to a location proximal to the tumor. Delivery may be via the bloodstream. Delivery may include active targeting, for example, by conjugating the compound to an antibody that binds to an antigen on the tumor being treated. Delivery may also be passive.

Uses of one or more compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of cancer or tumors are also provided. The disclosure provides compounds which reactivates the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of prostate cancer. The disclosure provides compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of kidney cancer. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of breast cancer. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of ovarian cancer. The disclosure provides uses of compounds which reactivates the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of melanoma. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of lymphoma. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of leukemia. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), and (Xa), or a pharmaceutically acceptable salt thereof, or a composition thereof, in the treatment of glioblastoma. Uses may be in the manufacture of a medicament for cancer treatment as provided.

The following examples are provided to further describe the disclosed embodiments in even greater detail. The examples are intended to illustrate, and not to limit, the embodiments disclosed herein.

Example 1: Prodigiosin Analogs and Cell Lines

As used herein, P01 is prodigiosin, P104 is the prodigiosin analog of Formula (VIa), P105 is the prodigiosin analog of Formula (Vb), P107 is the prodigiosin analog of Formula (Vd), P108 is the prodigiosin analog of Formula (Ve), P109 is the prodigiosin analog of Formula (Va), P106 is the prodigiosin analog of Formula (Vc), P301 is the prodigiosin analog of Formula (VII), P302 is the prodigiosin analog of Formula (Xa), P303 is the prodigiosin analog of Formula (IXb), P304 is the prodigiosin analog of Formula (IXa), P305 is the prodigiosin analog of Formula (IXc), P306 is the prodigiosin analog of Formula (IXd), and P01RC is Obatoclax. P101 is another prodigiosin analog of Formula (XI).

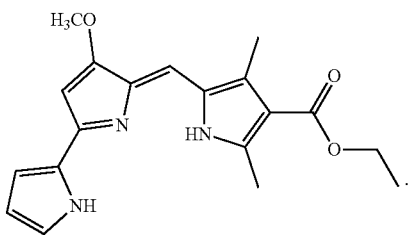

(XI)

Various cell lines were obtained for testing the anti-cancer properties of the prodigiosin analogs described above. SW480, DLD-1, DLD1-p73KD, HCT116, and p53-null HCT116 were generated in the laboratory and each cell stably expressed a p-53 regulated luciferase reporter. MRC5 and Wi38 were obtained from the ATCC and cultured as recommended. Cells were regularly authenticated by bioluminescence, growth, and morphologic observation.

p53-Responsive Luciferase Reporter Assay

Figures 2A, 2B:
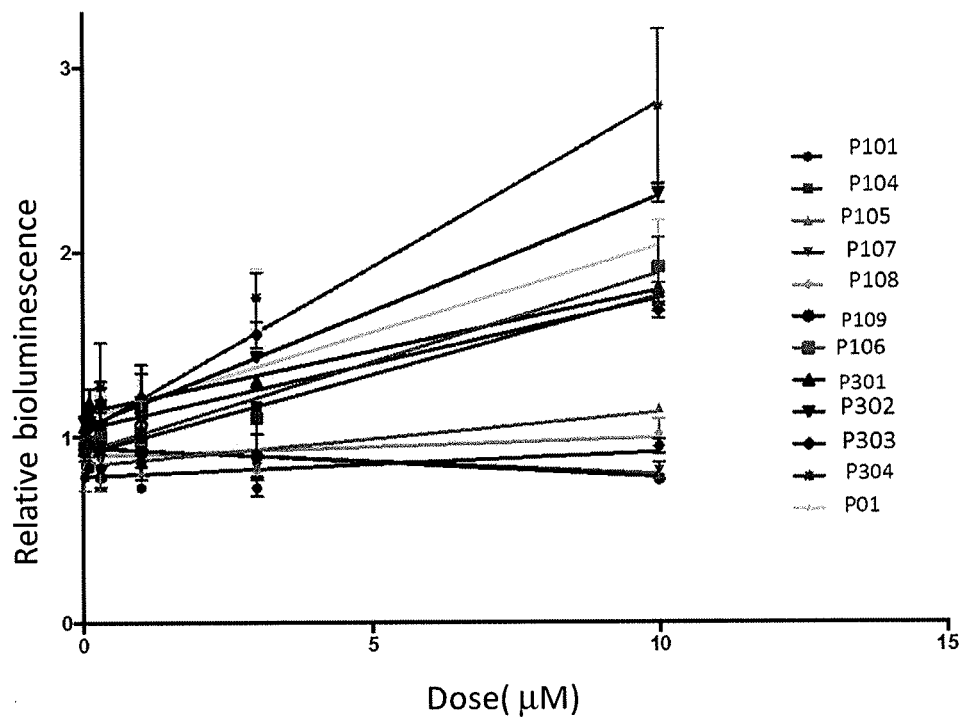
FIGS. 2A and 2B depict various aspects of a p53-responsive Luciferase Reporter Assay experiment conducted using prodigiosin analogs.

The p53-mutant SW480 human colon cancer cells, stably expressing a p53-responsive luciferase reporter, were used for compounds screening. The SW480 cells were treated with P01, P101, P104, P105, P106, P107, P108, P109, P301, P302, P303, and P304 in concentrations ranging from 0.03 µM to 10 µM for 4 hours. After the treatment, cells were imaged by using an IVIS Imaging System (Xenogen) to detect luciferase activity (see, FIGS. 1, 2A, and 2B). Positive hits with strong activity for luciferase induction were selected for additional testing.

Western Blotting

Figure 3:
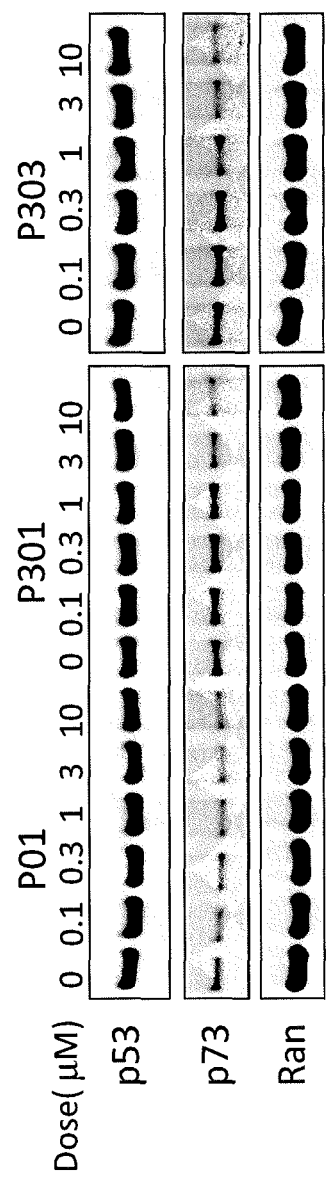
FIG. 3 depicts various aspects of a western blotting experiment conducted using prodigiosin analogs.
Figure 4:
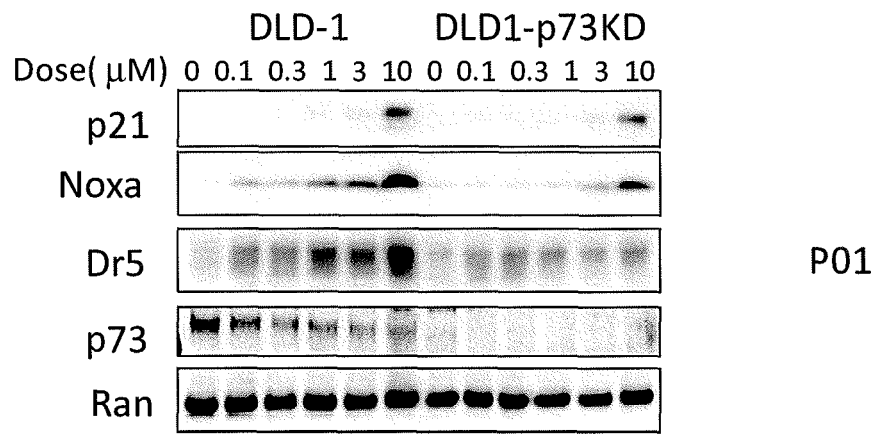
FIG. 4 depicts various aspects of a western blotting experiment conducted using prodigiosin analogs.
Figure 5:
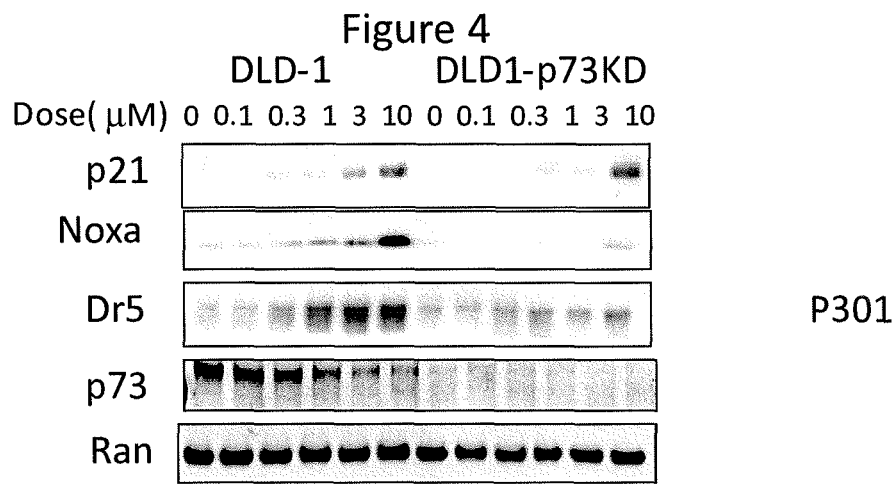
FIG. 5 depicts various aspects of a western blotting experiment conducted using prodigiosin analogs.
Figure 6:
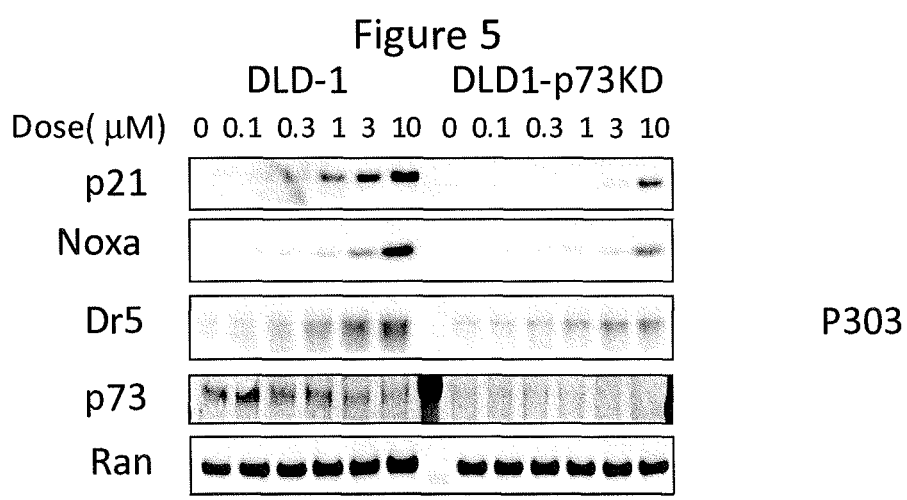
FIG. 6 depicts various aspects of a western blotting experiment conducted using prodigiosin analogs.
Figure 7:
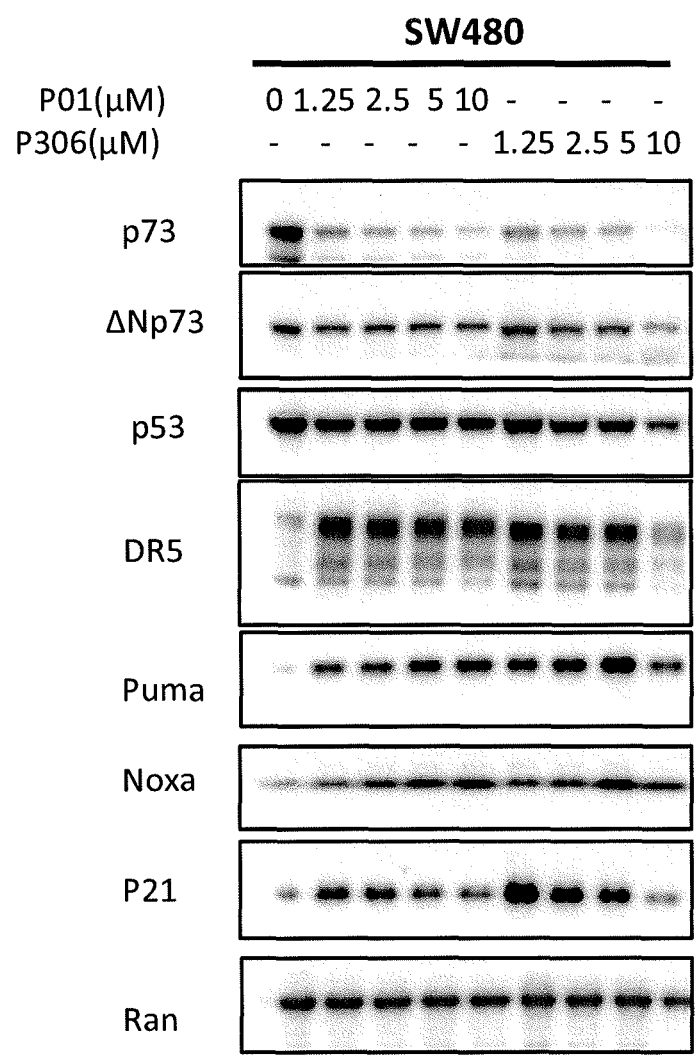
FIG. 7 depicts various aspects of a western blotting experiment conducted using prodigiosin analogs.
Figure 8:
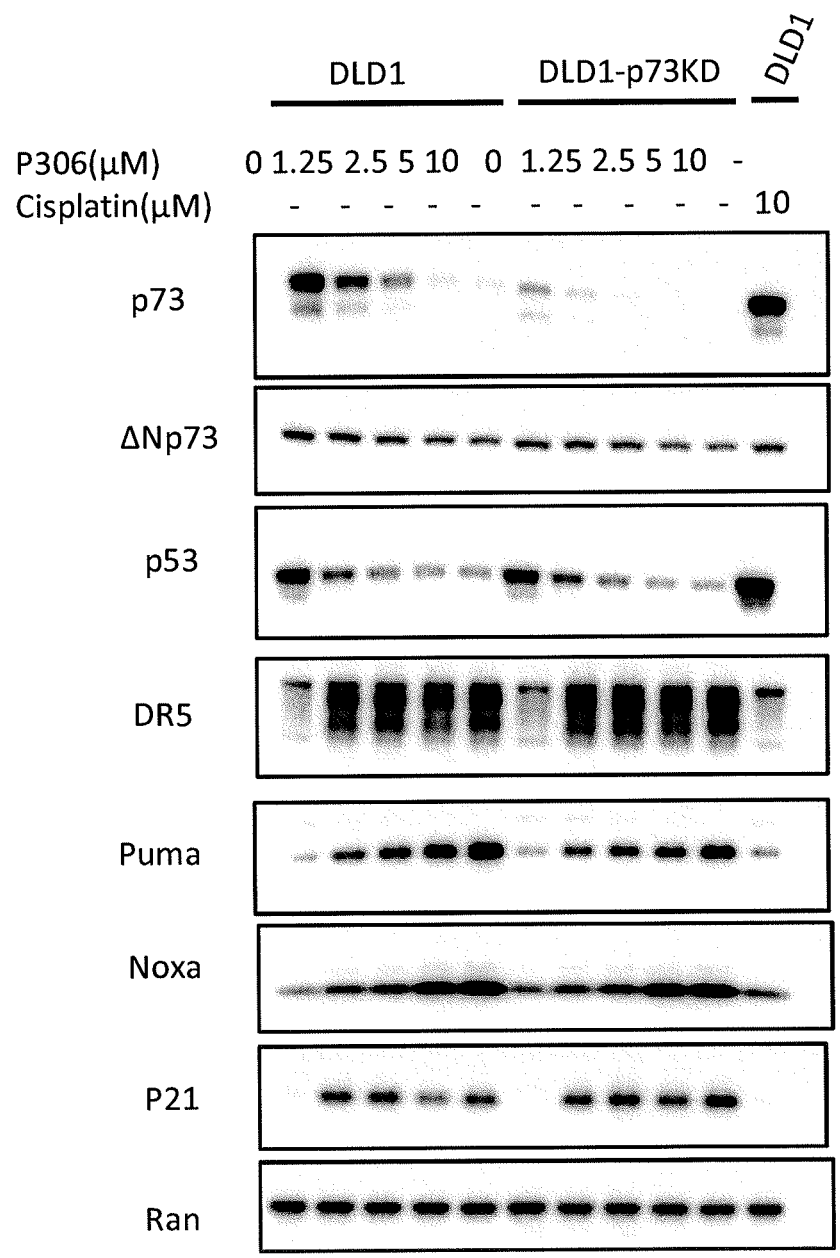
FIG. 8 depicts various aspects of a western blotting experiment conducted using prodigiosin analogs.
Figure 9:
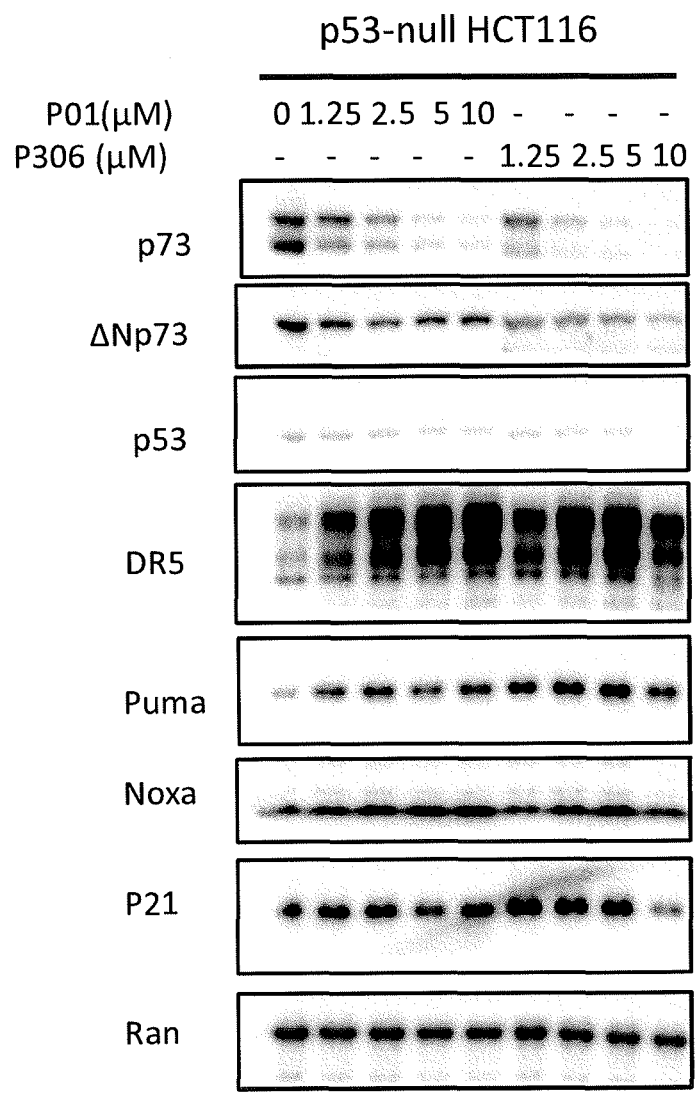
FIG. 9 depicts various aspects of a western blotting experiment conducted using prodigiosin analogs.
Figure 10:
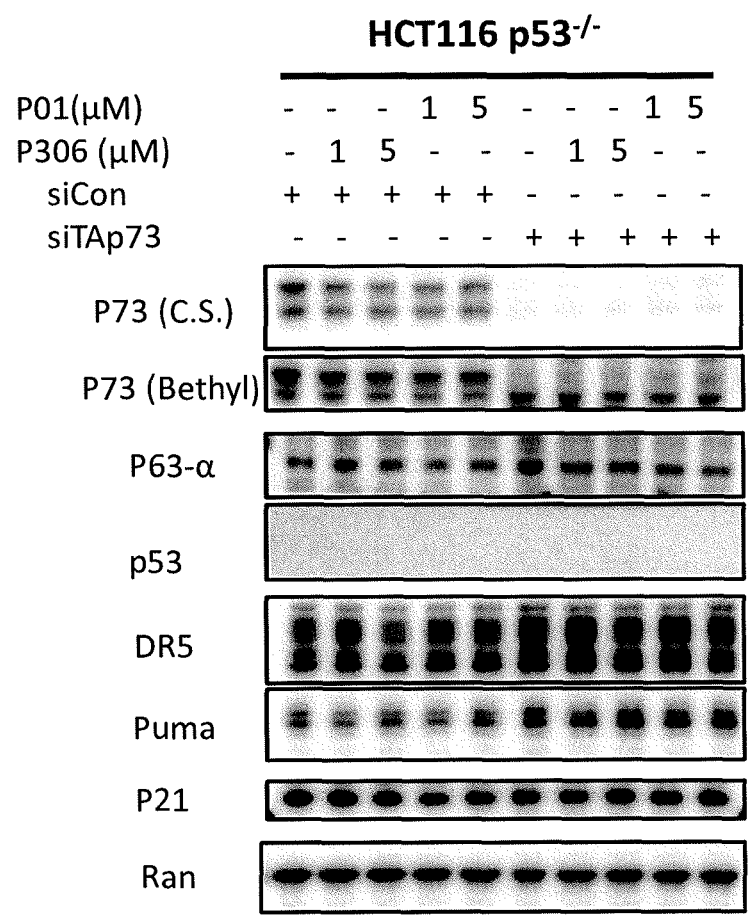
FIG. 10 depicts various aspects of a western blotting experiment conducted using prodigiosin analogs.
Figure 11:
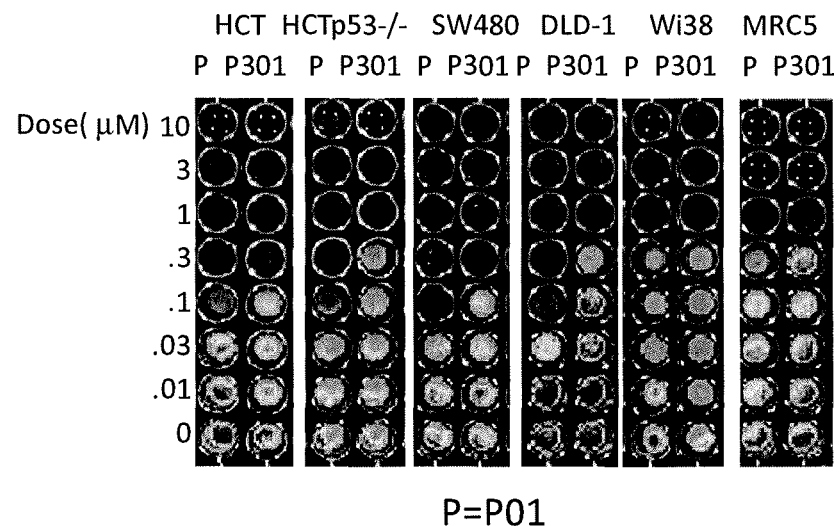
FIG. 11 depicts various aspects of a CellTiter-Glo luminescent cell viability assay experiment conducted using prodigiosin analogs.
Figure 12:
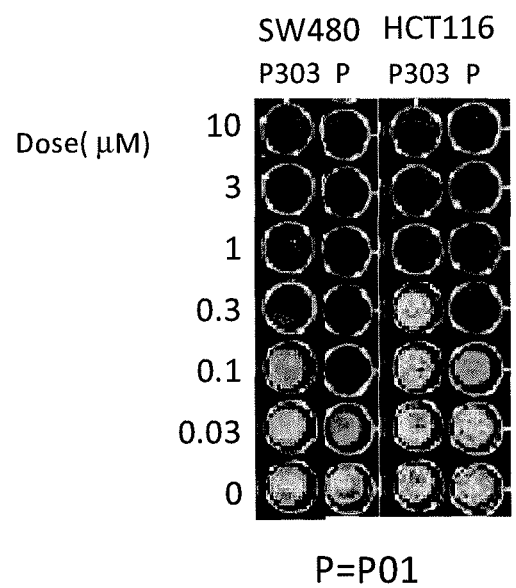
FIG. 12 depicts various aspects of a CellTiter-Glo luminescent cell viability assay experiment conducted using prodigiosin analogs.
Figure 13:
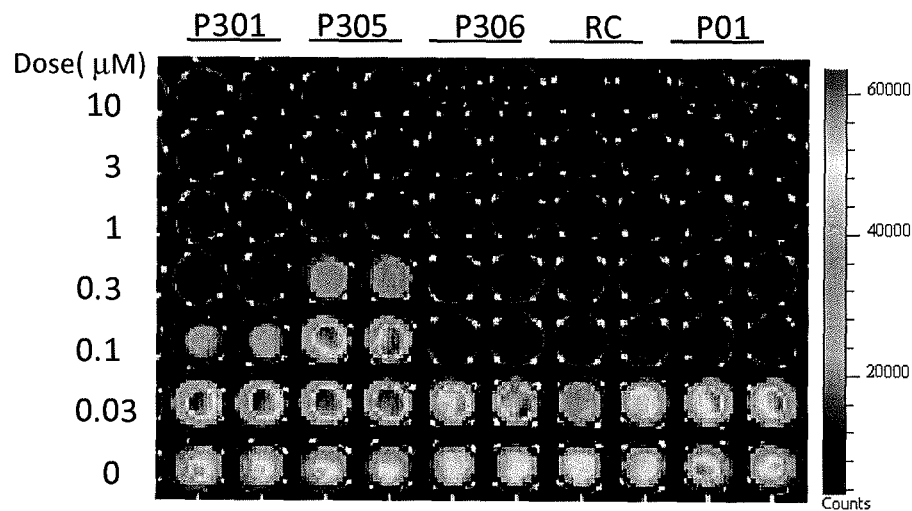
FIG. 13 depicts various aspects of a CellTiter-Glo luminescent cell viability assay experiment conducted using prodigiosin analogs.
Figure 14:
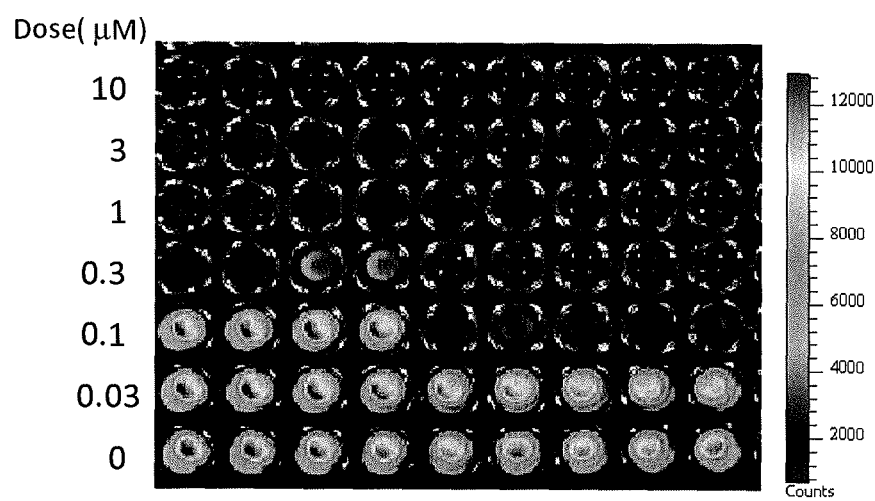
FIG. 14 depicts various aspects of a CellTiter-Glo luminescent cell viability assay experiment conducted using prodigiosin analogs.
Figures 15, 16:
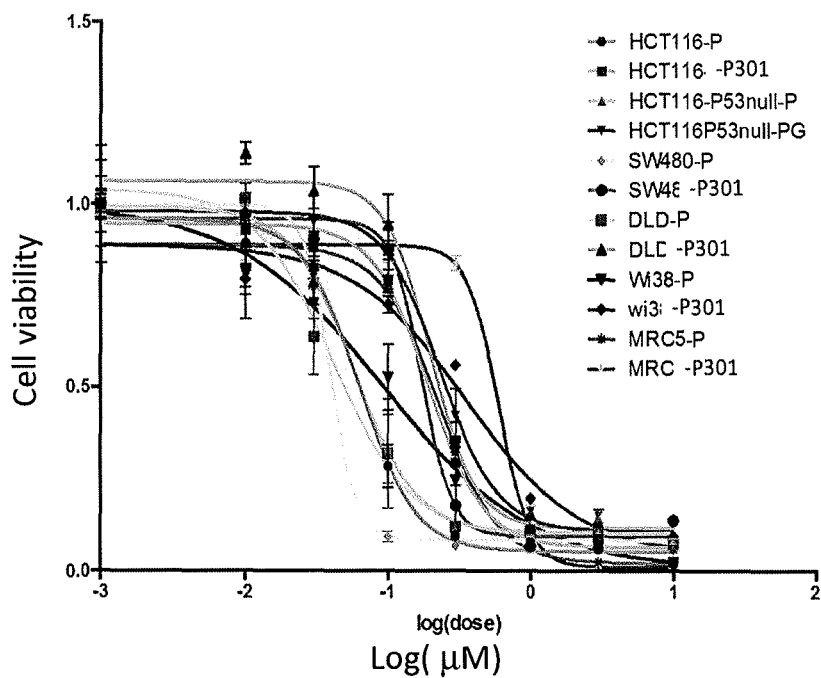
FIG. 15 depicts various aspects of a CellTiter-Glo luminescent cell viability assay experiment conducted using prodigiosin analogs.
FIG. 16 depicts various aspects of a CellTiter-Glo luminescent cell viability assay experiment conducted using prodigiosin analogs.

After treatment, protein lysates were collected for Western blot analysis. Twenty-five micrograms of protein were used for SDS-PAGE. After primary and secondary antibody incubations, the signal was detected with a chemiluminescent detection kit, followed by autoradiography or Syngen. In FIG. 3, SW480 cells were treated with P01, P301, and P303 in various concentrations for 16 hours, and tested for p53, p73, and Ran proteins. In FIGS. 4-6, DLD-1 and DLD1-p73KD cells were treated with P01 (see, FIG. 4), P301 (see, FIG. 5), and P303 (see, FIG. 6) in various concentrations for 18 hours, and tested for p21, Noxa, DR5, p73, and Ran proteins. In FIG. 7, SW480 cells were treated with P01 and P306 in various concentrations for 18 hours and tested for p73, ΔNp73, p53, DR5, Puma, Noxa, P21, and Ran proteins. In FIG. 8, DLD1 and DLD1-p73KD cells were treated with P306 and Cispatlin for 18 hours, and tested for p73, ΔNp73, p53, DR5, Puma, Noxa, P21, and Ran proteins. In FIG. 9, p53-null HCT116 cells were treated with P01 and P306 in various concentrations for 18 hours, and tested for p73, ΔNp73, p53, DR5, Puma, Noxa, P21, and Ran proteins. In FIG. 10, p53-null HCT116 cells were treated with P01 and P306, alone or in combination with SiCon or SiTAp73, in various concentrations for 6 hours, and tested for p73 (C.S.), p73 (Bethyl), P63-a, p53, DR5, Puma, P21, and Ran proteins.

CellTiter-Glo® Luminescent Cell Viability Assay

SW480, DLD-1, DLD1-p73KD, HCT116, and p53-null HCT116, MRC5 and Wi38 cells were seeded at 5,000 cells per well on 96-well plates. The cells were treated for 72 hours with P01, P301, P303, P305, P306, and P01RC in various concentrations. Then, cells were mixed with an equal volume of CellTiter-Glo® reagents (Promega), following the manufacturer's protocol, and bioluminescence imaging was measured using the IVIS imager. The results of the luminescent cell viability assay are presented in FIGS. 11-16.

Flow Cytometry Assay

Figure 17:
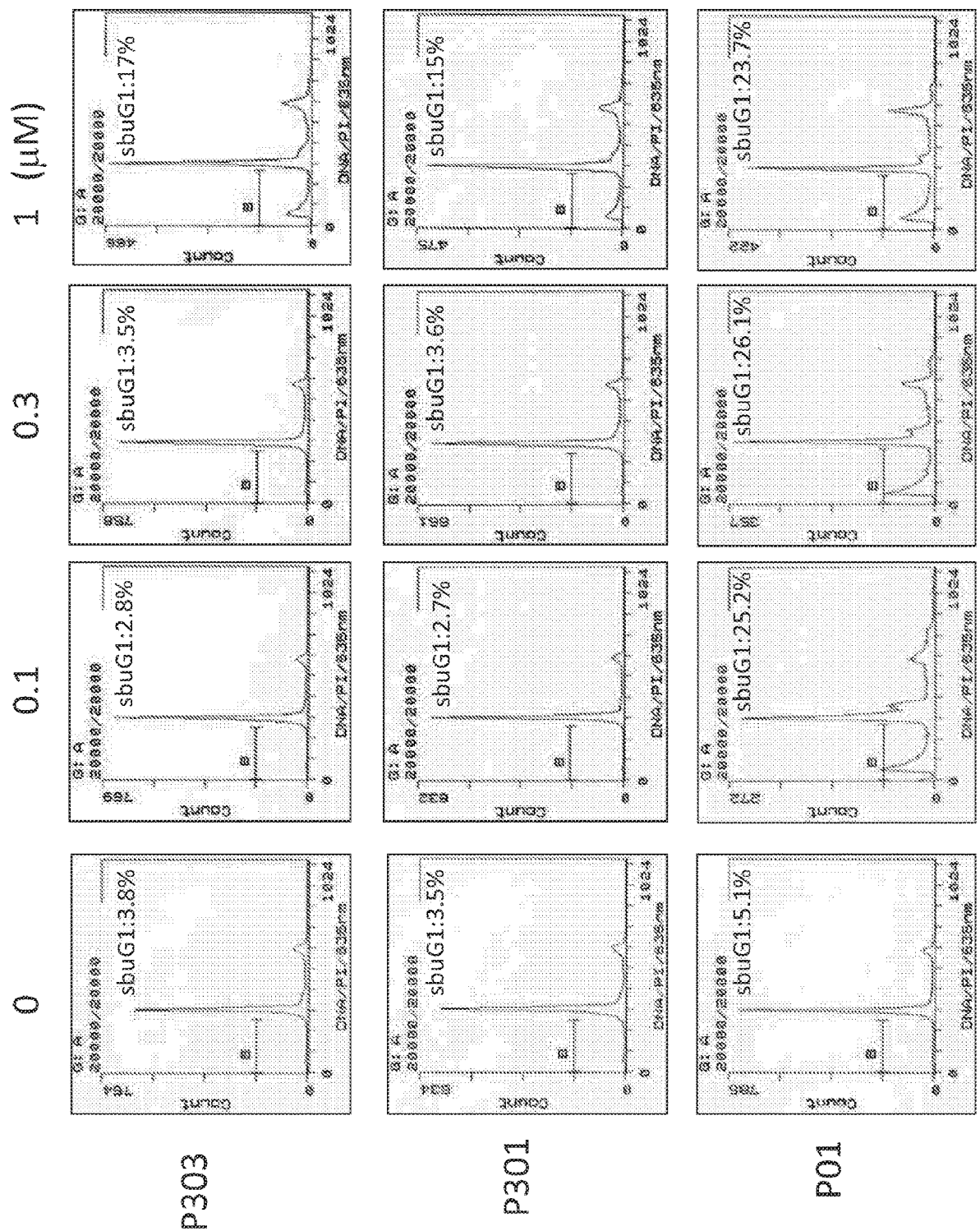
FIG. 17 depicts various aspects of a flow cytometry assay experiment conducted using prodigiosin analogs.
Figure 18:
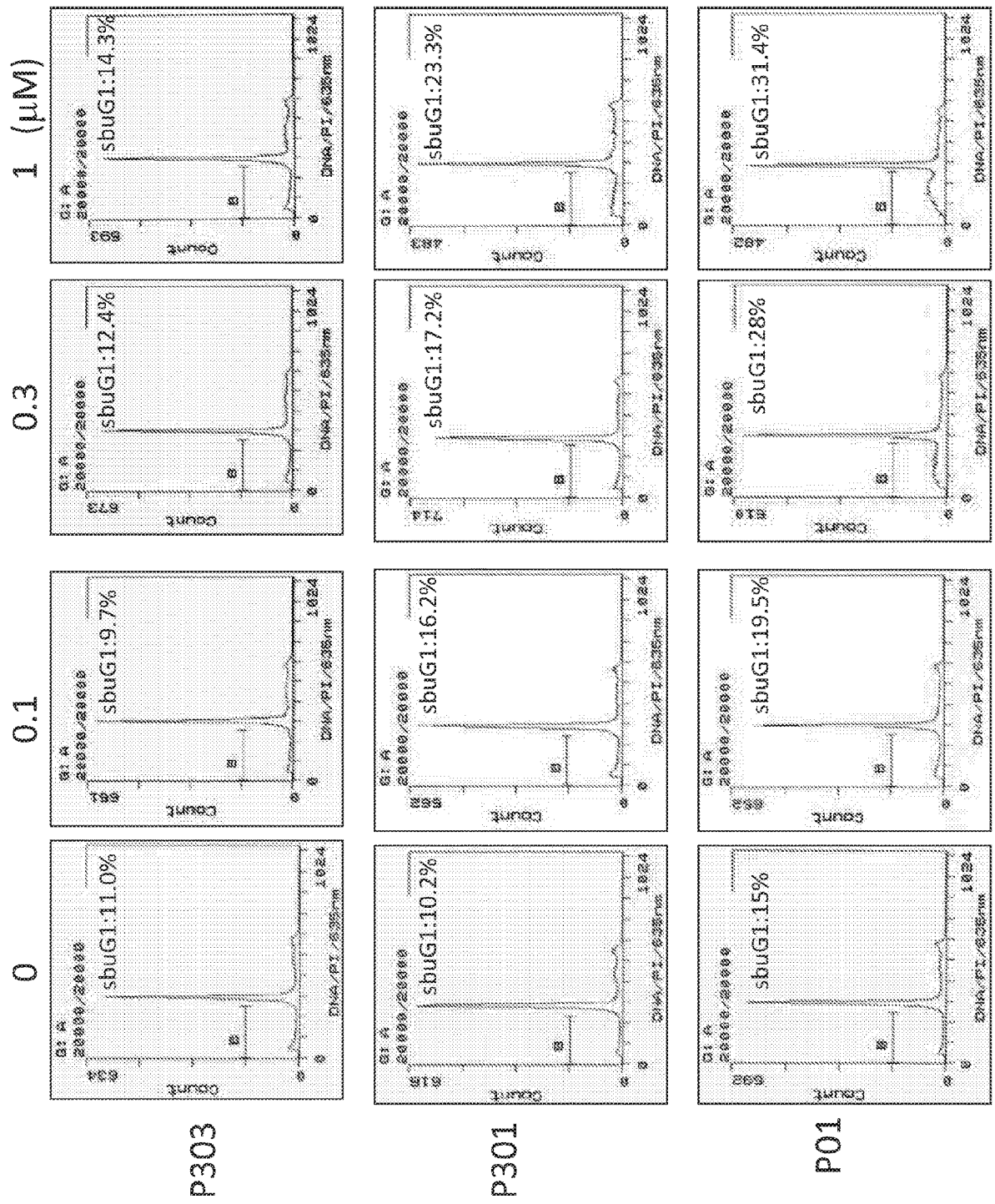
FIG. 18 depicts various aspects of a flow cytometry assay experiment conducted using prodigiosin analogs.
Figure 19:
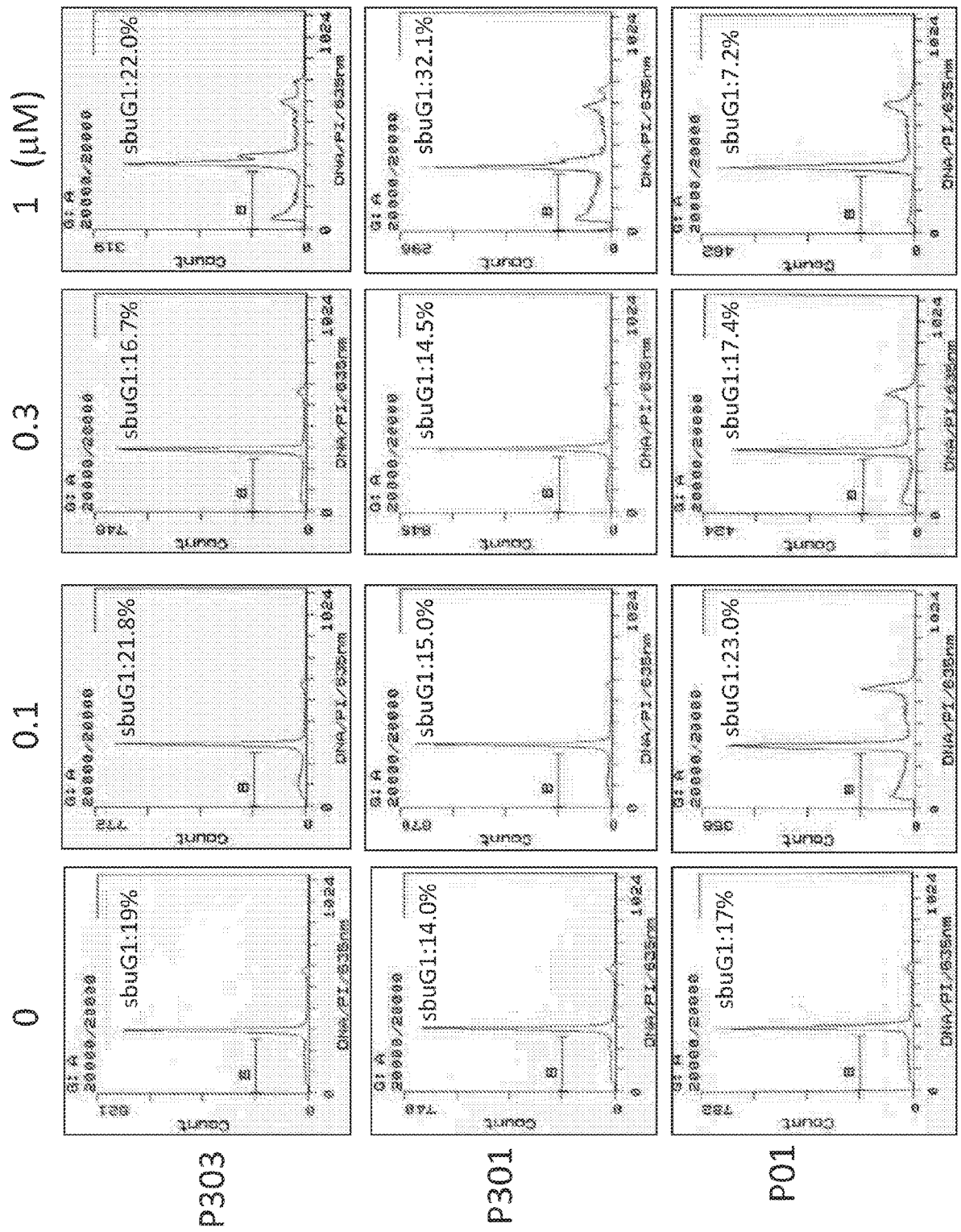
FIG. 19 depicts various aspects of a flow cytometry assay experiment conducted using prodigiosin analogs.

After treatment with P01, P301, and P303 in various concentrations for 72 hours, SW480 (see, FIG. 17), HT29 (see, FIG. 18), and DLD-1 (see, FIG. 19) cells were harvested, fixed by ethanol, and stained by propidium iodide. Flow cytometry was then performed on the resulting cells.

Colony Formation Assay 6-well plates were filled with 500 cells per well of SW480 (see, FIG. 20) and HT29 (see, FIG. 21) cells. The cells were then treated with P01, P301, and P303 in various concentrations for 72 hours. The cells were then cultured with drug-free complete medium for 2 weeks with fresh medium changed every 3 days. Cells were fixed with 10% formalin and stained with 0.05% crystal violet at the end of 2 weeks period of cell culture.

Immunofluorescence

Figure 22:
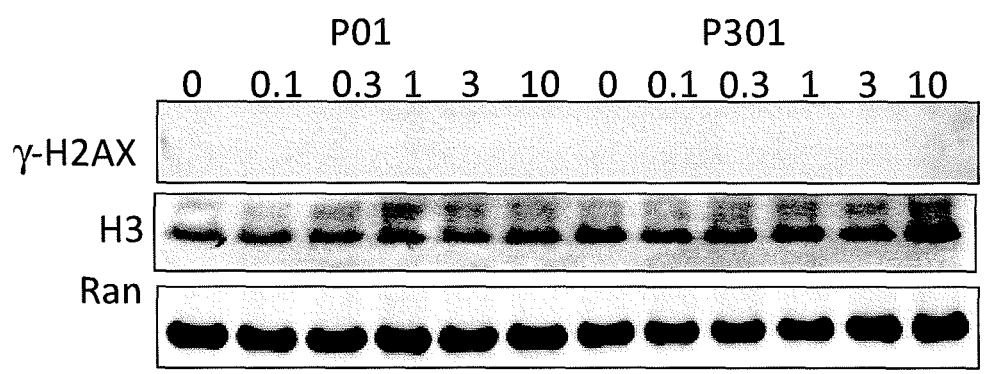
FIG. 22 depicts various aspects of an immunofluorescence experiment conducted using prodigiosin analogs.
Figure 23:
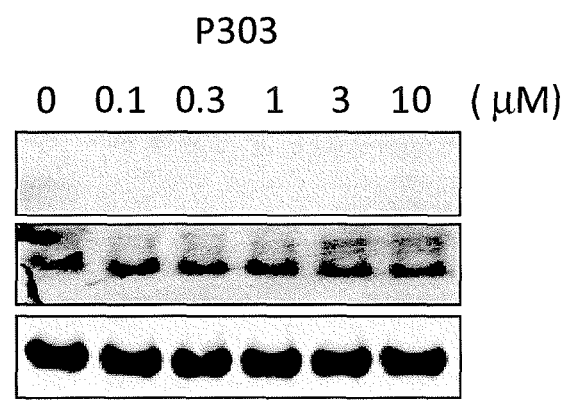
FIG. 23 depicts various aspects of an immunofluorescence experiment conducted using prodigiosin analogs.
Figure 24:
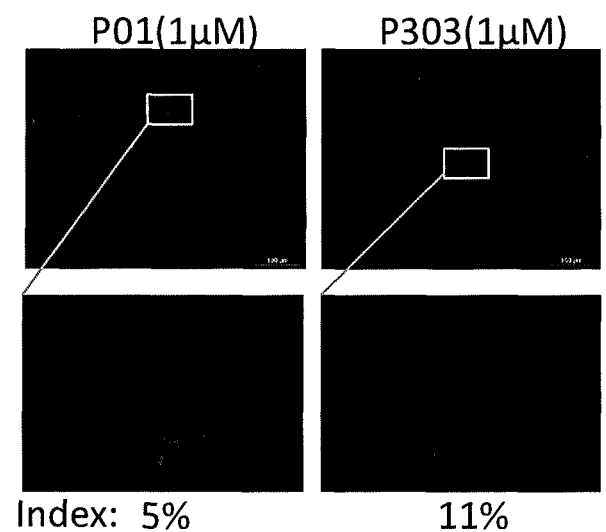
FIG. 24 depicts various aspects of an immunofluorescence experiment conducted using prodigiosin analogs.
Figure 25:
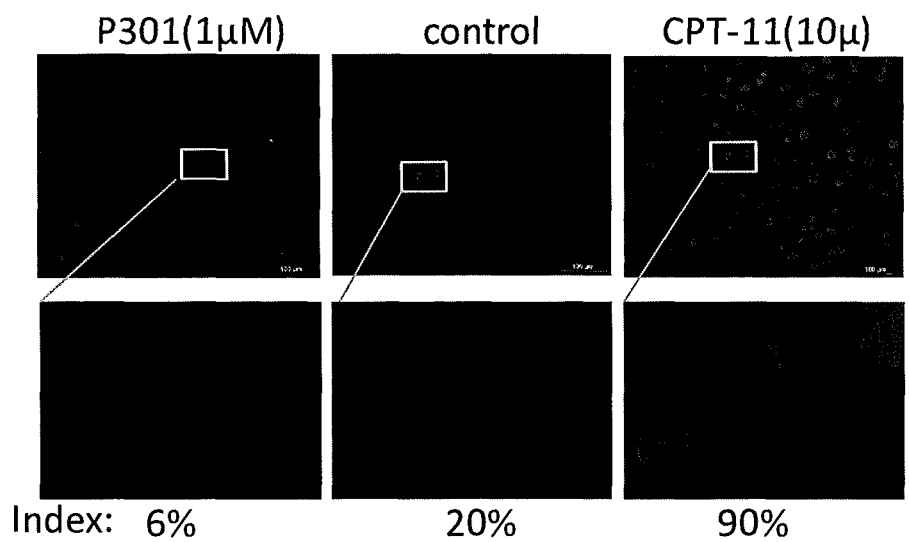
FIG. 25 depicts various aspects of an immunofluorescence experiment conducted using prodigiosin analogs.

SW480 cells were seeded in four-chamber slides. After treatment with P01, P301, P303, and Irinotecan (CPT-11) at various concentrations for 8 hours, cells were fixed by Cytofix/Cytoperm (BD Biosciences) for 30 minutes. Untreated cells were also fixed as a control. Western blotting was used to test for γ-H2AX, H3, and Ran proteins in the cells treated with P01, P301, P303 (see, FIGS. 22 and 23). Fixed cells were blocked for 2 hours, followed by primary antibody incubation for 2 hours and secondary antibody incubation for 2 hours at room temperature. After washing, samples mounted and were examined by fluorescence microscopy (see, FIGS. 24 and 25).

As can be seen from the above experimental results, at least prodigiosin analogs P301 (i.e., Formula (VII)), P303 (i.e., Formula (Xa)), and P306 (i.e., Formula (IXd)) potently induced cell death of p53 mutant colon cancer cell line SW480, DLD1 and p53-null cell line HCT116. The $IC_{50}$ values are within nanomolar range. The prodigiosin analogs induced cell death in cancer cells with no genotoxicity. P301 and P303 induced the expression of p53-target genes via p73. P306 induced mutant p53 and ΔNp73 degradation and the expression of p53-target genes.

Example 2: PG3-Oc (Formula (IXd))

Materials and Methods

1) Cell lines: HT29, SW480, DLD-1, HCT116, and p53-null HCT116 cells, H1975, MDA-MD-231, U251, FaDu, CAL-27, PANC-1, Aspc-1, and MRC5 were obtained from the ATCC and cultured as recommended. Cells were regularly authenticated by bioluminescence, growth, and morphologic observation. The cells were routinely examined for *Mycoplasma* and all cell lines underwent STR authentication.

2) Western blotting: After treatment, protein lysates were collected for Western blot analysis. 15 µg of protein was used for SDS-PAGE. After primary and secondary antibody incubations, the signal was detected by chemiluminescent detection kit, imaged by Syngene (Imgen Technologies). Antibodies for Puma, $FLIP_{L/S}$ and p53 (Santa Cruz Biotechnology), cleaved caspase 8, caspase 9, caspase 3, cleavage PARP, eIF2α, p-eIF2α (Ser51), CHOP, ATF4, DR5, FOXO3a, p-FOXO3a(Ser253), NF-κB p65, p-NF-κB p65 (Ser536), c-Jun, p-c-Jun(Ser63), JNK, p-JNK(Thr183/Tyr185) (Cell Signaling Technology), Noxa, p21 (Calbiochem), p73 (Bethyl laboratories Inc), Ran (BD Biosciences), β-actin (Sigma).

3) Cell viability assay: Cells were seeded in 96-well plate ($6\times10^3$ cells/well). Cells were treated with different concentrations of compounds or dimethyl sulfoxide (DMSO) control for 72 hours. The cell viability was assessed by CellTiterGlo bioluminescent cell proliferation assay (Promega), following the manufacturer's protocol. Bioluminescence imaging was measured using the IVIS imager. Percentage of cell viability (mean±SEM) at each dose was calculated against the respective DMSO control. The $IC_{50}$ values were determined from the sigmoidal dose-response curves using GraphPad Prims4.

4) Caspase activity assay: Cells were seeded in 96-well plate ($1\times10^4$ cells/well). Cells were treated with different concentrations of compounds or DMSO control for 24 hours. The caspase 3/7 activity was assessed by Caspase-Glo® 3/7 Assay kit (Promega), following the manufacturer's protocol. Bioluminescence imaging was measured using the IVIS imager. Caspase activity was normalized to cell numbers and compared to those of DMSO treatment as control in each cell line. Data is reported as mean RLU+ SEM (n=3).

5) Colony formation assays: Five hundred cells were seeded per well on 6-well plates and treated with different concentrations of compounds for 24 hours, then, cells were cultured with drug-free complete medium for 2 weeks with fresh medium changed every 7 days. Cells were fixed with 10% formalin and stained with 0.05% crystal violet at the end of 2 weeks period of cell culture.

6) Flow cytometry assay:

a) Cell Cycle Analysis: Propidium iodide (PI) staining and flow cytometry were used to determine the degree of cellular apoptosis. Cells were seeded at $3\times10^5$ cells/well in six-well plates. Cells were treated with PG3-Oc for 48 hours. Cells were harvested, fixed by 70% ethanol, and stained by propidium iodide, then flow cytometry was performed as previously described (Smithen et al., Org. Biomol. Chem., 2013, 11, 62-68). The percentage of hypodiploid cells (sub-G1) was used to quantify dead cells in apoptosis assays.

b) Early apoptosis detection: Cells were seeded at $3\times10^5$ cells/well in six-well plates. Cells were treated with PG3-Oc for 48 hours. Cells were harvested and prepared using Alex Fluor 488 Annexin V/Dead Cell Apoptosis Kit following manufacturer's protocol (Thermo Scientific Invitrogen).

7) Real-time reverse transcriptase PCR: Total RNA was isolated from PG3-Oc-treated cells using Qick-RNA mini prep kit (Zymo Research, Irvine, Calif.) according to the manufacturer's protocol. 500 ng of total RNA was used to generate cDNA using SuperScript III first-strand synthesis system with random primers (Invitrogen), following the manufacturer's protocol. Real-time PCR was performed using POWER SYBR GREEN mast mix (Applied Biosystem) for DR5, p21, PUMA and GAPDH on 7900HT Sequence Detection System (Applied Biosystem). PUMA primer (forward, 5'-GACGACCTCAACGCACAGTA-3' (SEQ ID NO:1); reverse, 5'-AGGAGTC CCATGAT-GAGATTGT-3' (SEQ ID NO:2)), DR5 primer (forward, 5'-ACAGTTGCAGCCGTAG TCTTG-3' (SEQ ID NO:3); reverse, 5'-CCAGGTCGTTGTGAGCTTCT-3' (SEQ ID NO:4)), GAPDH primer (forward, 5'-TCGACAGTCAGC-CGCATCTTCTTT-3' (SEQ ID NO:5); reverse, 5'-AC-CAAATCCGTTGACTCCGACCTT-3' (SEQ ID NO:6)). ΔΔCt method was used to analyze and report fold change of indicated genes.

8) siRNA knockdown: Knockdown experiments were performed by transfecting either 80 pmole of indicated siRNA(s), or scramble siRNA using RNAiMAX (Invitrogen). Transfected cells were treated with PG3-Oc, 24 hours post-transfection. The control scrambled siRNA and siRNA for human ATF4, CHOP, DR5, Puma, NF-κB p65 were purchased from Santa Cruz Biotechnology. p73 siRNA was from Ambion, and FOXO3a siRNA from Thermo Scientific Dharmacon.

9) Knock-out of PUMA by CRISPR/Cas9 gene editing:

a) sgRNA design and plasmid construction: sgRNA targets the exon 3 of PUMA gene, which contains sequence code for BH3 domain of PUMA. Two sgDNAs (Guide 1 and Guide 2) were introduced into lentiviral vectors (pLenti-CRISPR-E) which contain eSpCas9 and puromycin cassette. Guide1 DNA (forward, 5'-CACCGGCGGGCGGTCCCAC-CCAGG-3' (SEQ ID NO:7); reverse, 5'-AAAC-CCTGGGTGGGACCGCCCGCC-3' (SEQ ID NO:8)) and Guide 2 DNA (forward, 5'-CACCGCCGCTCGTACTGT-GCGTTG-3' (SEQ ID NO:9); reverse, 5'-AAACCAAC GCACAGTACGAGCGGC-3' (SEQ ID NO:10)) were annealed and linked to the restriction enzyme-cut plasmid by T4 ligase. Stb13 strain (Invitrogen C7373-03) was transformed by the guides-containing plasmids. LB-amp plates were streaked and incubated on a shaker at 37 C overnight. The bacteria colonies were selected and mixed up with LB (Terrific Broth) and 100 µg/mL ampicillin, and were incubated on a shaker at 37 C overnight. Plasmids from different colonies were isolated and purified using QIAprep Spin Miniprep Kit (Qiagen). To screen plucks, plasmids were digested with EcoR I HF and Bam HI in Cut Smart Buffer (New England BioLabs, Inc.) at 37 C for 1 hour and then analyzed by 1% agarose gel. Sequencing was performed by GENEWIZ (South Plainfield, N.J., NJ; see, FIGS. 30A-30E and FIGS. 34A-34I).

b) Cell culture, DNA transfection: Lentivirus were generated with psPAX2, pVSV-G and the pLentiCRISPR plasmids that contain the guides and Cas9 in 293T cells. 48 hours later, all the supernatant was transferred to a 1.5 mL tube. The debris was removed by centrifugation and the supernatant was transferred to a new 1.5 mL tube, and stored at 4 C. HT29 cells were transfected with the lentivirus supernatant and polybrene was added to enhance the transfection. Puromycin at a final concentration of 1 µg/mL was added to medium to select positive cells.

c) Mutation screens by Sanger sequencing and TIDE analysis: DNA was extracted and purified from positive HT29 cells using DNeasy Blood & Tissue kit (Qiagen). PCR primers that flank both sides of the exon 3 of PUMA gene were used to amplify the target region (forward, 5'-CACA-GTCTCTGGCCTTCTGG-3' (SEQ ID NO:11); reverse, 5'-AGCTGCCGCACATCTGG-3' (SEQ ID NO:12)). The amplicon is GC-rich region, to improve PCR specificity. Temperature gradient PCR was performed to optimize annealing temperature. A hot-start and touch-down PCR with accuPrime™ Pfx DNA Polymerase (ThermoFisher Scientific) and 2.5% DMSO and 1M betaine, was performed to achieve specific amplification of target region. The PCR products were purified by QIAquick PCR purification kit (Qiagen) for Sanger sequencing. TIDE analysis was performed using an online tool (TIDE: Tracking of Indels by Decomposition (see, world wide web at "tide-calculator.nki.nl/")). Sequencing was performed by GENEWIZ (South Plainfield, N.J., NJ; see, FIGS. 30A-30E and FIGS. 34A-34I).

d) Single cell colonies. 300 positive HT29 cells were placed into a 10 cm dish and incubated at 37 C. After 2 weeks, single cell colonies were selected and expanded. Western blotting using PUMA antibody was performed to screen the colonies (see, FIGS. 30A-30E and FIGS. 34A-34I).

10) Statistical analysis: All results were obtained from triplicate experiments, unless other indicated. Statistical analyses were performed using PRISM4 Software (Graph-Pad Software, Inc.), and the Student t test. Statistical significances were determined by P<0.05. Combination indices were calculated using the Chou-Talalay method with CalcuSyn software (Biosoft).

Results

1) PG3-Oc Inhibits Growth in a Broad Panel of p53-Mutant Cancer Cell Lines:

Efficacy of the newly synthesized analogs was assayed by measuring cell viability, at 72 hours post-treatment. Of the 15 compounds screened, PG3-Oc (see, FIG. 26A) was identified as the most potent inhibitor of cell growth in a broad spectrum of human cancer cells with mutant p53. These included colorectal cancer cell lines (HT29, SW480, DLD1, HCT116 and HCT116 p53$^{-/-}$) and head and neck squamous cell lines (FaDu and CAL-27) (see, FIGS. 26B, 26C and 26D). $IC_{50}$ values for pancreatic cancer cell lines (PANC-1 and ASPC-1), glioblastoma (U251), non-small cell lung cancer (H1975) and triple-negative breast cancer cells (MDA-MB-231 and MDA-MB-468) were within the nanomolar range (see, FIG. 26B). The potency of PG3-Oc (Oc) for inhibition of cancer cell growth was found to be comparable with prodigiosin (P) and obatoclax (Ob) (see, FIG. 26D). PG3-Oc showed similar toxicity for normal cell MRC5 as obatoclax (see, FIG. 26E). For colorectal and head and neck squamous cancer cells, the $IC_{50}$ for normal cells was found to be about 3-fold higher than the values in colorectal and head-neck cancer cells. These data indicate that PG3-Oc can be a suitable compound in the treatment of human colorectal cancers.

Figure 26A:
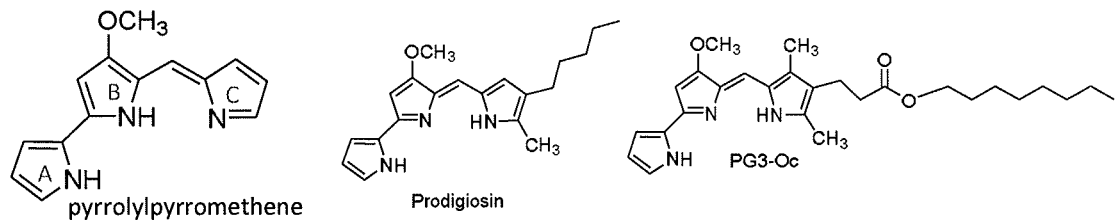
FIGS. 26A, 26B, 26C, 26D, and 26E depict PG3-Oc inhibition of the growth of p53-mutant cancer cell lines.
Figure 26B:
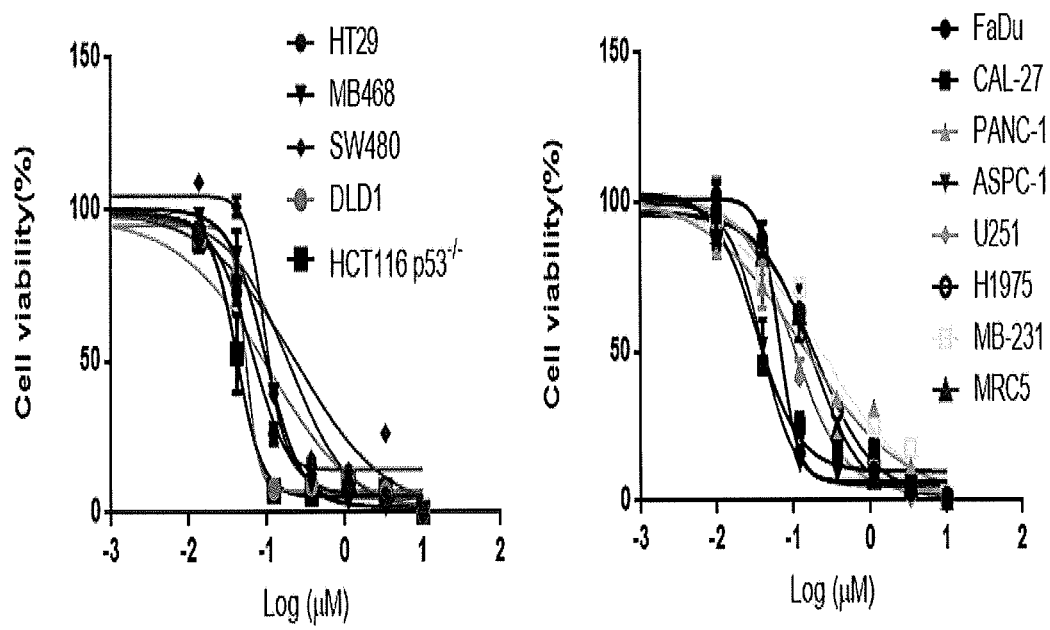
Figure 26C:
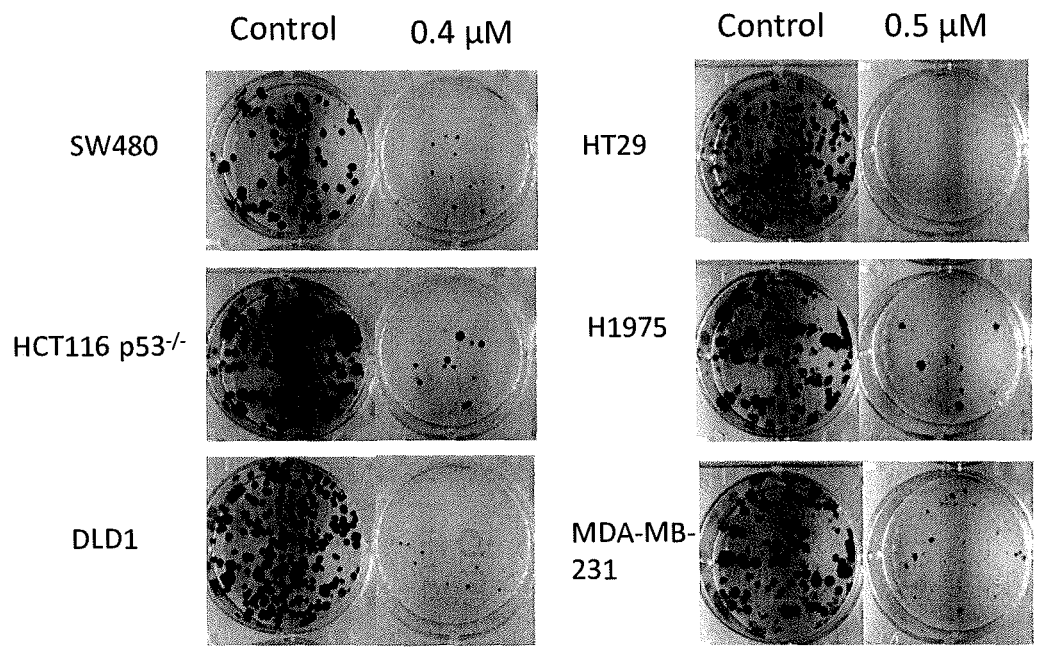
Figure 26D:
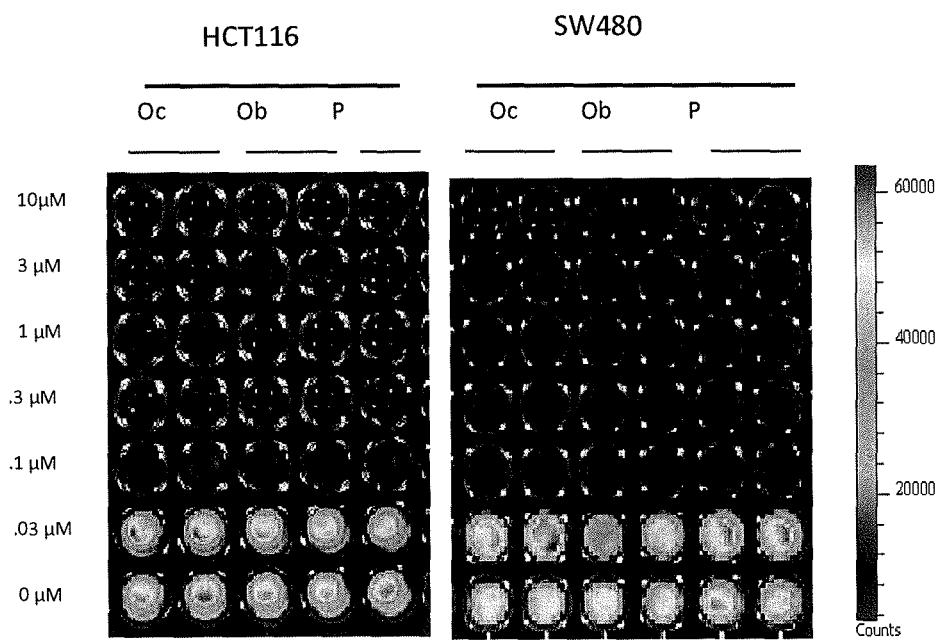
Figure 26E:
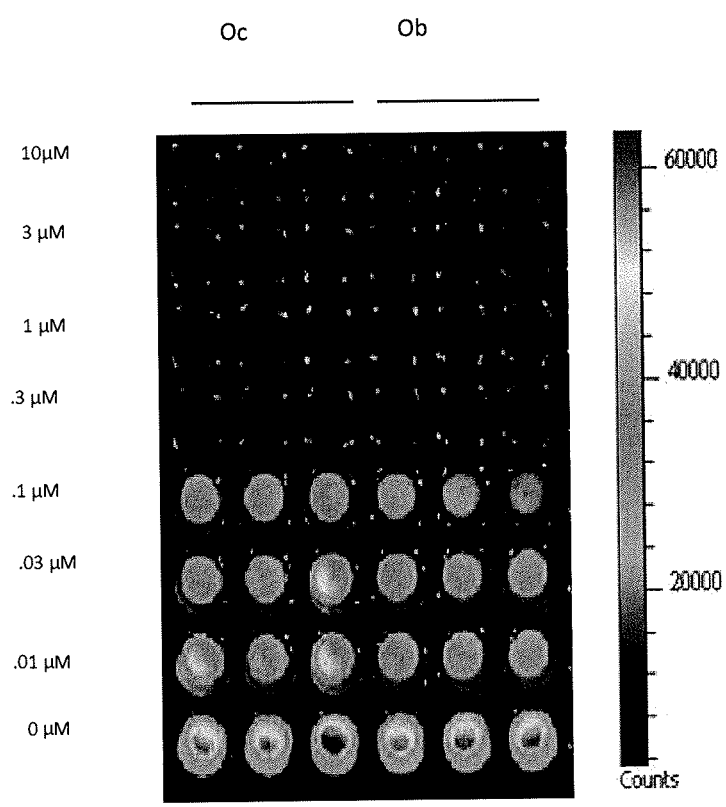

In particular, referring to FIGS. 26A-26E, PG3-Oc inhibition of the growth of p53-mutant cancer cell lines is shown. FIG. 26A shows the structure of PG3-Oc. FIG. 26B shows dose response curves and $EC_{50}$ values of PG3-Oc in a panel of cancer cell lines with p53 mutation, comparing to normal human cells MRC5. FIG. 26C shows colony formation assay of p53-mutant and p53-null human cancer cells. Cells were treated with indicated concentrations of PG3-Oc for 24 hours, and then cultured in drug-free medium for 14 days following crystal violet staining of attached cells. FIG. 26D shows cell viability assay, comparing potency of PG3-Oc (Oc) to obatoclax (Ob) and prodigiosin (P) in p53 wild type cell line HCT116 and p53 mutant cell line SW480. Cells were treated with different concentration of PG3-Oc or DMSO control for 72 hours. Luciferase activity was imaged by the IVIS Imaging System after treatment. Cell viability data were normalized to those of DMSO treatment as control in each cell line and data analyses were performed using PRISM4 software. $EC_{50}$ data are expressed as mean±SD in normal fibroblast cells (normal; n=3). FIG. 26E shows cell viability assay, comparing toxicity of PG3-Oc (Oc) to obatoclax (Ob) in MRC5 cells.

Figure 20:
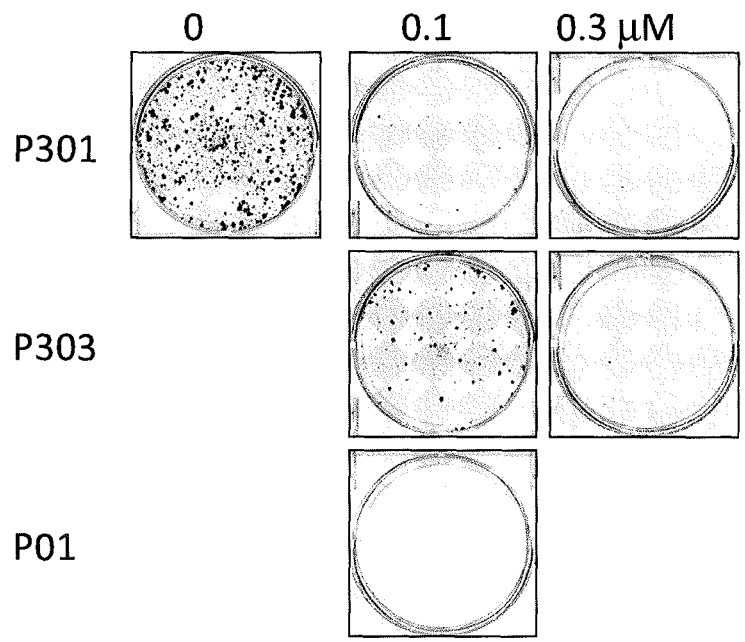
FIG. 20 depicts various aspects of a colony formation assay experiment conducted using prodigiosin analogs.
Figure 21:
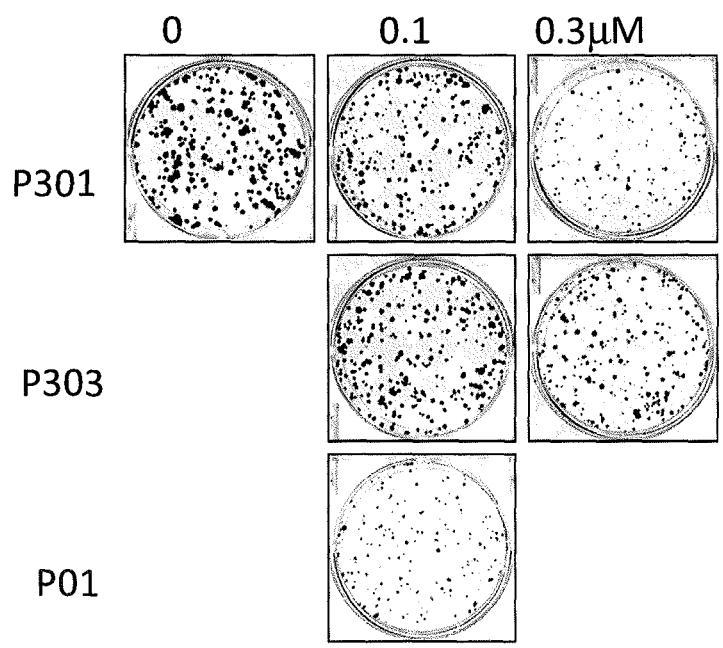
FIG. 21 depicts various aspects of a colony formation assay experiment conducted using prodigiosin analogs.
Figure 27A:
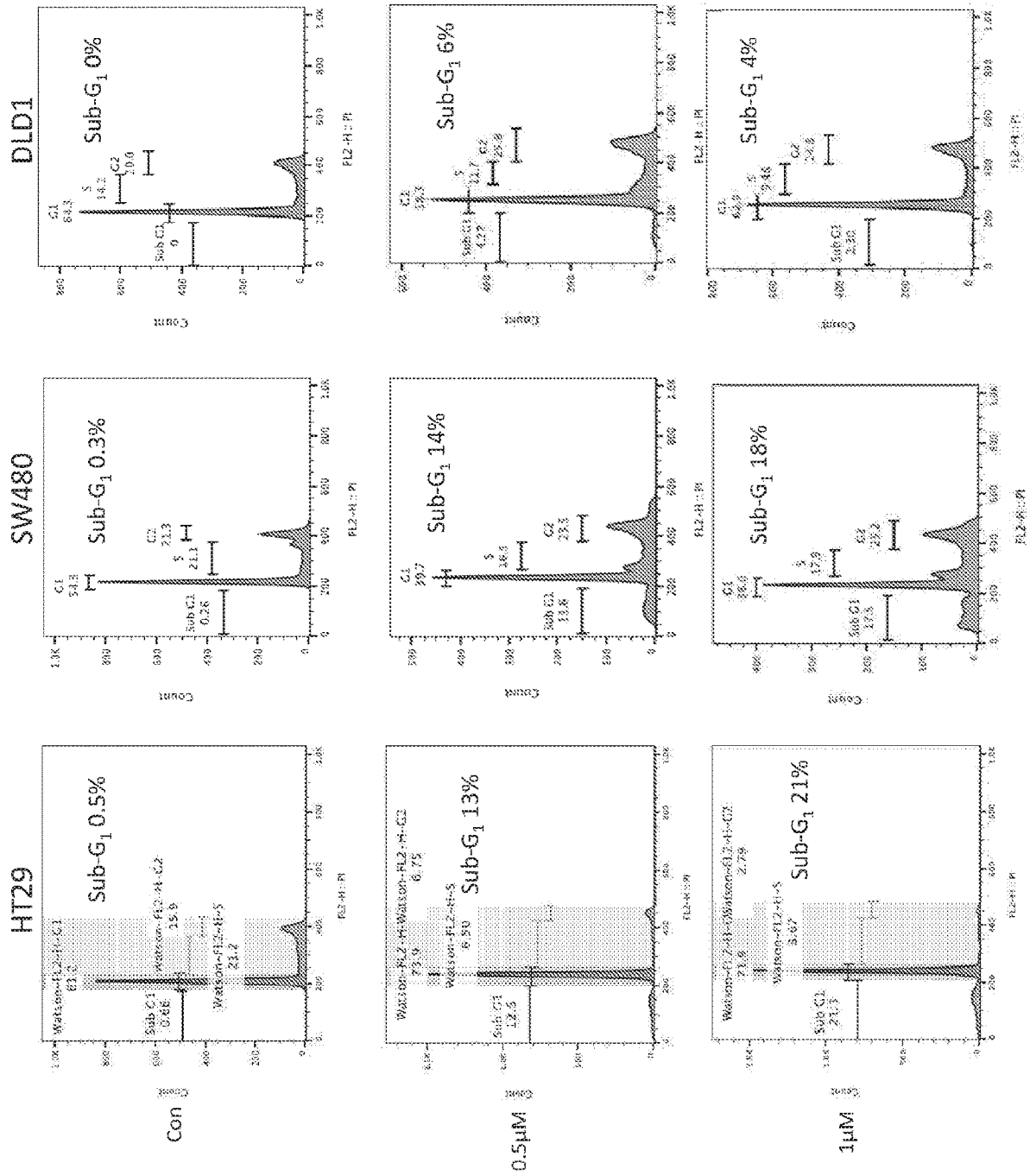
FIGS. 27A, 27B, 27C, 27D, and 27E depict PG3-Oc induction of apoptosis in p53 mutant cancer cell lines, Caspase 3/7 activity assay, HT29 cells co-treated with 1 µM PG3-Oc and pan-caspase inhibitor Z-VAD-fmk, and Western blotting analysis of active caspase-8, active caspase-3 and cleaved PARP in HT29 cells and SW480 cells.

2) PG3-Oc Induces Apoptosis in Mutant p53-Expressing Human Cancer Cell Lines:

Treatment of colorectal cancer cell lines HT29 and SW480 with 1 µM PG3-Oc for 48 hours induced cancer cell death as demonstrated by sub-G1 analysis (see, FIG. 27A). To evaluate if the cell death was caspase-dependent, Caspase 3/7 activity was measured. Treatment with PG3-Oc induced a 2-fold increase in caspase 3/7 activity as compared to untreated cells using mutant p53 and p53-null expressing cancer cells (see, FIG. 27B). Induction of apoptosis was further confirmed by pan-caspase inhibitor (Z-VAD-FMK) co-treatment experiments with PG3-Oc. As seen in FIG. 27C, 20 µM Z-VAD-FMK completely blocked the formation of a sub-G1 population as compared to the untreated control. Under similar experiment conditions, western blot analysis showed that Z-VAD-FMK (20 µM) completely inhibits the cleavage of caspase-8 and caspase-3 in both HT29 and SW480 cells (see, FIGS. 27D and 27E). Taken together, these data indicate that PG3-Oc treatment induces capase-8 and caspase-3 activation in colorectal cancer cell lines, and caspase activation may be required for PG3-Oc-induced cell death.

Figure 27B:
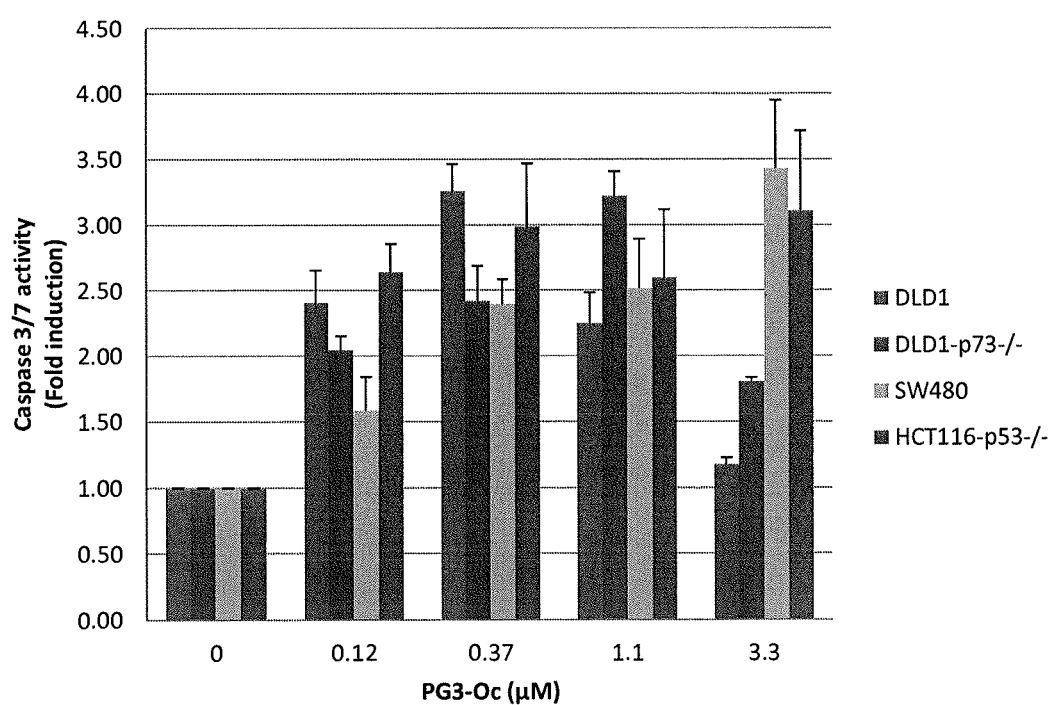
Figure 27C:
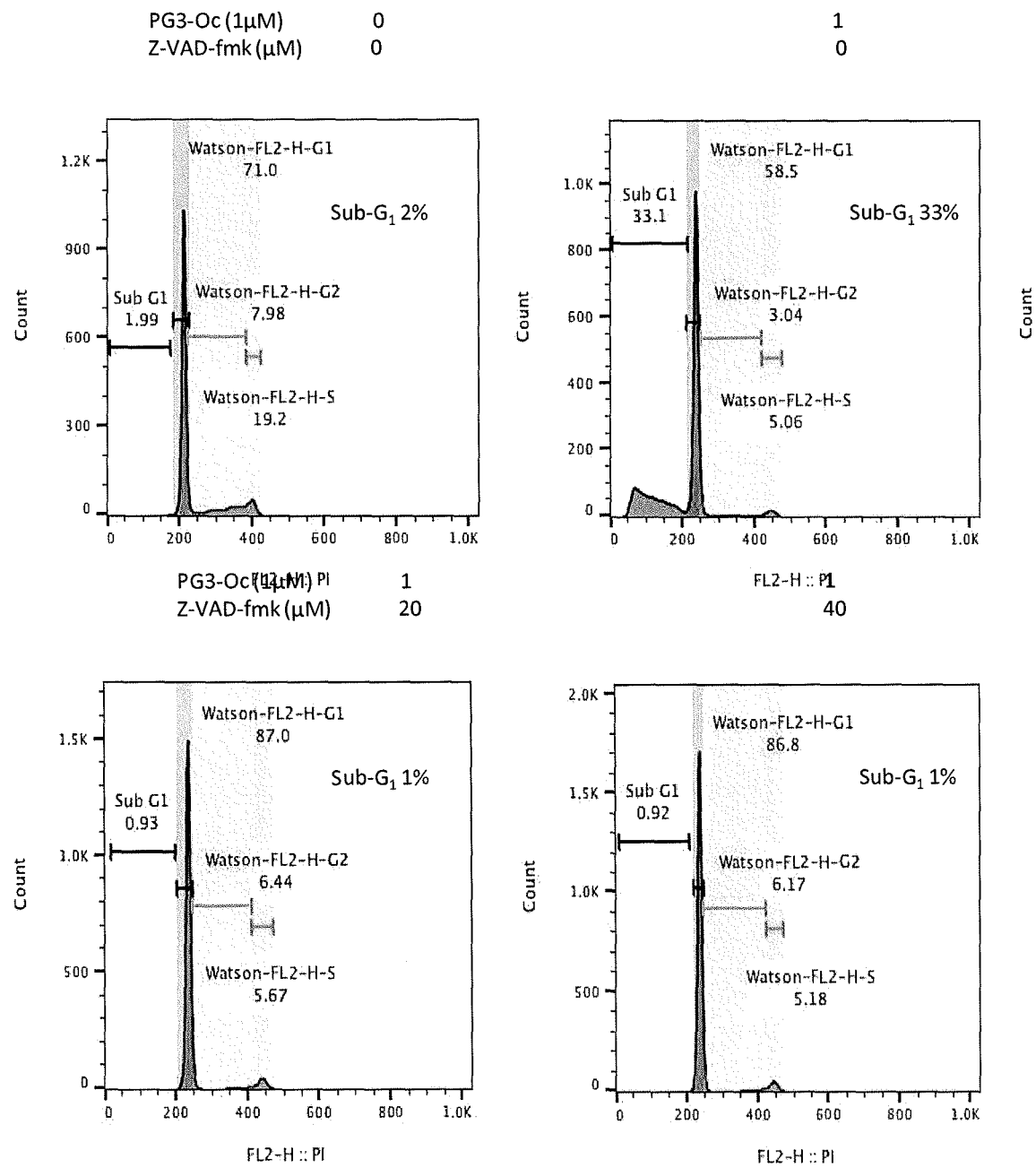
Figure 27D:
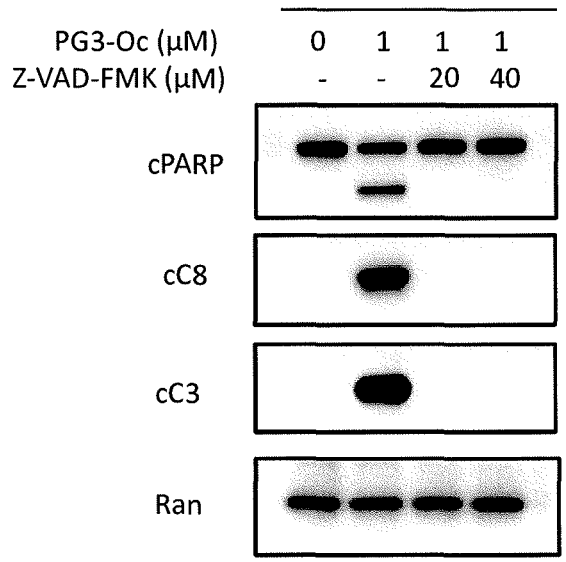
Figure 27E:
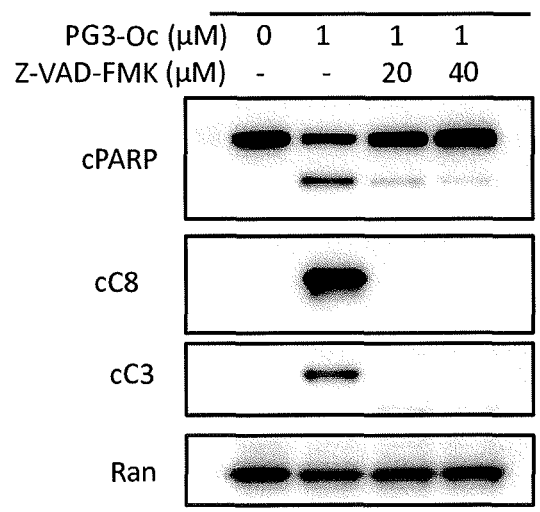

In particular, referring to FIGS. 27A-27E, PG3-Oc-induced apoptosis in p53 mutant cancer cell lines is shown. FIG. 27A shows cell-cycle profiles of cells at 48 hours after PG3-Oc treatment. Apoptosis was analyzed by nuclear PI-staining using flow cytometry. HT29 and SW480 cells were treated with PG3-Oc at indicated concentration for 48 hours, DLD1 cells were treated for 72 hours. FIG. 27B shows caspase 3/7 activity assay. Cells were treated with PG3-Oc at the indicated concentrations for 24 hours. Luciferase activity was imaged by the IVIS Imaging System after treatment. Caspases activity data (triplicate) were normalized to cell numbers and then those of DMSO treatment as control in each cell line and data analyses were performed using Excel. FIG. 27C shows HT29 cells were co-treated with 1 µM PG3-Oc and pan-caspase inhibitor Z-VAD-fmk for 48 hours. Cell cycle analysis was performed as before. Western blotting analysis of active caspase-8, active caspase-3 and cleaved PARP in HT29 cells (see, FIG. 27D) and SW480 cells (see, FIG. 27E).

Figure 28A:
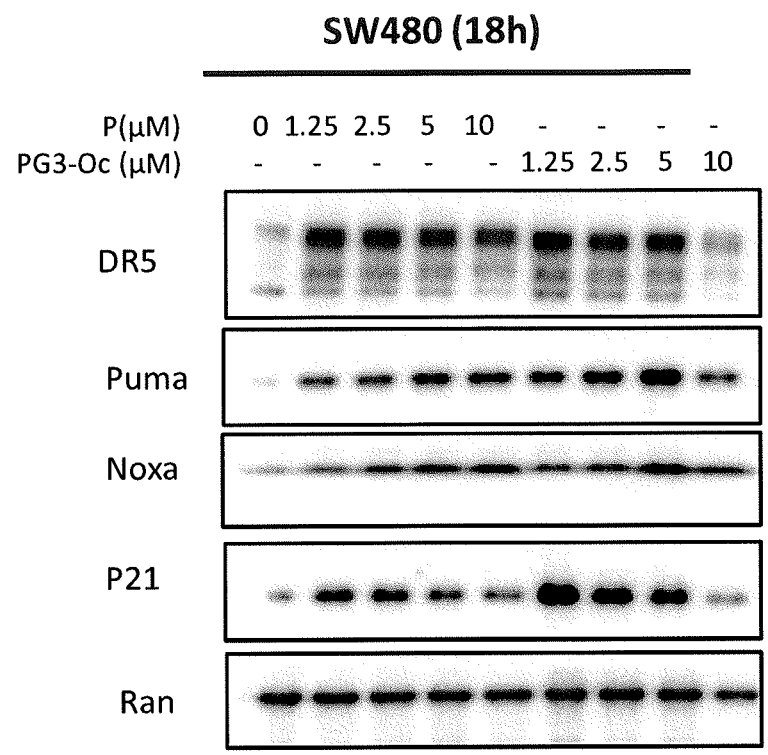
FIGS. 28A, 28B, 28C, and 28D depict PG3-Oc restoration of p53 pathway in p53 mutant cancer cell lines.
Figure 28B:
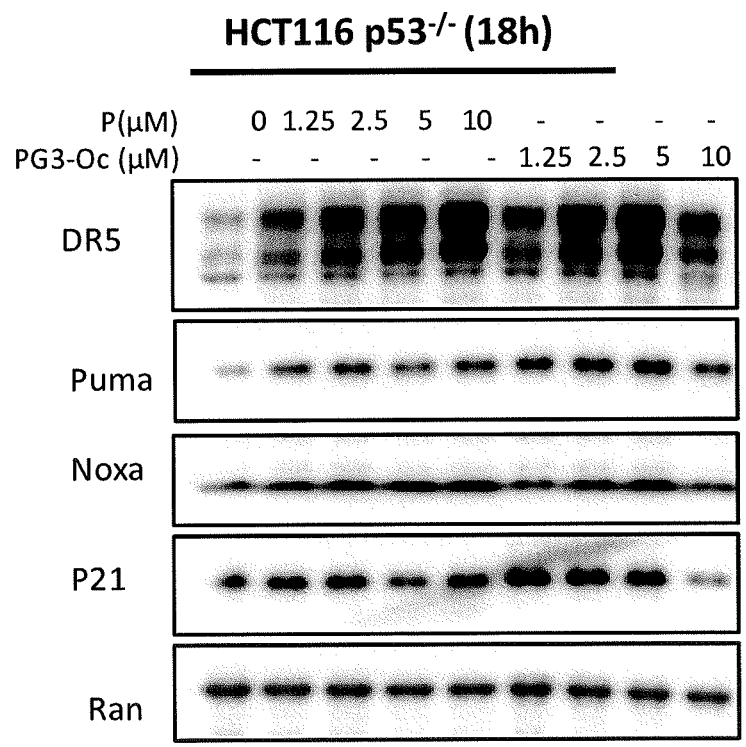

3) PG3-Oc Restores p53 Pathway in p53 Mutant Cancer Cell Lines:

Similar to prodigision, treatment of p53 mutant containing SW480 and p53-null HCT116 colon cancer cells with PG3-Oc also potently induced up-regulation of p53 target genes, such as DR5, PUMA, Noxa and p21 (see, FIGS. 28A and 28B). However, the magnitude of induction of target genes was much higher in PG3-Oc treated cells as compared to prodigiosin, especially for p21 and PUMA (see, FIGS. 28A and 28B). To investigate whether the up-regulation of p53 target genes occurs at the transcriptional level, after cells were treated with 1 µM PG3-Oc at different time points, real-time PCR analysis of mRNA level of DR5, p21 and PUMA was performed in HT29 and HCT116 p53$^{-/-}$ cells (see, FIGS. 28C and 28D). At 8 and 19 hour time points, robust up-regulation of both p21 and PUMA mRNAs were observed in the cell lines tested. For DR5 mRNA level, more than 2-fold up-regulation was observed at 19 hours post-treatment in HT29 cells. Contrary to that, DR5 protein level was potently up-regulated in HCT116 p53$^{-/-}$ cells with no significant change of DR5 mRNA. This indicates that PG3-Oc treatment may lead to DR5 protein stabilization depending on cell type. Taken together, these data indicate that PG3-Oc can restore the p53 pathway at the transcriptional level, especially for p21 and PUMA.

Figure 28C:
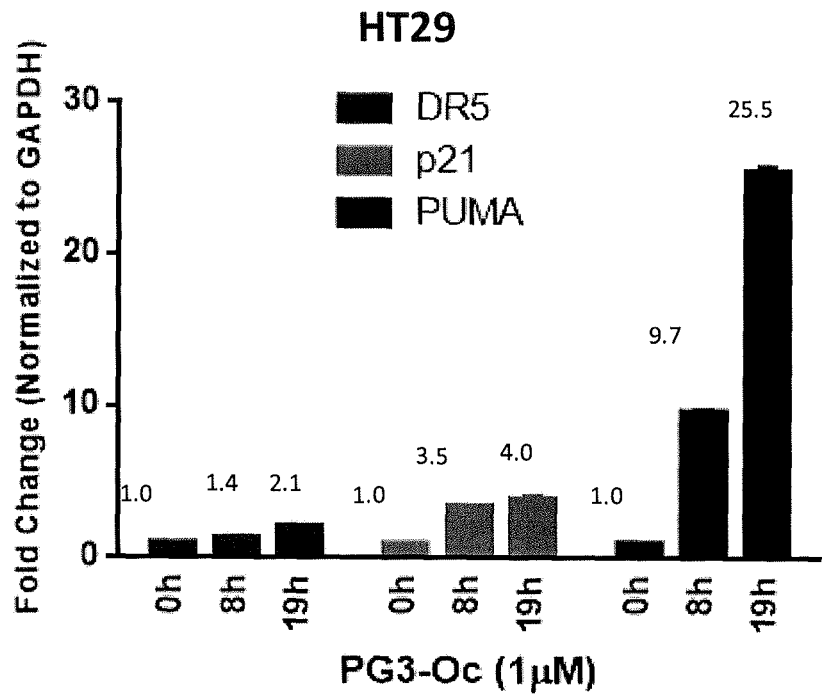
Figure 28D:
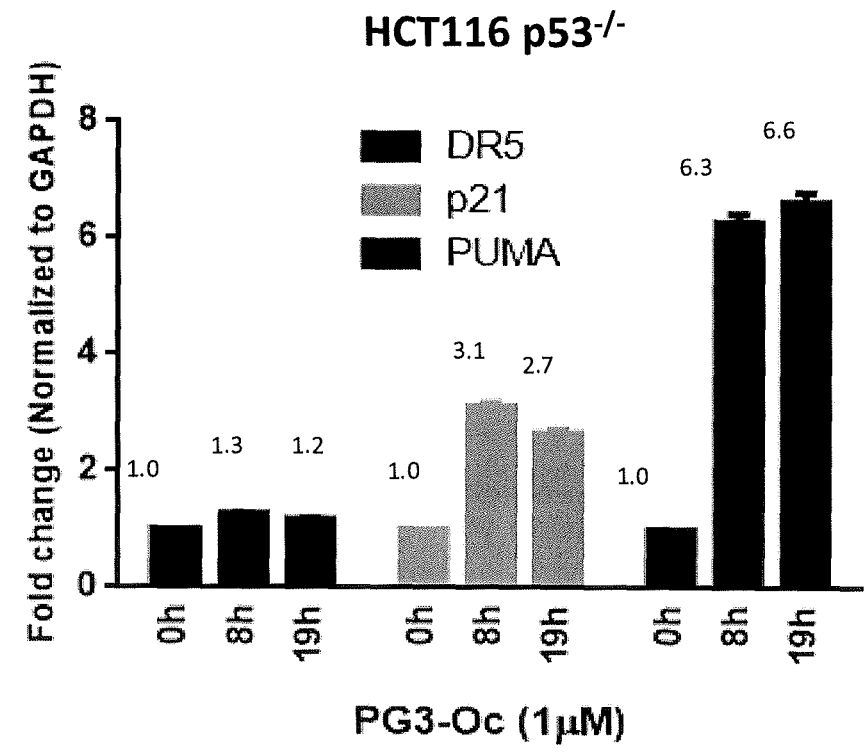

In particular, referring to FIGS. 28A-28D, PG3-Oc restoration of the p53 pathway in p53 mutant cancer cell lines is shown. FIGS. 28A and 28B show PG3-Oc induced expression of p53-target genes in p53-mutant cell lines. PG3-Oc induced more up-regulation of Puma and p21 than prodigiosin (P) in both p53-muant SW480 (see, FIG. 28A) and p53-null HCT 116 cancer cell lines (see, FIG. 28B). Western blot analysis of p53-target gene expression of DR5, Puma, Noxa and p21 in p53-mutat and p53-null cancer cells. Cells were treated with PG3-Oc at indicated concentrations for 18 hours. FIGS. 28C and 28D show qPCR analysis of the change of mRNA level in HT29 and HCT116 p53−/−. Cells were treated with PG3-Oc (1 μM) for 8 hours and 19 hours. mRNA samples were prepared and RT-PCR was performed to prepare cDNAs.

4) PUMA is Required for PG3-Oc Mediated Cell Death:

Whether PUMA and DR5 are dispensable for PG3-Oc mediated cell death in mutant p53 cells was examined. Since PUMA was most dramatically induced by PG3-Oc in HT29 cells, this cell line was selected to dissect out the role of PUMA. Time-course experiments indicated that PUMA protein was first induced at 16 hours post PG3-Oc treatment and this induction was sustained even at 48 hours. At 48 hours, induction of cleaved PARP was observed, as well as cleaved caspase-8 and -3 occurred (see, FIG. 29B). Therefore, 48 hours as a time period was selected for a subsequent dose-response study of PG3-Oc (see, FIGS. 29A and 29C). These data indicate that PG3-Oc induces up-regulation of PUMA in a time-and-dose dependent manner. A similar time- and dose-dependent induction of DR5 was observed in PG3-Oc treated cells.

Having optimized the time and dose of PG3-Oc using different apoptosis markers, siRNA studies were subsequently performed. As shown in FIGS. 29D and 29E, knockdown of PUMA by siRNA reduced the sub-G1 population to 11.1% as compared to 25.8% in siControl, in PG3-Oc treated cells. However, knockdown of DR5 by siRNA did not protect cells from death induced by PG3-Oc (see, FIG. 29D) Similar results were observed by Western Blot analysis when PUMA was knocked down alone or together with DR5 using siRNA. As shown in FIG. 29E, PUMA knockdown completely blunted PARP cleavage and cleavage of caspases post PG3-Oc treatment. However, DR5 knockdown had no impact on the same apoptotic markers. Taken together, this indicates that DR5 is dispensable for PG3-Oc mediated cell death. However, PUMA protein is required and is a key player in cell death induced by PG3-Oc treatment in HT29 cancer cells.

Figure 29C:
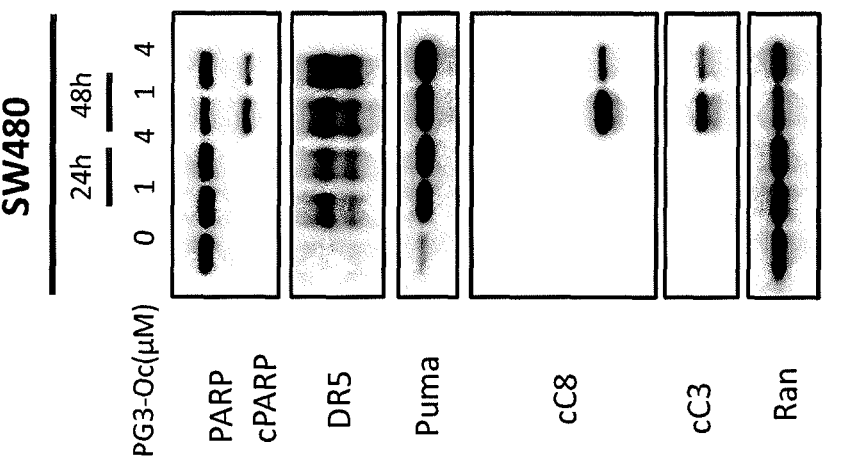
FIGS. 29A, 29B, 29C, 29D, and 29E depict the induction of PUMA is correlated with cell death.
Figure 29B:
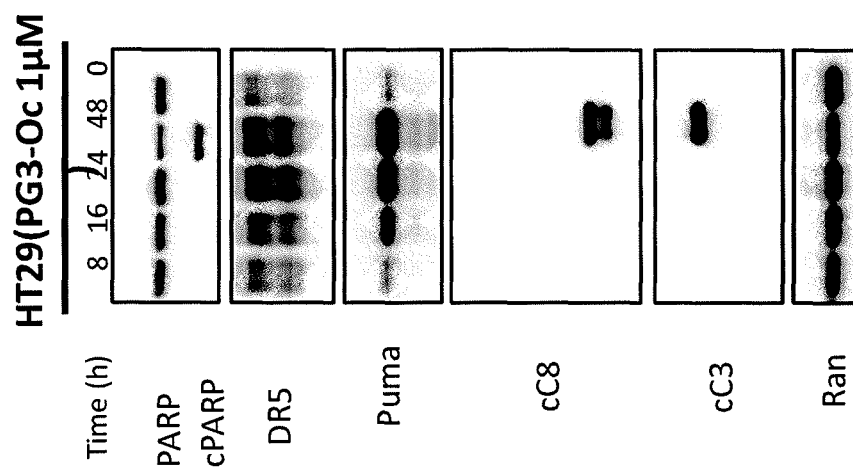
Figure 29A:
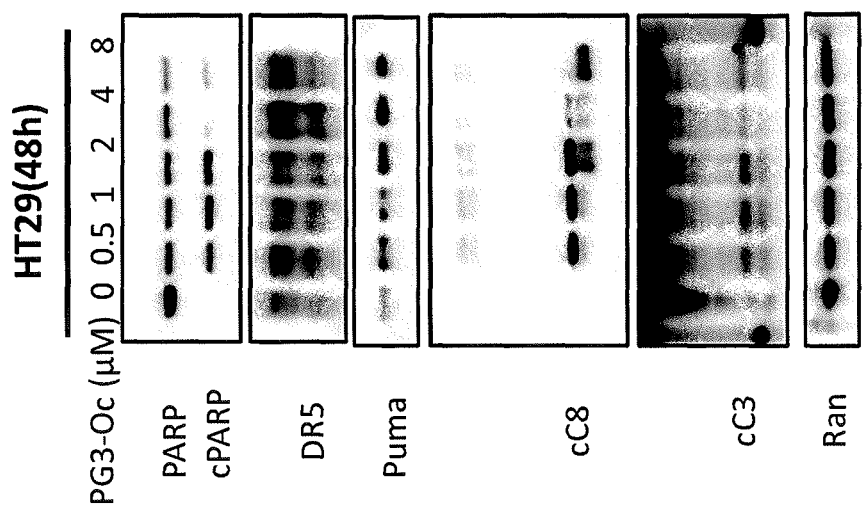
Figure 29D:
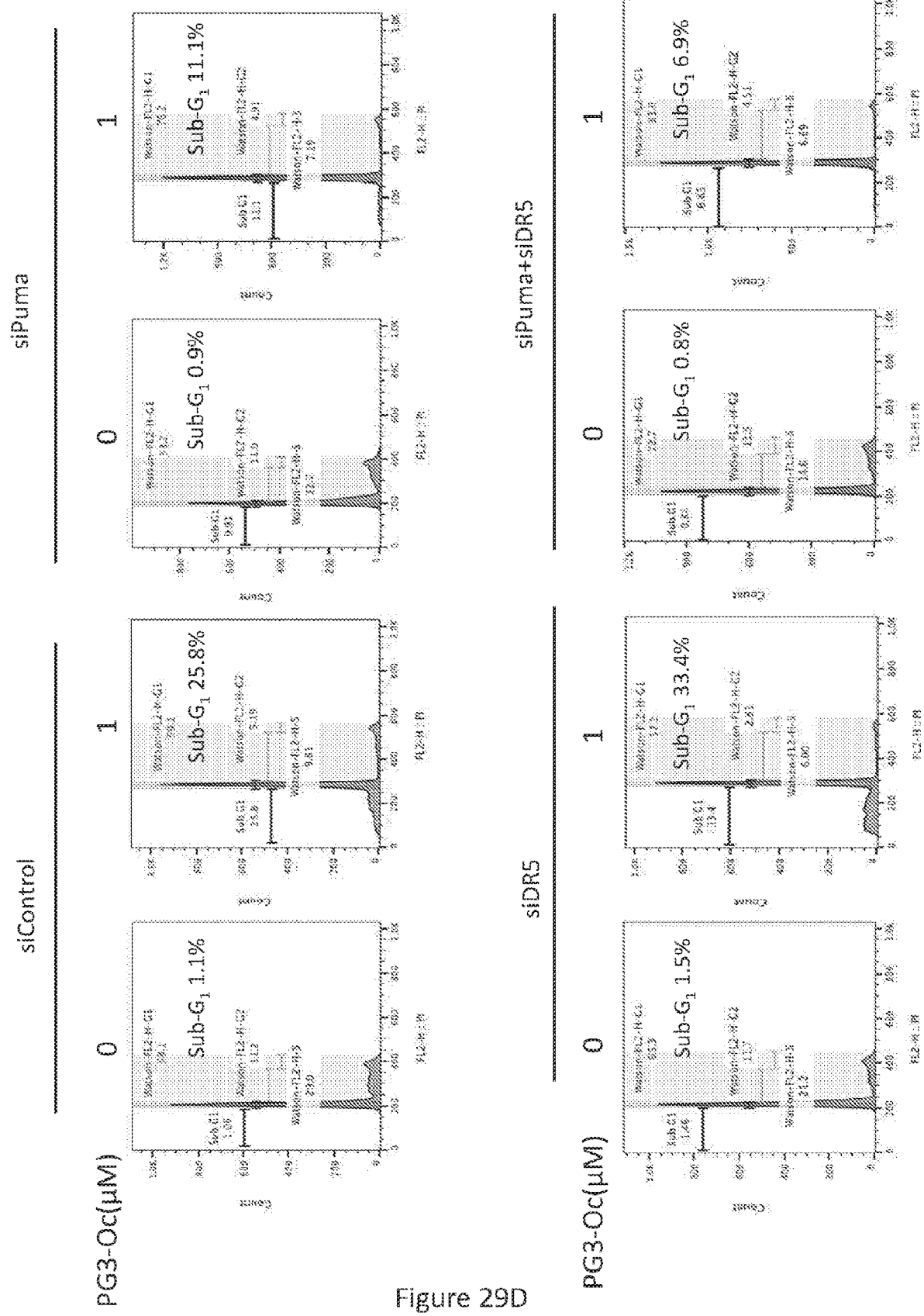
Figure 29E:
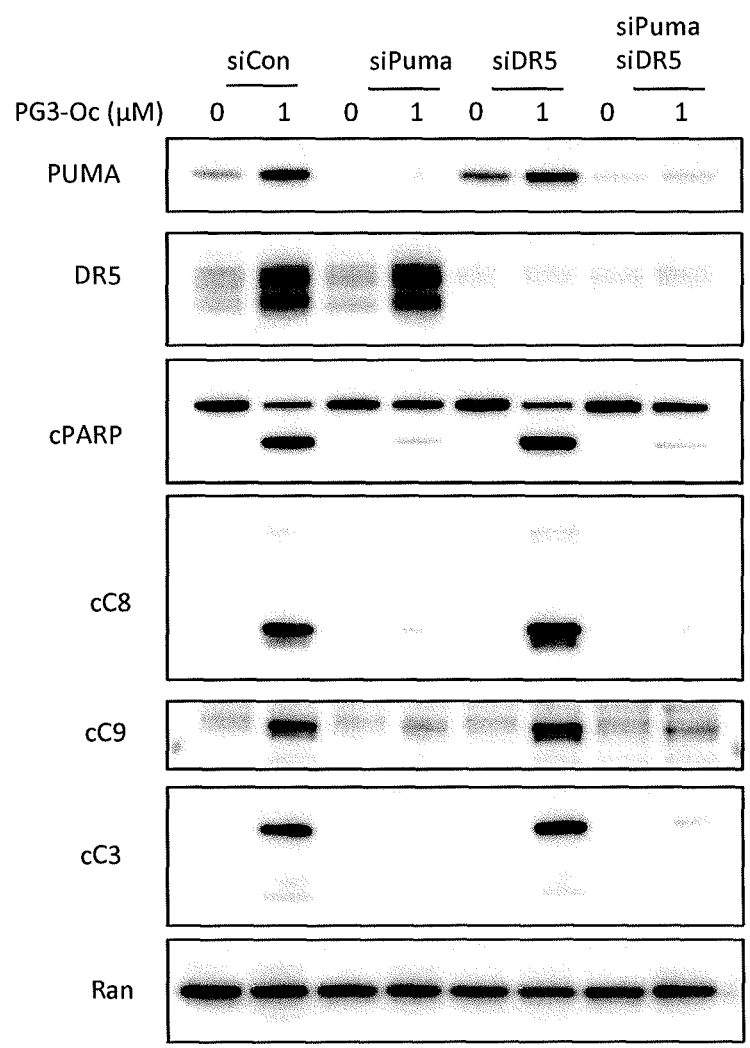

In particular, referring to FIGS. 29A-29E, the correlation of induction of PUMA with cell death is shown. FIGS. 29A, 29B, and 29C show dose-response and time-course analysis of active caspase-3, active caspase-8, active caspase-9, cleaved PARP (cPARP), Puma, and DR5 in PG3-Oc-treated HT29 cells (see, FIGS. 29A and 29B) or SW480 cells (see, FIG. 29C) by Western Blot. FIG. 29D shows HT29 cells transfected with Control, Puma, DR5 and Puma/DR5 siRNAs, after 24 hours transfection, the cells were treated with 1 μM PG3-Oc for 48 hours. After treatment, apoptosis was analyzed by nuclear PI-staining using flow cytometry. FIG. 29E shows Western blotting analysis of Puma, DR5, active caspase-8, caspase-9 caspase-3 and cleaved PARP.

PUMA siRNA studies were validated by creating PUMA gene knockout HT29 cells line via CRISPR/Cas9 gene editing technology (see, FIGS. 30A-30E). The guide was designed to target the DNA sequence that encodes amino-acid residues for the BH3-domain of PUMA (see, FIG. 30A). Knockout of the PUMA gene was found to abolish PG3-Oc-induced sub-G1 population, as well as cleavage of PARP and caspases (see, FIGS. 30F and 30G). This further indicates that binding of PUMA to anti-apoptotic Bcl-2 family members (Bcl-2, Mcl-1) may be important for PG3-Oc-mediated cell death. This may be due to disruption of the BH3-domain of PUMA and abrogation of the downstream mediators of apoptosis.

Usually activation of caspase-8 involves the extrinsic pathway of apoptosis. Of note, both knockout of the PUMA gene and knockdown of PUMA mRNAs not only abolished caspase-8 cleavage induced by PG3-Oc treatment, but also inhibited the cleavage of caspase-9, caspase-3 and PARP (see, FIGS. 29E and 30G). Further, blockage of caspase-8 by the caspase-8 inhibitor Z-IETD-FMK not only inhibited caspase 8 cleavage, but also resulted in inhibition of cleavage of caspase-9, caspase-3 and PARP. In addition, the caspase-8 inhibitor completely blocked the sub-G1 population induced by PG3-Oc treatment (see, FIGS. 30F and 30G). By contrast, the caspase-9 inhibitor Z-LEHD-FMK partially abrogated PG3-Oc-induced activation of caspase 3 and cleavage of PARP (see, FIGS. 30F and 30G). Combined treatment of caspase-8 and 9 inhibitors prevented cleavage of both caspase-3 and PARP, and reduced the sub-G1 population to the same level as untreated control cells. The pan-caspase inhibitor Z-VAD-FMK inhibited the formation of a sub-G1 population and blocked the cleavage of caspase-8, caspase-3, caspase-9 and PARP, similar to knockout of PUMA or knockdown of PUMA (see, FIGS. 30F and 30G).

Figure 30A:
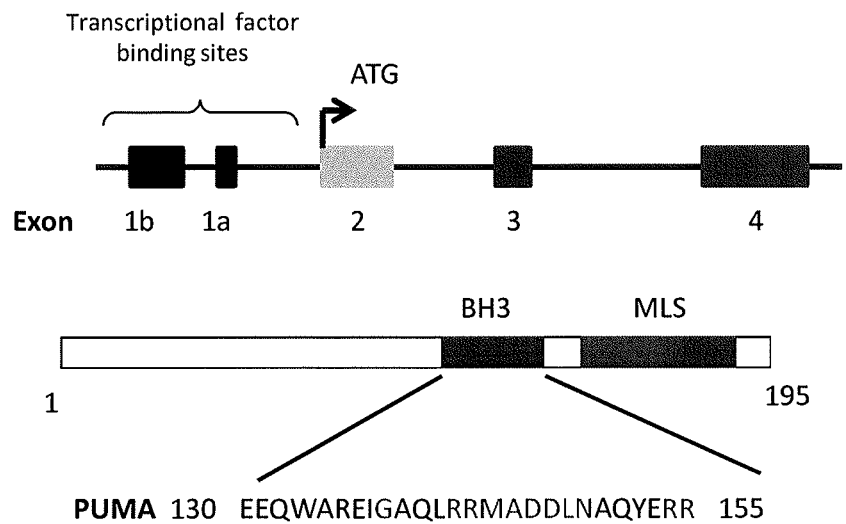
FIGS. 30A, 30B, 30C, 30D, 30E, 30F, 30G, and 30H depict that PUMA is a key effector of PG3-Oc-mediated apoptosis in mutant p53 cell lines.
Figure 30B:
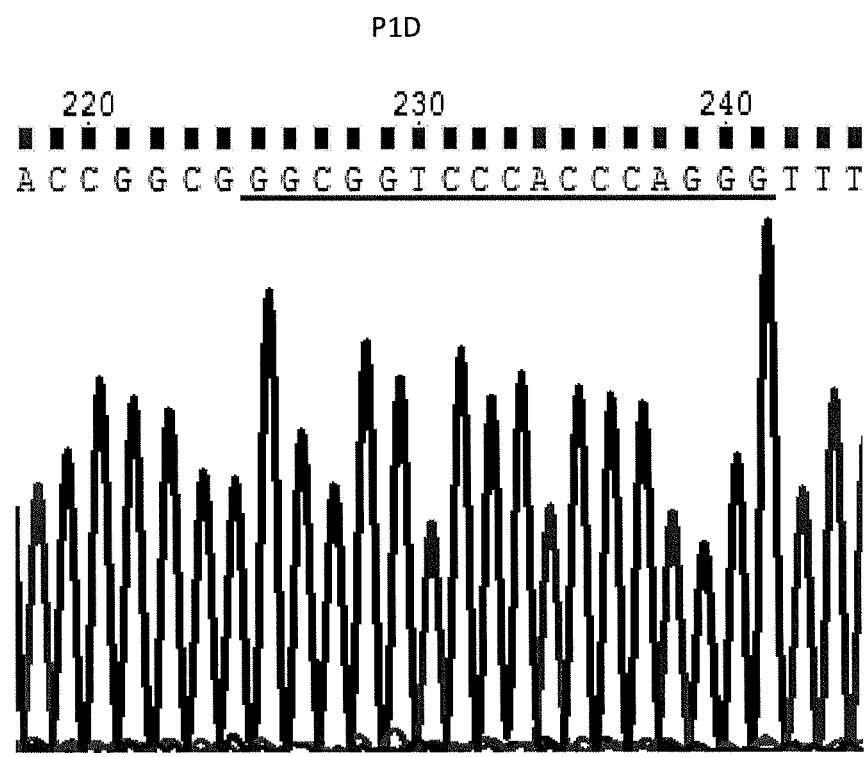
Figure 30C:
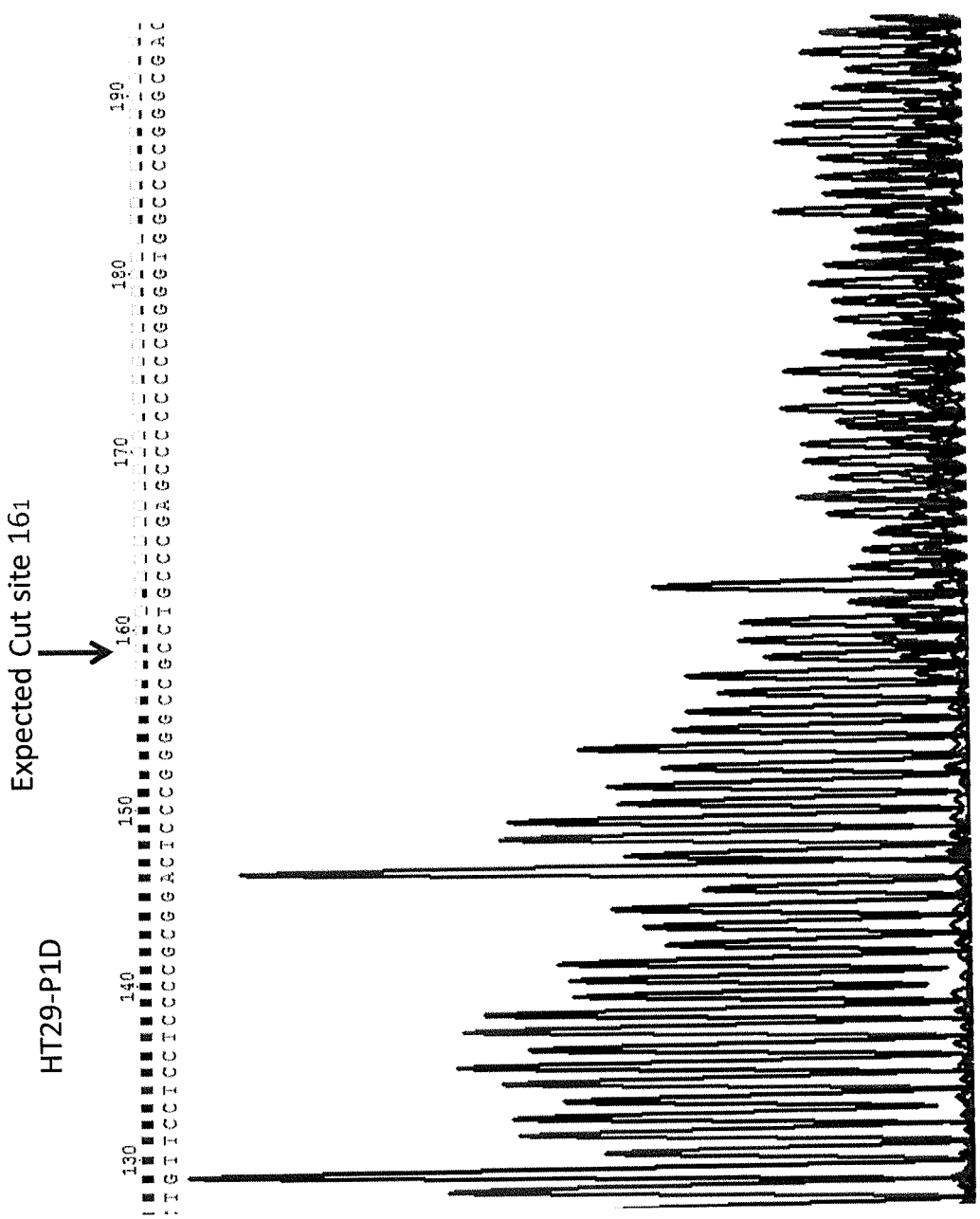
Figure 30D:
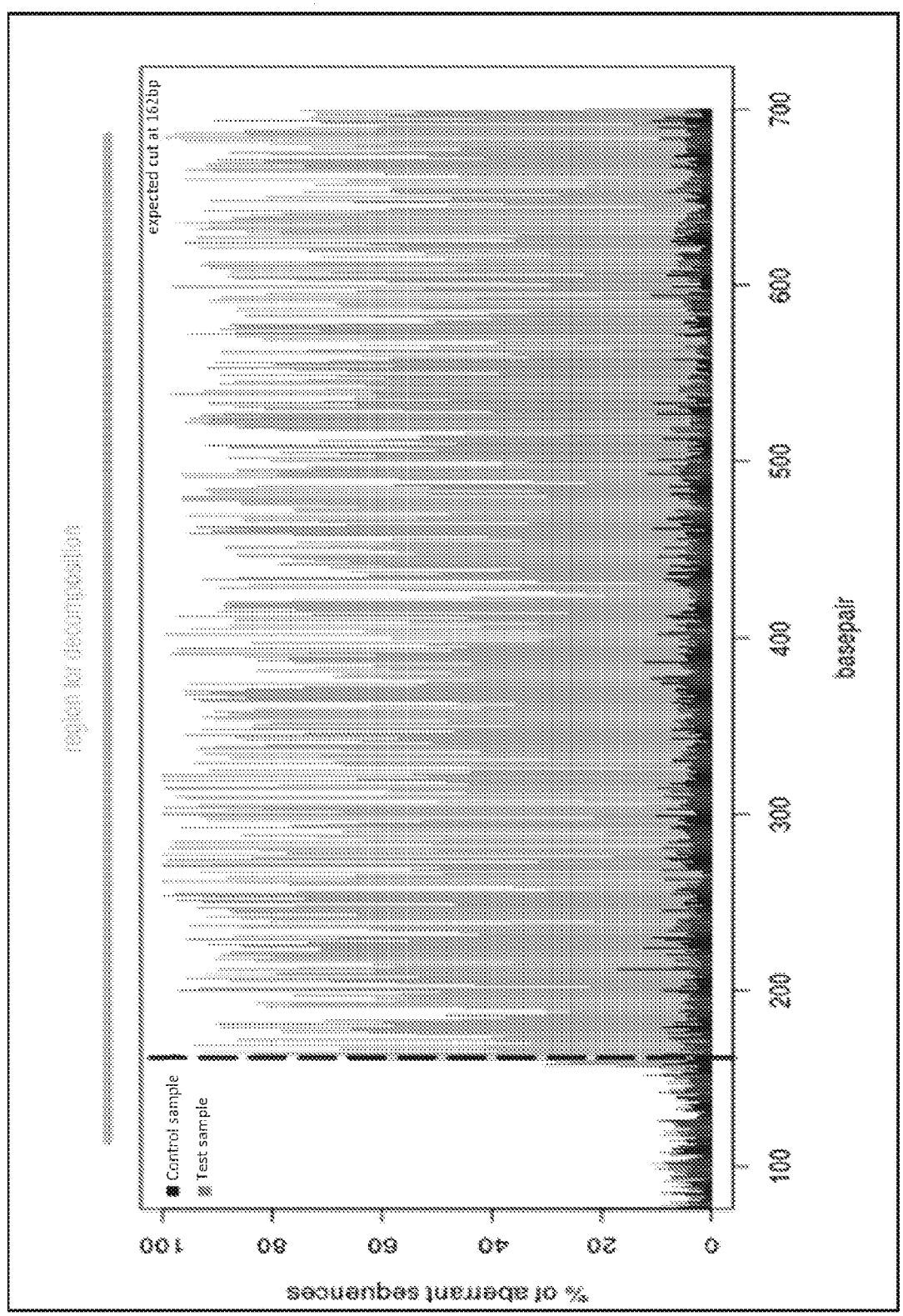
Figure 30E:
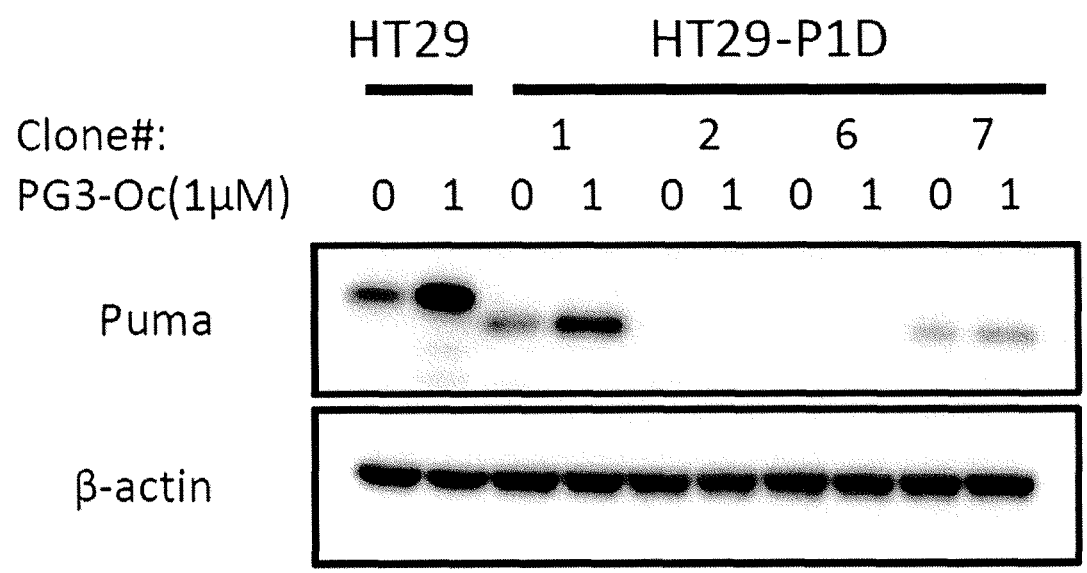
Figure 30F:
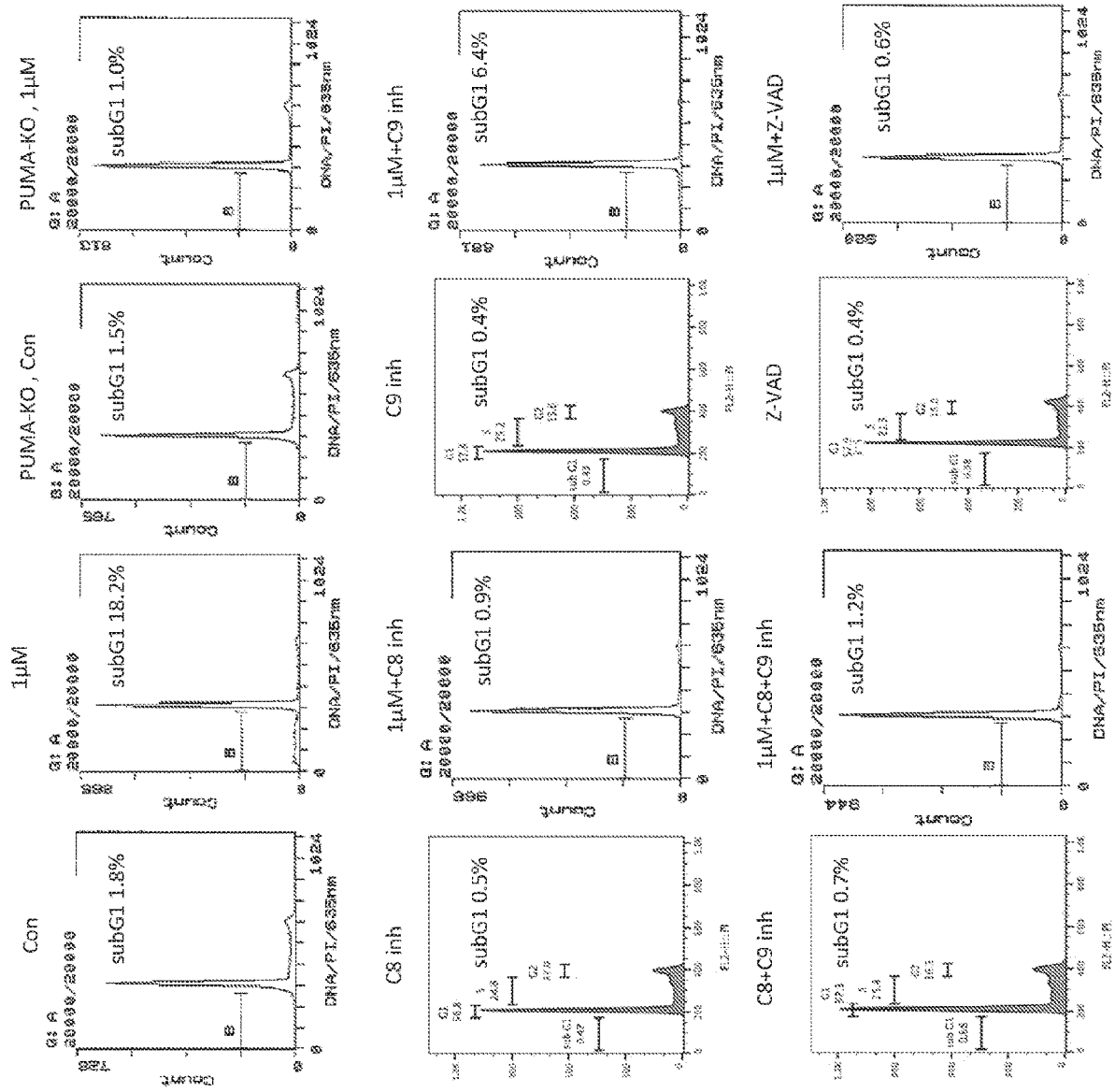
Figure 30G:
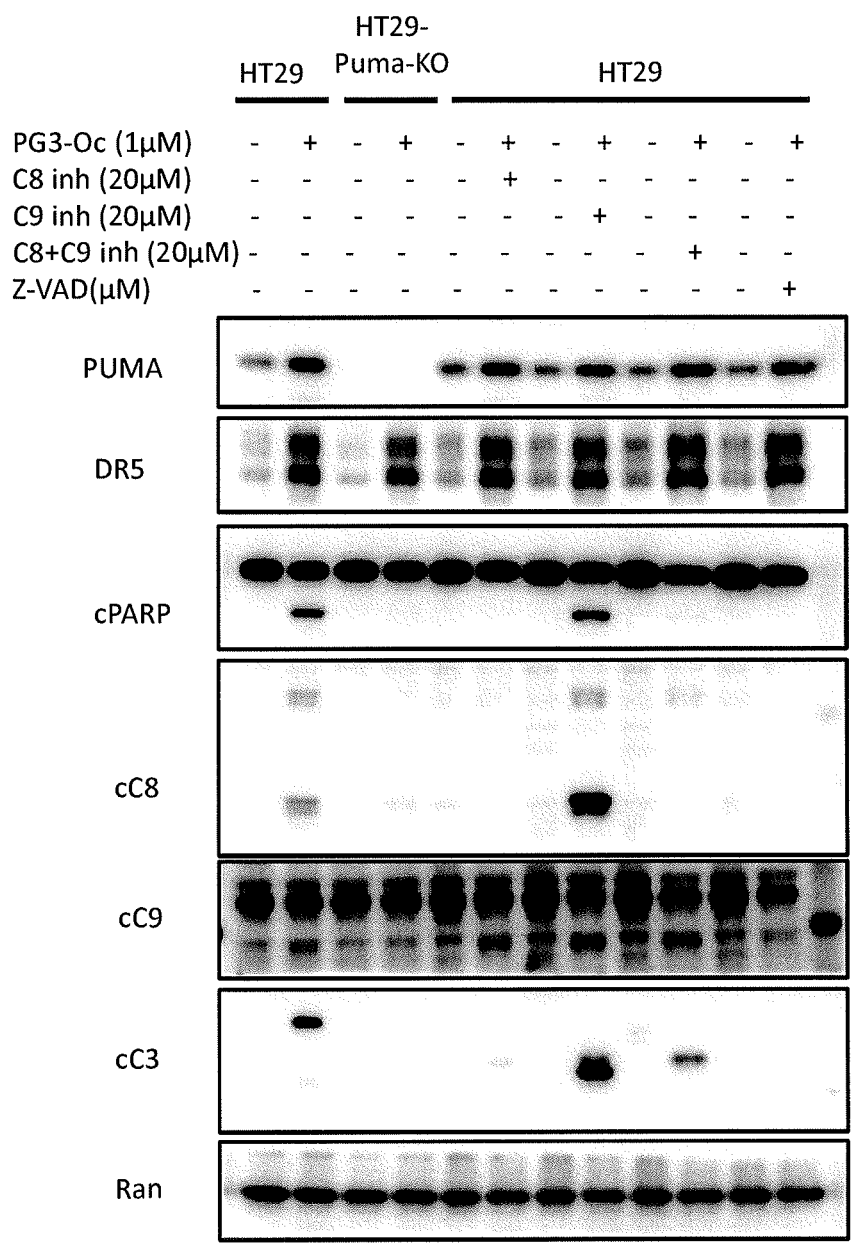
Figure 30H:
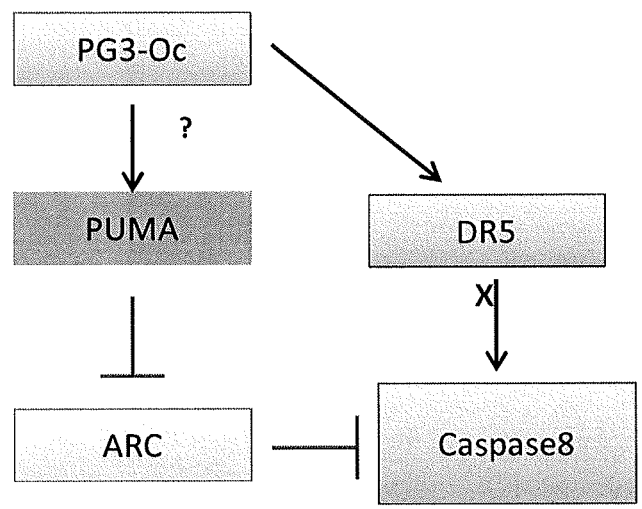

In particular, referring to FIGS. 30A-30H, it is shown that PUMA is a key effector of PG3-Oc mediated apoptosis in mutant p53 cell lines. FIG. 30A shows the human PUMA gene contains three coding exons (exons-2-4) and two non-coding exons (exons 1a and 1b). PUMA protein has two functional domains, the BH3 and C-terminal mitochondria-localization signal (MLS). The red-colored residues are conserved within other proapoptotic Bcl-2 family members. FIG. 30B shows sequencing result of guide 1-containing plasmid P1D. FIG. 30C shows DNA sequencing results of HT29-P1D, which are pools of lentivirus-infected and puromycin-selected cells. FIG. 30D shows the decomposition window of TIDE analysis for HT29-P1D. FIG. 30E shows Western blotting analysis of the express of PUMA protein from single cell colonies of HT29-P1D cells. FIG. 30F shows HT29 and HT29-Puma-KO cells were treated with PG3-Oc or co-treated with caspase 8 (cas8 inh), caspase-9 (cas9 inh) and pan-caspase (Z-VAD-FMK) inhibitors for 48 hours, subG1 populations were analyzed by flow cytometry. FIG. 30G shows the activation of caspases and PARP cleavage were detected by western blotting using indicated antibodies. FIG. 30H shows a model for PUMA mediated activation of caspase-8.

Taken together, these data indicate that caspase-8 cleavage is an up-stream event of the activation of caspase-9 and caspase-3, and that PUMA mediates the apoptotic effects of PG3-Oc through activation caspase-8.

5) The Molecular Mechanism of PG3-Oc-Induced Up-Regulation of PUMA May Involve the UPR:

The molecular mechanisms responsible for up-regulation of p53 target genes by PG3-Oc in p53 mutant colorectal cancer cells was investigated. Transcription factors p73, p63, ATF4, CHOP, FOXO3a, NF-κB, and JNK/c-Jun can mediate induction of PUMA in a p53-independent manner depending on cell types and stimuli.

Figure 31A:
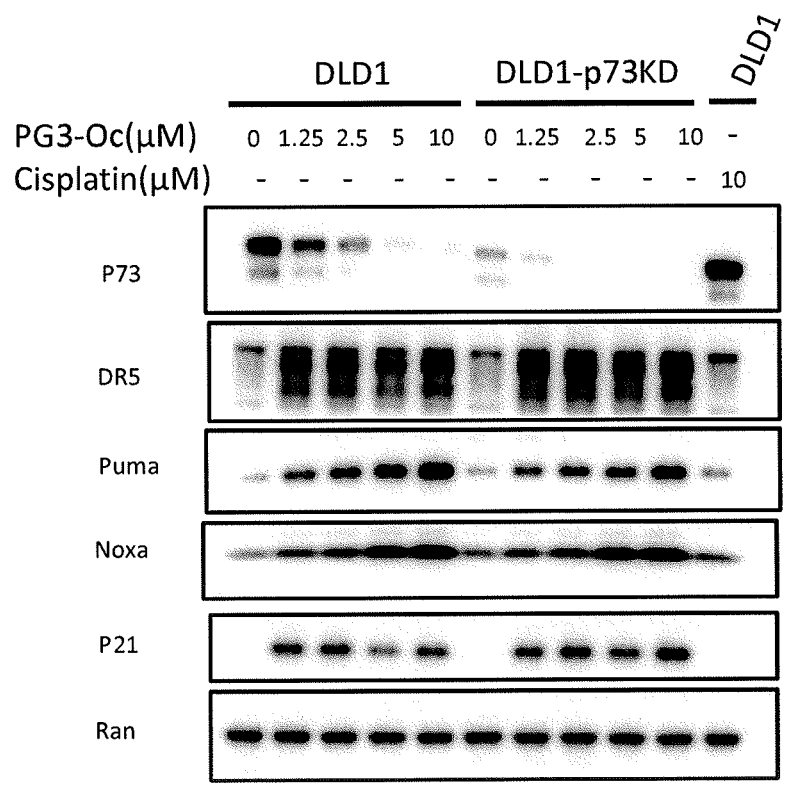
FIGS. 31A, 31B, 31C, 31D, and 31E depict the exploration of the molecular mechanism of PG3-Oc-induced up-regulation of PUMA.
Figure 31B:
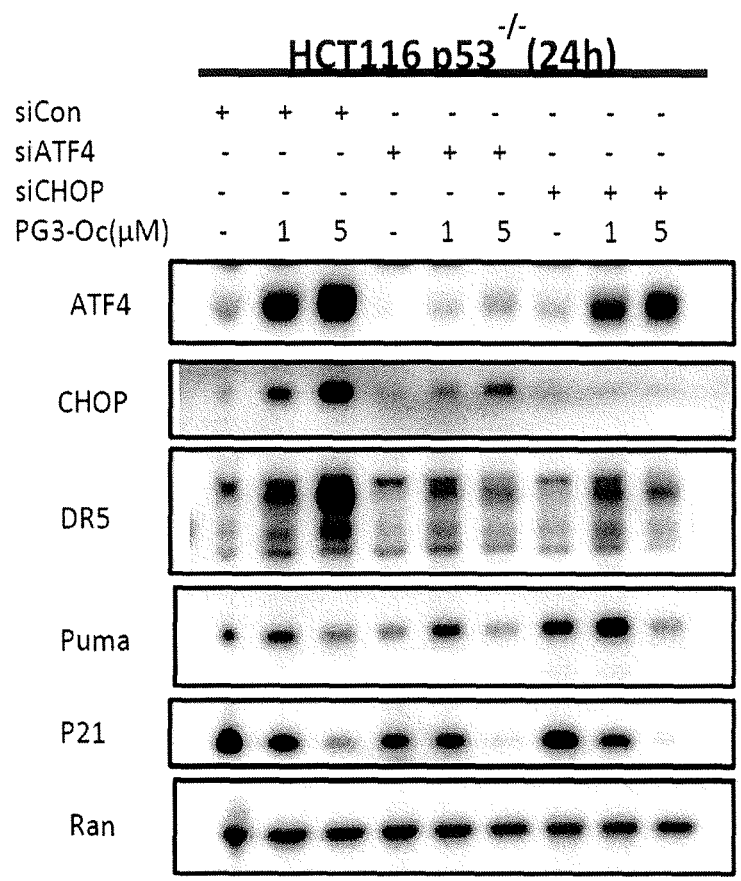
Figure 31C:
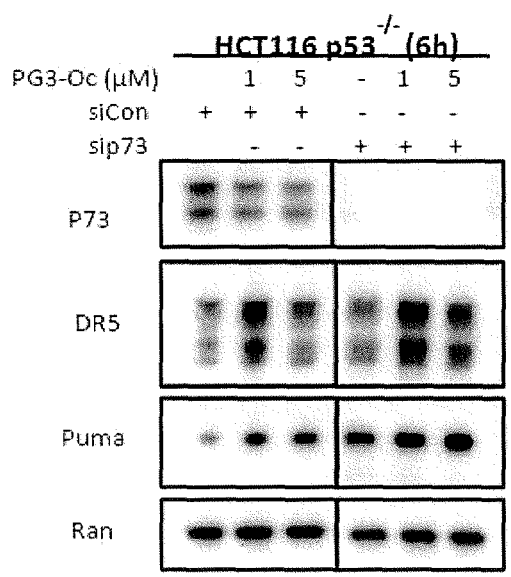
Figure 32A:
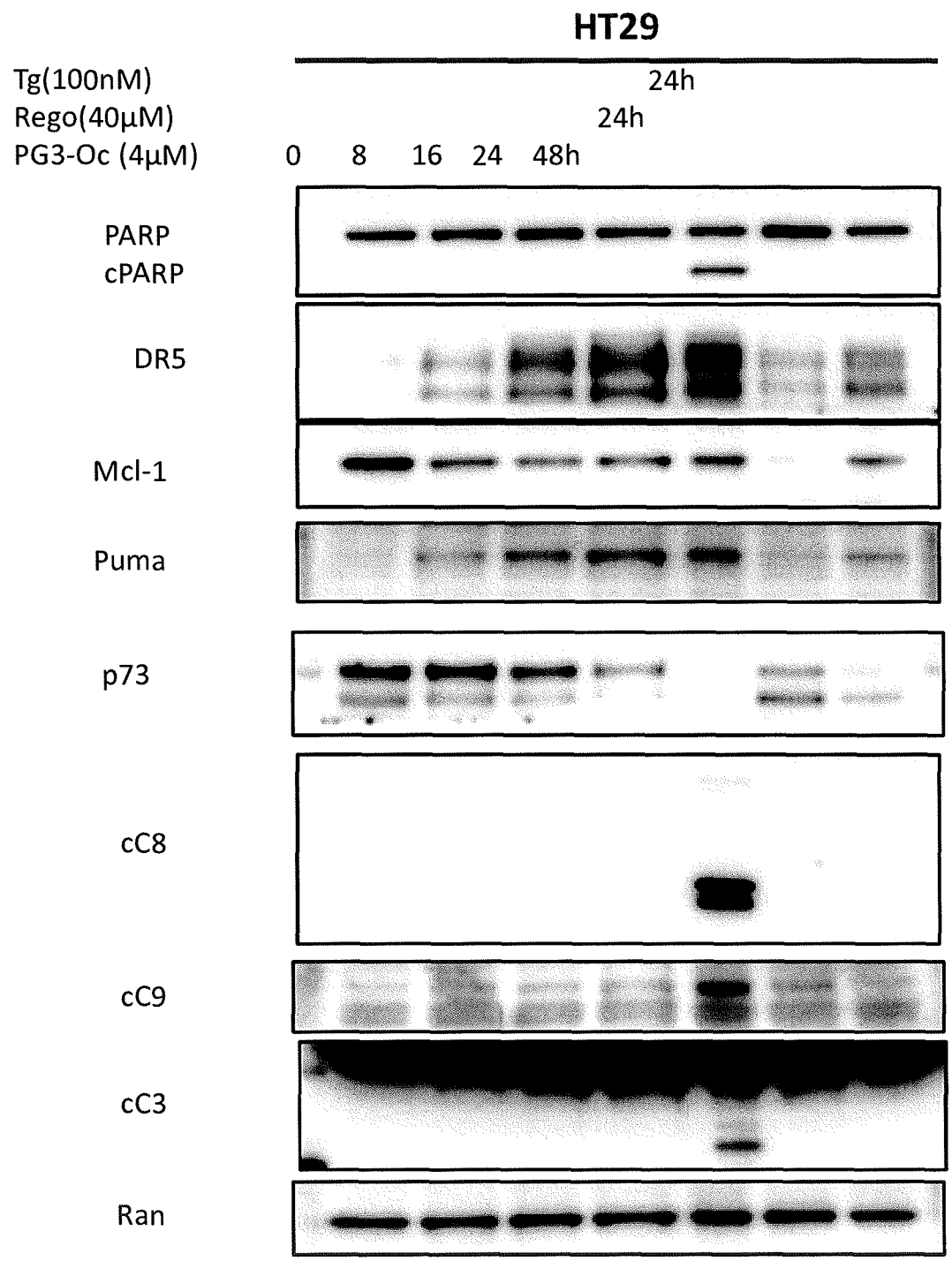
FIGS. 32A and 32B depict time-course analysis of caspase activation.
Figure 32B:
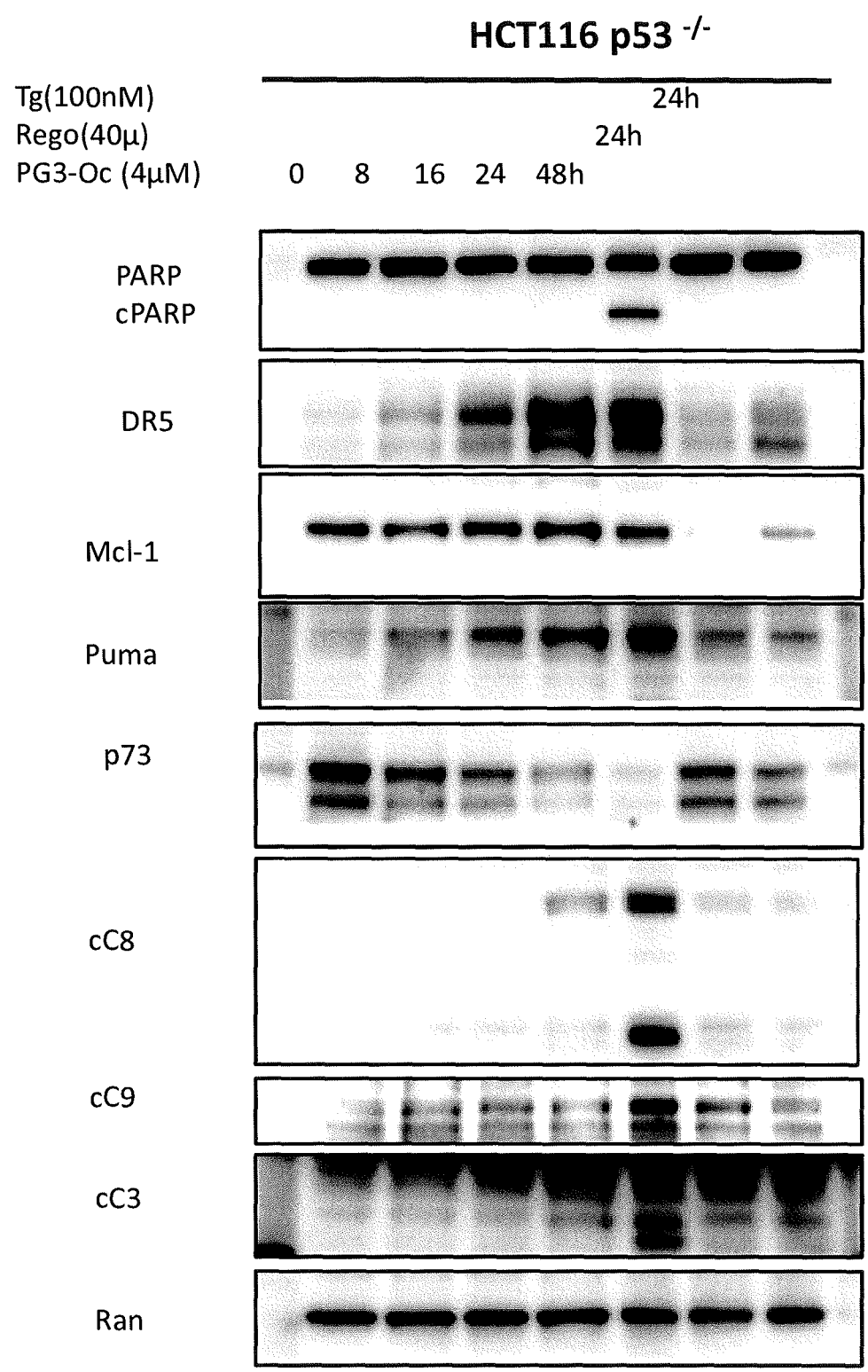

PG3-Oc treatment resulted in a decrease of p73 protein in DLD1, HCT116 p53$^{-/-}$ (see, FIGS. 31A and 31C), SW480 and HT29 (FIGS. 32A and 32B). Knockdown of p73 did not affect PG3-Oc-induced up-regulation of p53 target genes, DR5, p21, Noxa and PUMA (see, FIGS. 31A and 31C). These data indicate that p73 is not involved in PG3-Oc-induced up-regulation of these p53 target genes in these colorectal cancer cell lines.

In particular, referring to FIGS. 32A and 32B, the time-course analysis of active caspase-3, active caspase-8, active caspase-9, cleaved PARP(cPARP), Puma, and DR5 in PG3-Oc-treated HT29 cells (see, FIG. 32A) or HCT116 p53$^{-/-}$ cells (see, FIG. 32B) by Western Blot. Regorafenib (Rego) is a positive control for Puma, and thapsigargin (Tg) is a positive control for DR5.

Figure 33A:
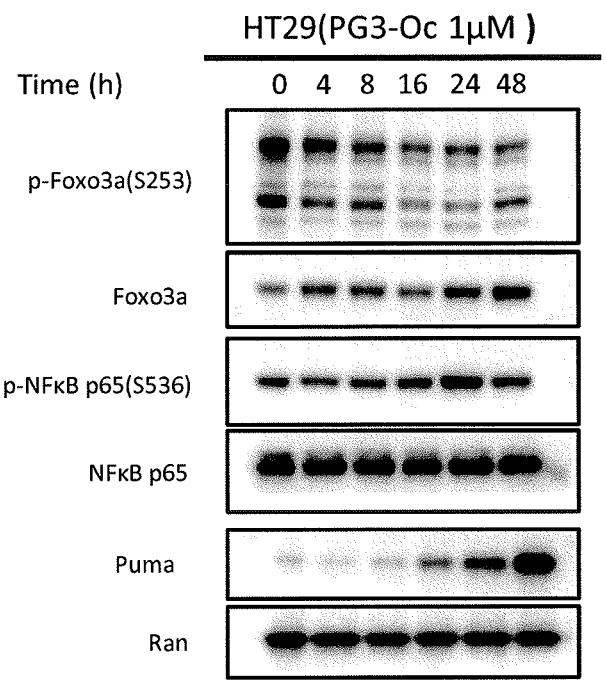
FIGS. 33A, 33B, 33C, and 33D depict the exploration of the molecular mechanism of PG3-Oc-induced up-regulation of PUMA.
Figure 33B:
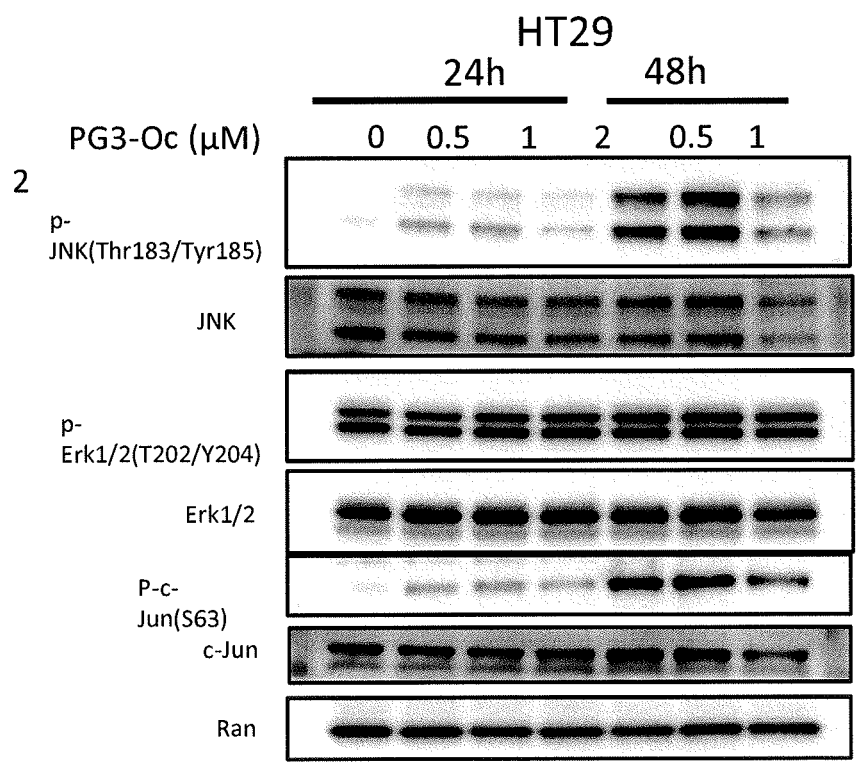
Figures 33C, 33D:
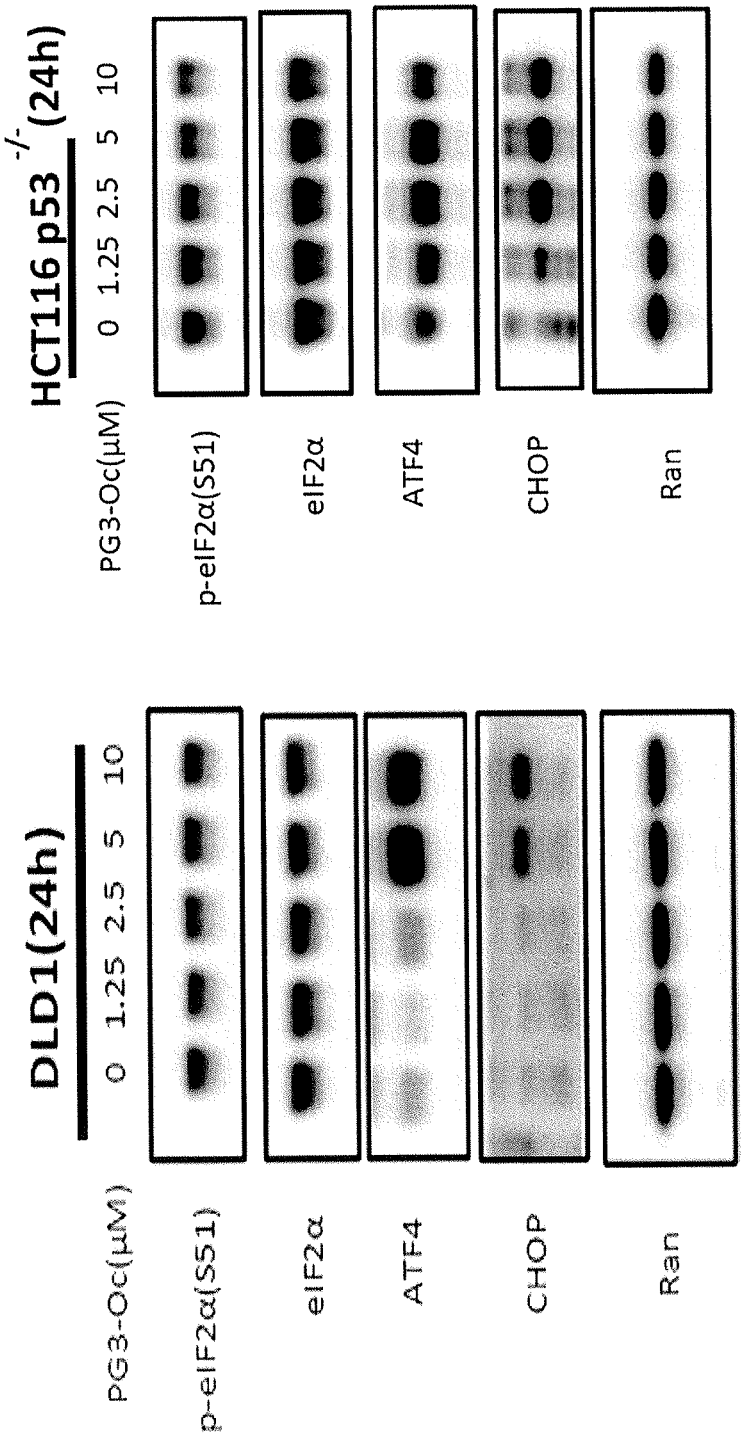

PG3-Oc treatment resulted in up-regulation of ATF4 and CHOP in both DLD1 and HCT116 p53$^{-/-}$ cell lines. However, induction of ATF4 and CHOP occurred at a significantly lower concentration in HCT116 p53$^{-/-}$ cells at 1.25 µM as compared to 5 µM in DLD1 cells (see, FIGS. 33C and 33D). HCT116 p53$^{-/-}$ cells were selected for studying whether ATF4 and/or CHOP may be responsible for PUMA up-regulation. Knockdown of ATF4 or CHOP by siRNAs, respectively, did not blunt up-regulation of PUMA and p21, but blocked the up-regulation of DR5. These data indicate that ATF4 and CHOP are not involved in regulation of PUMA and p21, but may be responsible for DR5 induction (see, FIG. 31B), indicating that PG3-Oc treatment may trigger the UPR signaling pathway.

Figures 31D, 31E:
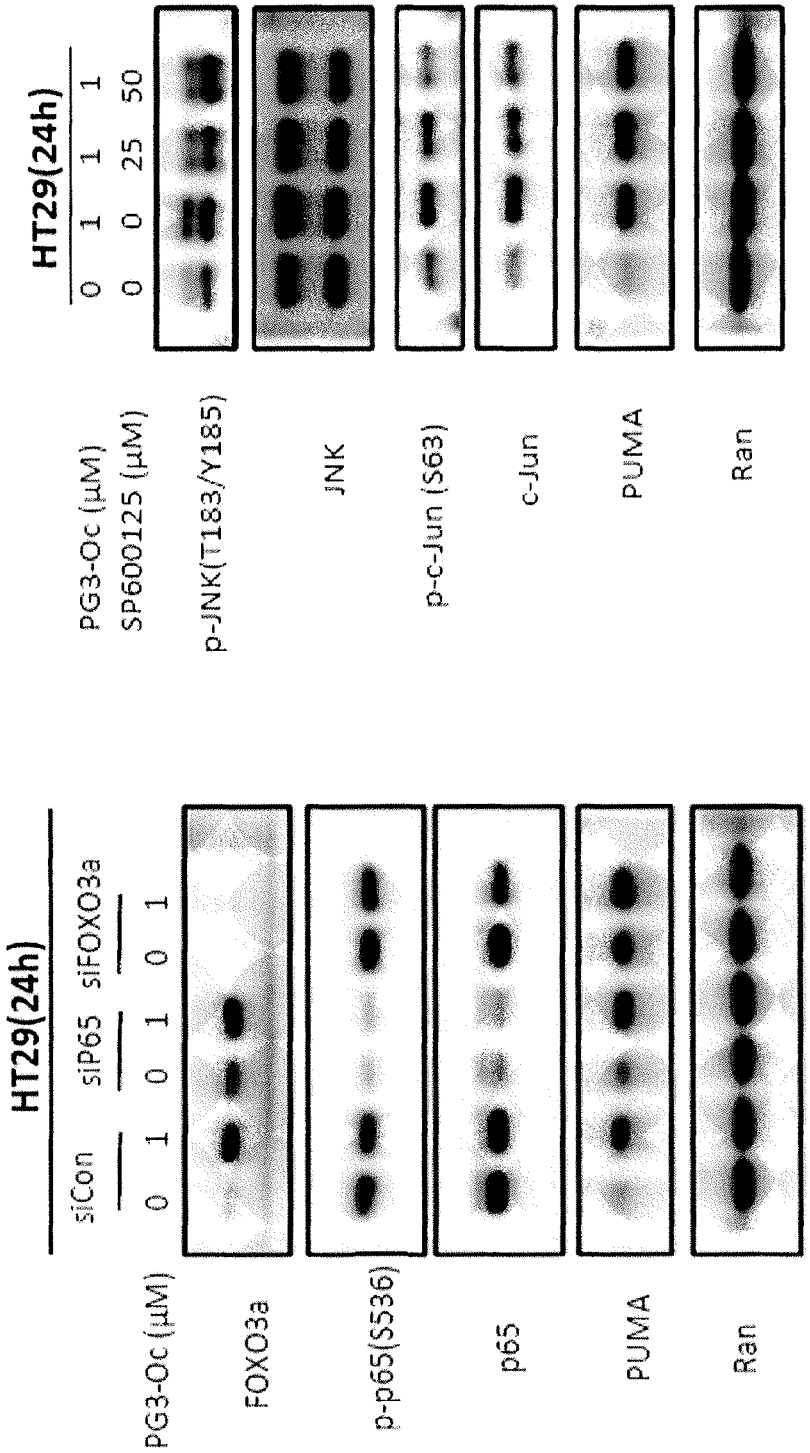

PG3-Oc treatment leads to decreased phosphorylation of Ser-253 of FOXO3a, increased phosphorylation of Ser-536 of NF-κB p56 and phosphorylation of JNK and c-Jun (see, FIGS. 33A and 33B); however, knockdown of FOXO3a and NF-κB p56, inhibition of JNK by JNK inhibitor SP600125 did not abolish up-regulation of PUMA (see, FIGS. 31D and 31E). These data indicate that NF-κB, FOXO3a and JNK/c-Jun do not involved in the regulation of Puma.

In particular, referring to FIGS. 33A-33D, the exploration of the molecular mechanism of PG3-Oc-induced up-regulation of PUMA is shown. HT29 cells were treated with indicated doses and time points, phosphorylation of FOXO3a, NF-κB, JNK, c-Jun and Erk1/2 were detected by Weston blotting using corresponding antibodies.

In particular, referring to FIGS. 31A-31E, the exploration of the molecular mechanism of PG3-Oc-induced up-regulation of PUMA is shown. FIG. 31A shows p53 mutant DLD1(S241F) and p73 stable-knockdown DLD1-p73KD were treated with indicated concentration of PG3-Oc for 18 hours, Cisplatin was used as a positive control for p73. FIG. 31B shows HCT116 p53$^{-/-}$ cells were transfected with ATF4 or CHOP siRNAs, after 24 hours transfection the cells were treated with PG3-Oc for 24 hours. Protein levels of p53 target genes in cells were detected by Western Blot. FIG. 31C shows HCT116 p53$^{-/-}$ cells were transfected with p73 siRNA, after 24 hours transfection the cells were treated with PG3-Oc for 6 hours. Protein levels of p53 target genes in cells after PG3-Oc treatment were detected by Western Blot. Knockdown of p73 does not prevent PG3-Oc-induced expression of p53-target genes. FIG. 31D shows HT29 cells were transfected with Control, NF-κB and FOXO3a siRNAs respectively. After 24 hours of transfection, the cells were treated with 1 µM PG3-Oc for 24 hours and protein levels in cells were detected by Western Blot. FIG. 31E shows T29 cells were pre-treated for 1 hour with JNK inhibitor SP600125, and then treated with 1 µM PG3-Oc for 24 hours. Protein levels in cells were detected by western blot using indicated antibodies.

Figure 34A:
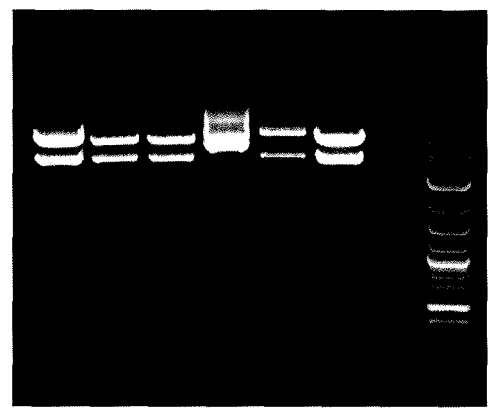
FIGS. 34A, 34B, 34C, 34D, 34E, 34F, 34G, 34H, and 34I depict knock-out of PUMA by CRISPR/Cas9 gene editing.
Figure 34B:
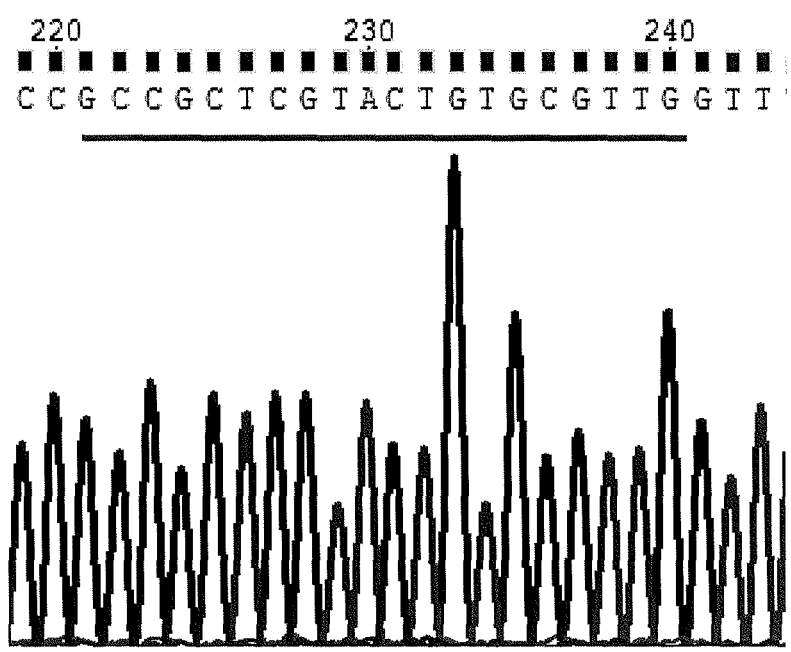
Figure 34C:
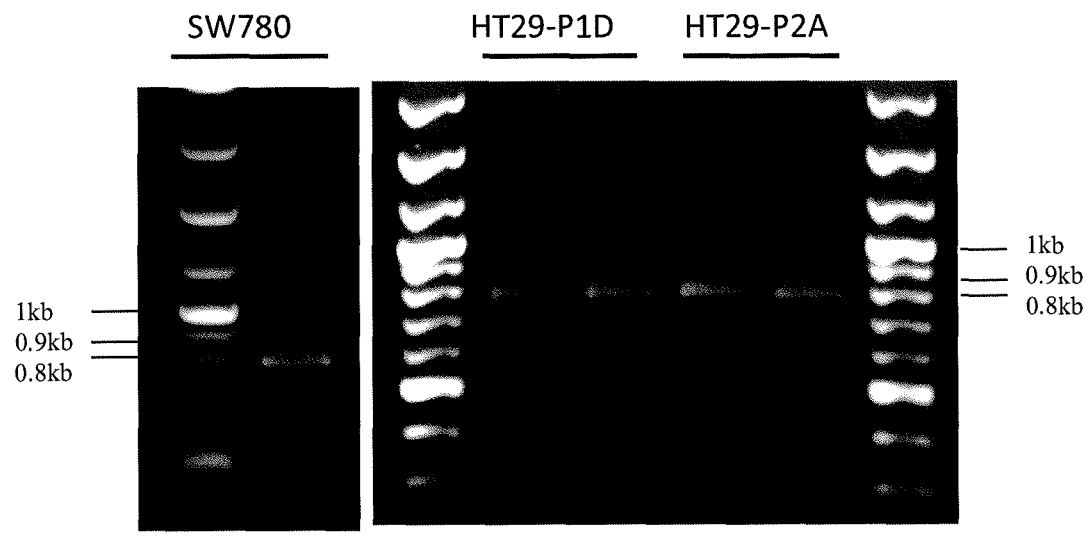
Figure 34D:
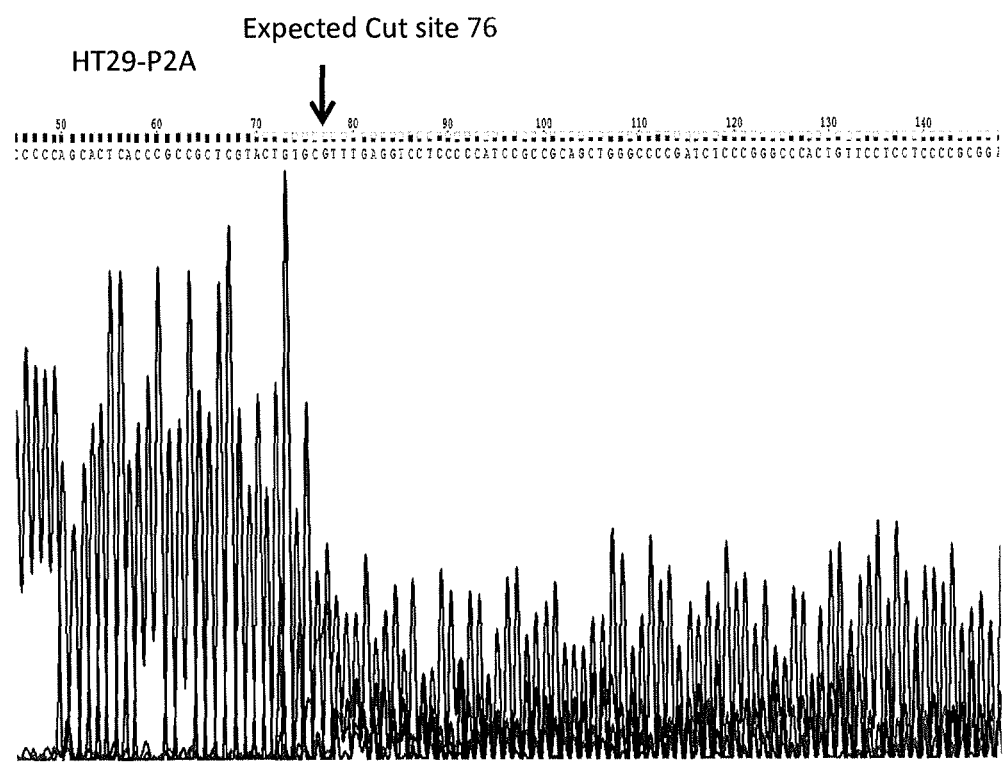
Figure 34E:
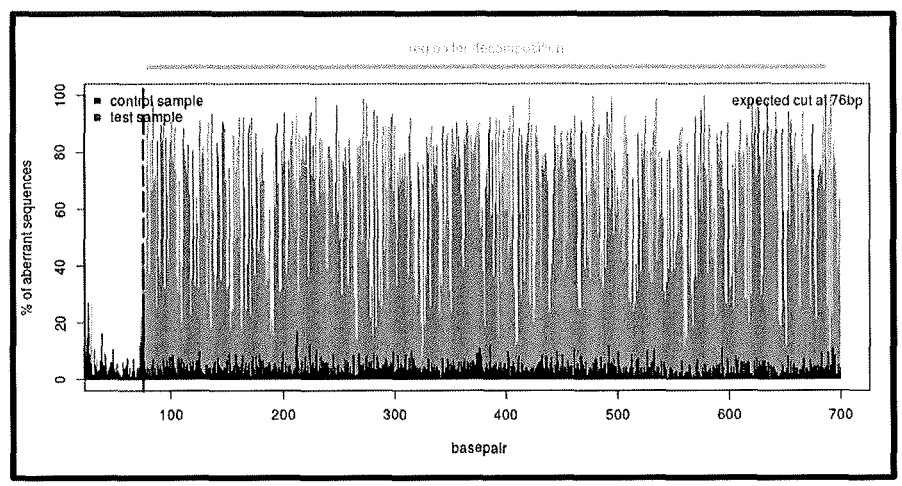
Figure 34F:
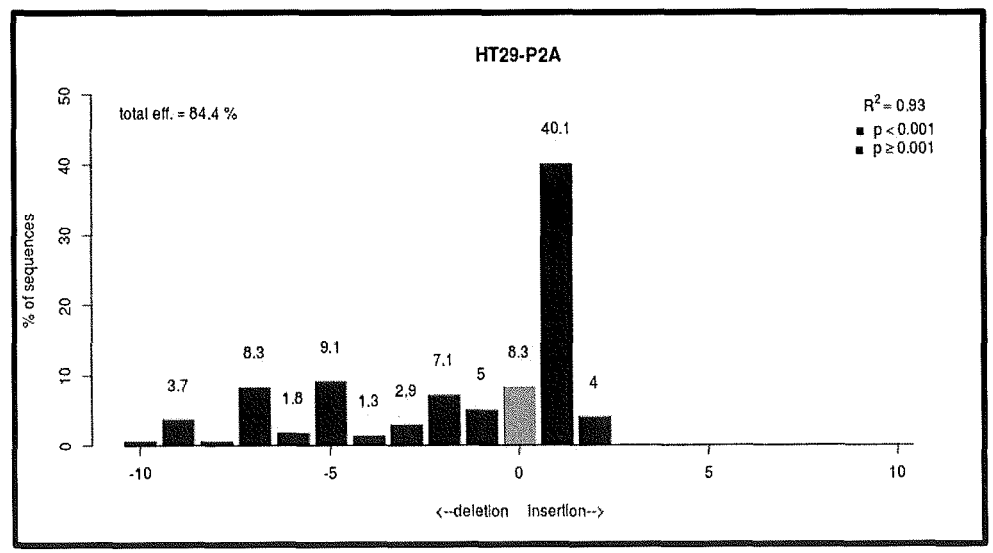
Figure 34G:
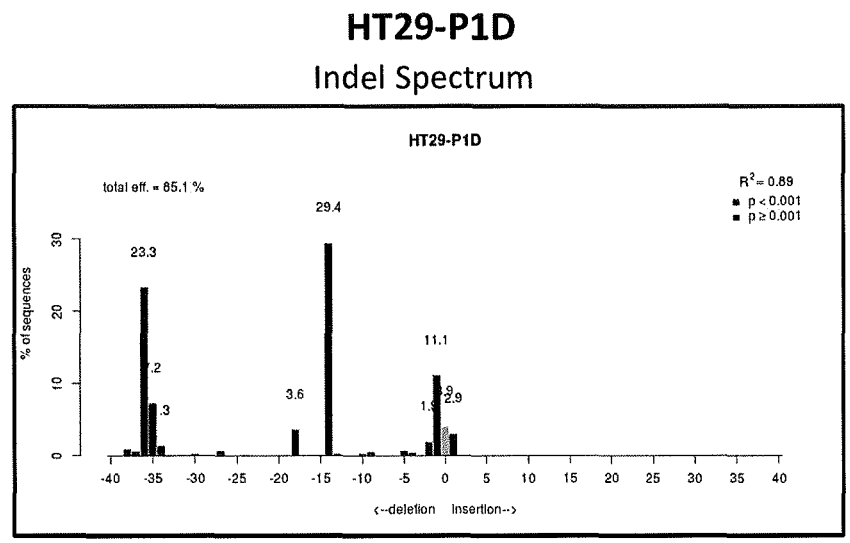
Figure 34H:
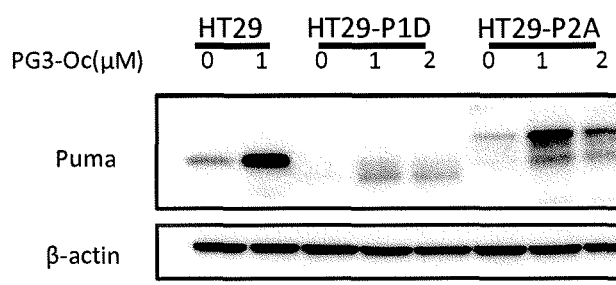
Figure 34I:
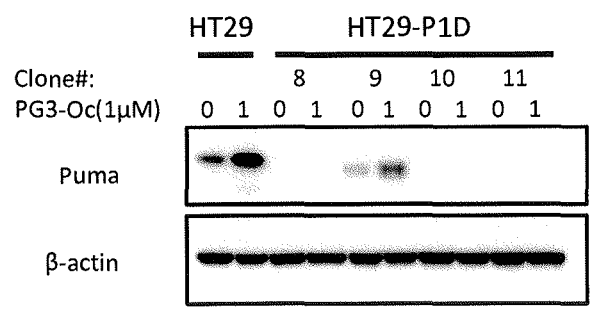

In particular, referring to FIGS. 34A-34I, the knock-out of PUMA by CRISPR/Cas9 gene editing is shown. FIG. 34A shows P1A, P1D, P2A and P2B are plasmids containing guide 1 or guide 2 purified from corresponding bacteria colonies (P1A, P1D, P2A and P2B), respectively. Plcve is a negative control plasmid, and KDM6A is a positive control plasmid. FIG. 34B shows sequence of guide 2 and sequencing result of guide 2-containing plasmid P2A. FIG. 34C shows PCR results of HT29-P1D, HT29-P2A and SW780 (wild-type DNA) using primers that cover the exon 3 of PUMA gene. FIG. 34D shows DNA sequencing results of HT29-P2A, which is a pool of lentivirus-infected and puromycin-selected cells. FIG. 34E shows the decomposition window and indel spectrum of TIDE analysis for HT29-P2A. FIG. 34F shows indel spectrum of TIDE analysis for HT29-P2A. FIG. 34G shows indel spectrum of TIDE analysis for HT29-P1D. FIG. 34H shows Western blotting analysis of the express of PUMA protein in HT29-P1D and HT29-P2A cells. FIG. 34I shows Western blotting analysis of the express of PUMA protein from single cell colonies of HT29-P1D cells.

Discussion:

Apoptosis repressor with caspase recruitment domain (ARC) is an endogenous inhibitor of apoptosis which binds and suppresses caspase-8. Expression of ARC protein is predominantly seen in terminally differentiated cells (cardiac, skeletal myocytes and neurons) under normal conditions and is markedly induced in a variety of cancers including pancreatic, colorectal, breast, lung, glioblastoma, liver, kidney, melanoma, and acute myeloid leukemia. ARC is a primary target of p53, and p53 transcriptionally represses the express of ARC, which can initiate apoptosis. Phosphorylation of ARC at T149 by CK2 (casein kinase 2) leads to ARC translocation from cytosol to mitochondria where it binds to death domain of caspase-8 and inhibits caspase-8 activation. PUMA localizes in mitochondria and induces apoptosis by activating caspases via activating BAK and BAX to cause mitochondrial dysfunction. ARC binds to caspase-8 death domain through its N-terminal CARD (caspase recruitment domain) domain. PUMA via its BH3 domain binds to the CARD domain of ARC tightly, resulting in releasing of caspase-8 from ARC, and then activation of caspase-8. Vice versa, up-regulation of ARC protein level in cancer cells can suppress PUMA-mediated caspase activation and apoptosis by sequestering PUMA and releasing anti-apoptotic Bcl-2 family members. Based on the data, a model of PG3-Oc-induced and PUMA-mediated apoptosis in colorectal cancer cells is disclosed in FIG. 30H.

The results indicate that a prodigiosin analog, PG3-Oc, has comparable efficacy as obatoclax and prodigiosin in p53 mutant cancer cell lines. PG3-Oc is a more potent inducer than prodigiosin in restoration of the p53 signaling pathway.

Example 3: Synthesis of PG3-Oc (Formula (IXd))

Figure 35:
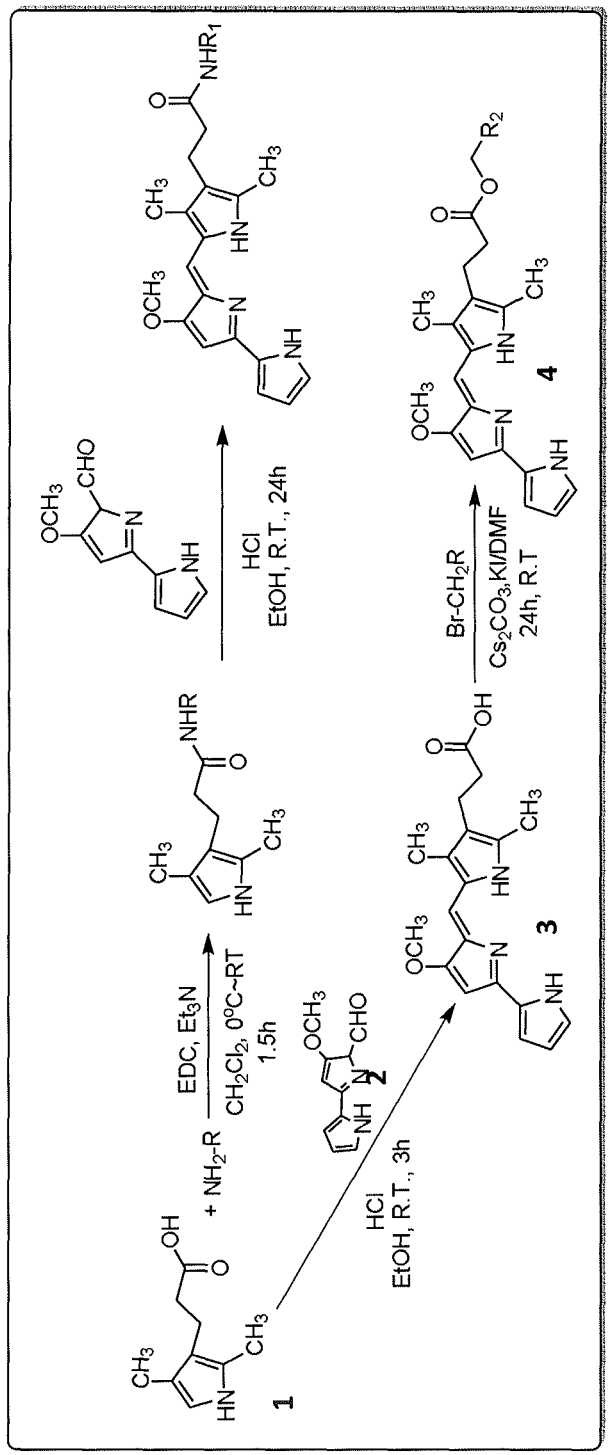
FIG. 35 depicts a representative synthetic scheme for PG3-Oc.

A representative synthesis of PG3-Oc and related compounds is shown in FIG. 35.

Figure 36:
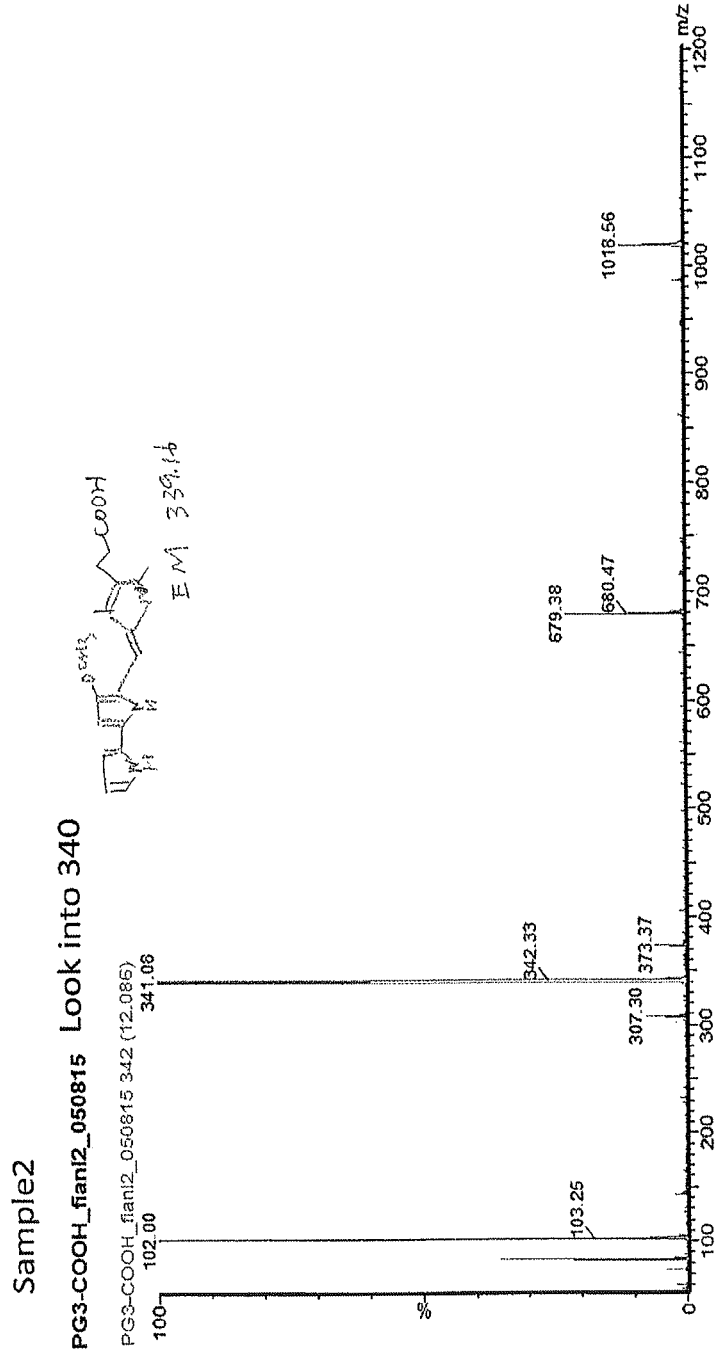
FIG. 36 depicts Mass spectrum analysis of Compound 3 in FIG. 35.
Figure 37:
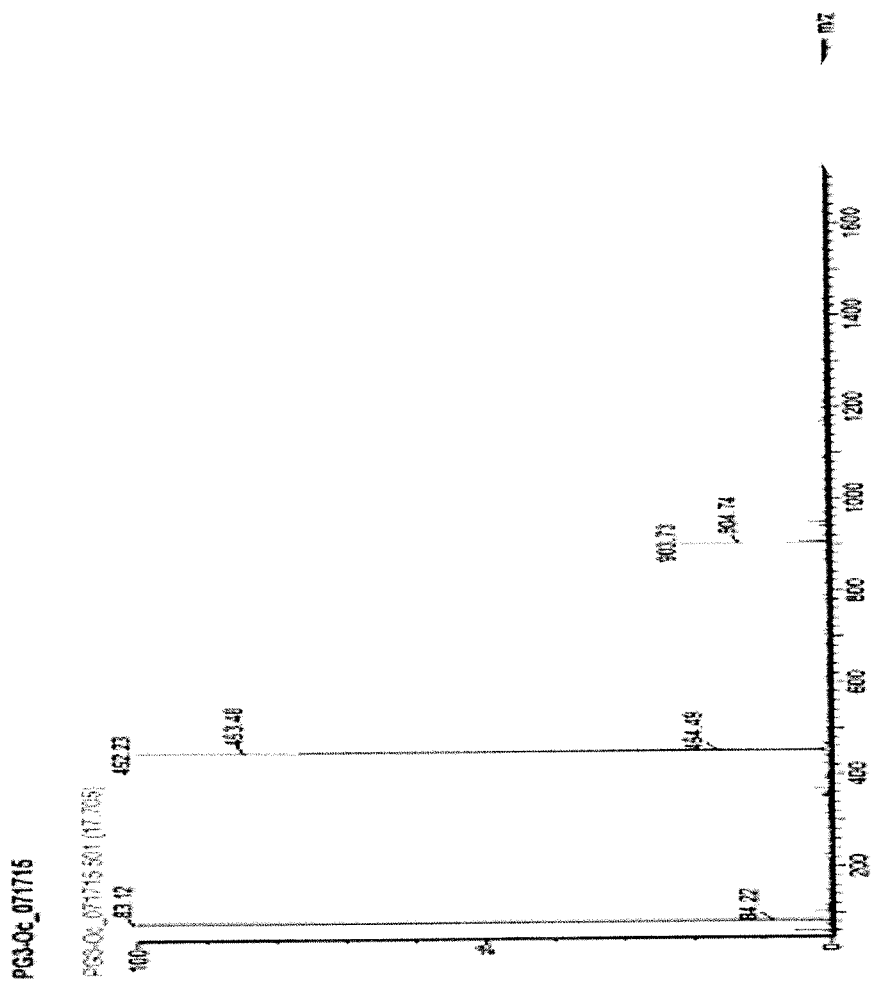
FIG. 37 depicts Mass spectrum analysis of PG3-Oc.
Figure 38:
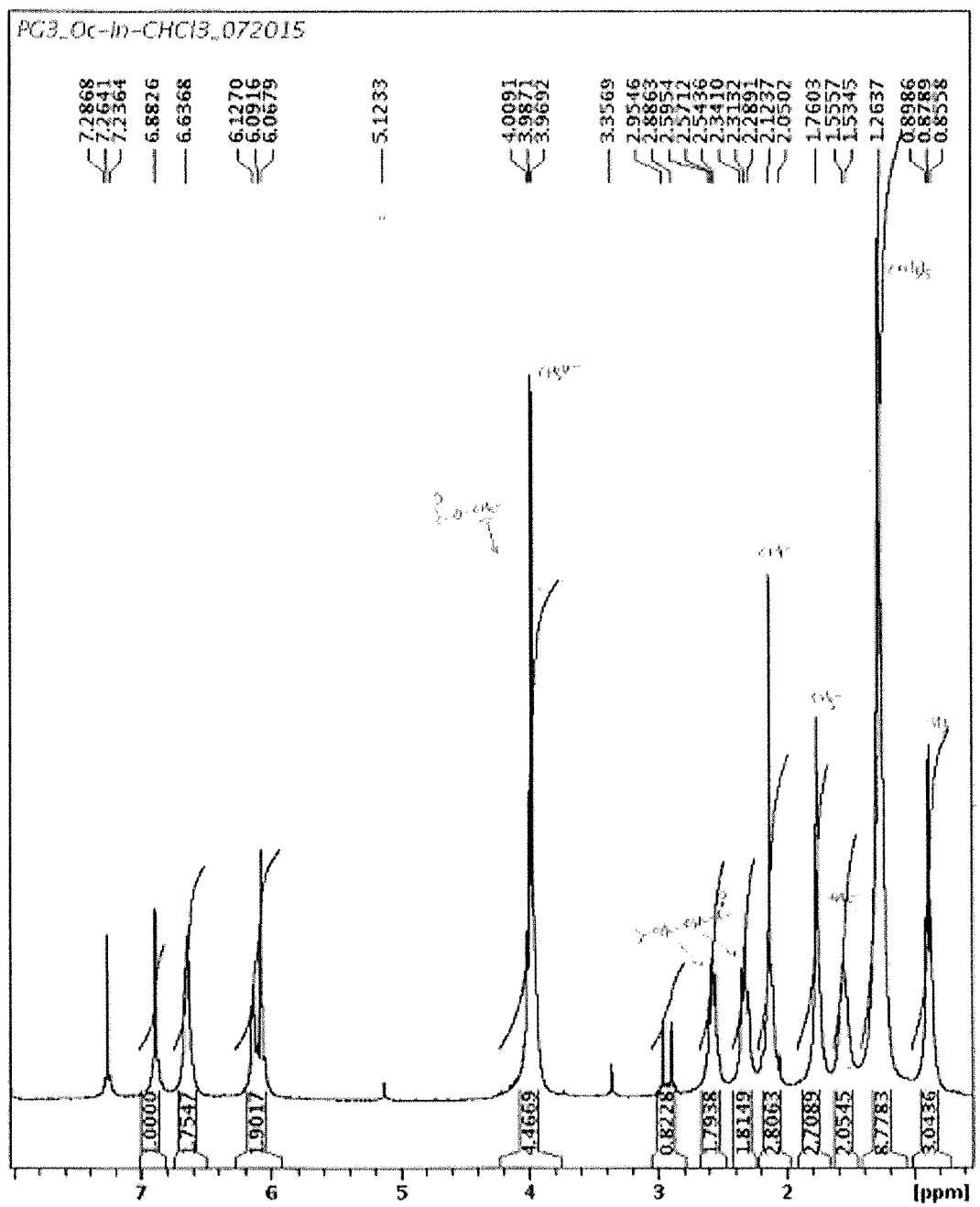
FIG. 38 depicts $^1$H NMR analysis of PG3-Oc.

Synthesis of Compound 4 (PG3-Oc):

Mass spectrum analysis was performed with Waters LC-MS system which includes a Waters single quadrupole 3100 MS (mass detector using electrospray and chemical ionization). $^1$H NMR analysis was performed on a Bruker Advance 300 MHz instrument (see, FIGS. 36, 37, and 38 MS and NMR spectrums).

Compound 3, (Z)-3-(5-((4'-methoxy-1H,5'H-[2,2'-bipyrrol]-5'-ylidene)methyl)-2,4-dimethyl-1H-pyrrol-3-yl)propanoic Acid 2,4-Dimethyl-1H-pyrrole-3-carboxylic acid 131.9 mg (compound 1, 0.79 mmol) and 4-methoxy-1H,1'H-2,2'-bipyrrole-5-carbaldehyde 100 mg (compound 2, 0.53 mmol) were dissolved in 10 mL ethanol, and then 90 µL concentrated hydrochloric acid was added to the mixture. The reaction was stirred at room temperature for 3 hours. The reaction mixture was concentrated. The crude material was chromatographed 63-200 µM aluminum oxide (activity II) eluting with ethyl acetate/hexane 30:70 to produce the desired compound 3, giving a correct molecular weight 339.91.

Compound 4 (PG3-Oc), Octyl (Z)-3-(5-((4'-methoxy-1H,5'H-[2,2'-bipyrrol]-5'-ylidene)methyl)-2,4-dimethyl-1H-pyrrol-3-yl)propanoate KI (18.7 mg), $Cs_2CO_3$ (169.3 mg) and compound 3 (75 mg) were added to 0.75 ml anhydrous DMF, stirred for 5 minutes at room temperature. Then 1-Bromooctane (39 µL) was added to the mixture, which was stirred at room temperature for 24 hours. 20 ml of PBS w/o $Ca^{2+}$—$Mg^{2+}$ buffer was added to the reaction mixture. The mixture was extracted with 20 mL×2 dichloromethane, and combined organic layer was washed with 50 ml of saturated NaCl. The organic layer was dried over anhydrous $Na_2SO_4$ overnight. The next day, the dried organic layer was concentrated and crude product was separated on aluminum oxide column. The desired compound 4 was eluted with ethyl acetate/hexane gradient from 10% to 20%. MS analysis gave the correct molecular weight [M+H$^+$] 452.23.

The present disclosure is not limited to the embodiments described and exemplified above, but is capable of variation and modification within the scope of the appended claims.

What is claimed is:
1. A compound of the formula:
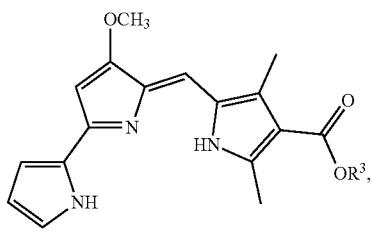
wherein R³ is hydrogen, benzyl, n-butyl, n-octyl, or 1-pentyne;
a compound of the formula:
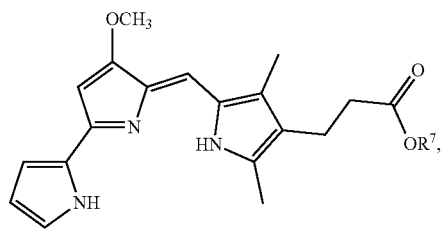
wherein R⁷ is hydrogen, ethyl, n-butyl, or n-octyl; or
a compound of the formula:
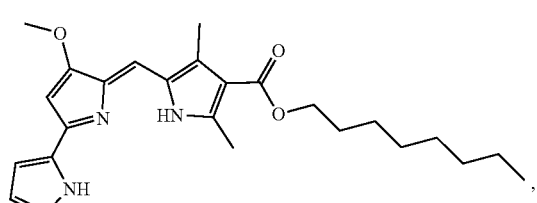
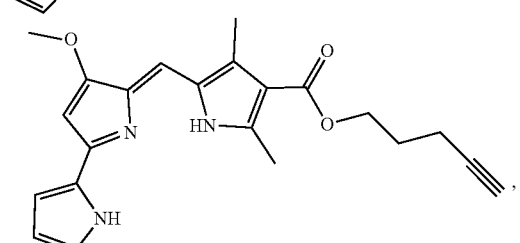
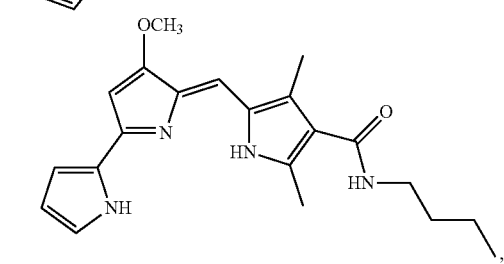
-continued
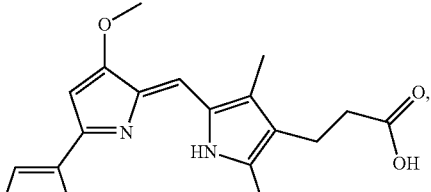
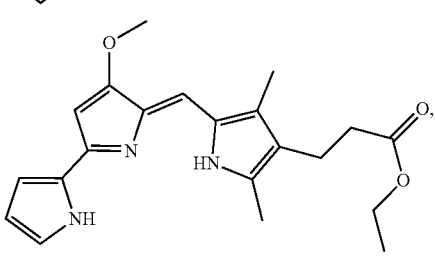
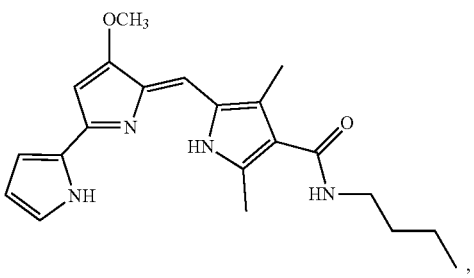
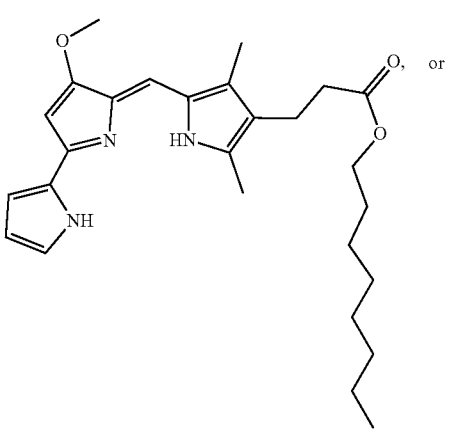

-continued

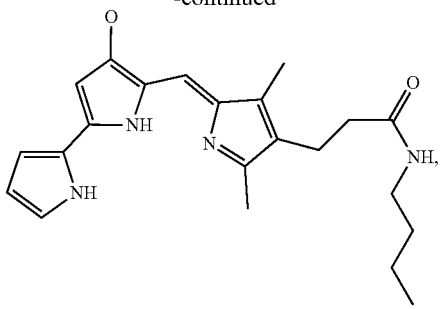

or a pharmaceutically acceptable salt thereof.

2. A composition comprising a compound of claim 1 and a carrier.

3. The composition of claim 2, wherein the carrier is a pharmaceutically acceptable carrier.

4. A method for treating cancer comprising administering to a patient an effective amount of a compound of claim 1, wherein the cancer patient is a prostate cancer patient and the cancer is prostate cancer, the cancer patient is a breast cancer patient and the cancer is breast cancer, the cancer patient is a kidney cancer patient and the cancer is kidney cancer, the cancer patient is an ovarian cancer patient and the cancer is ovarian cancer, the cancer patient is a glioblastoma patient and the cancer is glioblastoma, the cancer patient is a lymphoma patient and the cancer is lymphoma, or the cancer patient is a leukemia patient and the cancer is leukemia.

5. The method of 4, wherein the compound is in a composition including a pharmaceutically acceptable carrier.

6. The method of claim 4, wherein the compound is in a composition including a pharmaceutically acceptable excipient.

7. The composition of claim 2, wherein the composition is a liquid dosage form.

8. The composition of claim 2, wherein the composition is a solid dosage form.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: PUMA forward primer

<400> SEQUENCE: 1
gacgacctca acgcacagta                                                    20

<210> SEQ ID NO 2
<211> LENGTH: 22
<212> TYPE: DNA
<213> ORGANISM: Artificial Sequence
<220> FEATURE:
<223> OTHER INFORMATION: PUMA reverse primer

<400> SEQUENCE: 2
aggagtccca tgatgagatt gt                                                 22

<210> SEQ ID NO 3
<211> LENGTH: 21
<212> TYPE: DNA
<213> ORGANISM: Artificial Sequence
<220> FEATURE:
<223> OTHER INFORMATION: DR5 forward primer

<400> SEQUENCE: 3
acagttgcag ccgtagtctt g                                                  21

<210> SEQ ID NO 4
<211> LENGTH: 20
<212> TYPE: DNA
<213> ORGANISM: Artificial Sequence
<220> FEATURE:
<223> OTHER INFORMATION: DR5 reverse primer

<400> SEQUENCE: 4
ccaggtcgtt gtgagcttct                                                    20

<210> SEQ ID NO 5
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 5
tcgacagtca gccgcatctt cttt                                               24

<210> SEQ ID NO 6
<211> LENGTH: 24

```
<212> TYPE: DNA
<213> ORGANISM: Artificial Sequence
<220> FEATURE:
<223> OTHER INFORMATION: GAPDH reverse primer

<400> SEQUENCE: 6
accaaatccg ttgactccga cctt                                          24

<210> SEQ ID NO 7
<211> LENGTH: 24
<212> TYPE: DNA
<213> ORGANISM: Artificial Sequence
<220> FEATURE:
<223> OTHER INFORMATION: Guide1 forward primer

<400> SEQUENCE: 7
caccggcggg cggtcccacc cagg                                          24

<210> SEQ ID NO 8
<211> LENGTH: 24
<212> TYPE: DNA
<213> ORGANISM: Artificial Sequence
<220> FEATURE:
<223> OTHER INFORMATION: Guide1 reverse primer

<400> SEQUENCE: 8
aaaccctggg tgggaccgcc cgcc                                          24

<210> SEQ ID NO 9
<211> LENGTH: 24
<212> TYPE: DNA
<213> ORGANISM: Artificial Sequence
<220> FEATURE:
<223> OTHER INFORMATION: Guide 2 forward primer

<400> SEQUENCE: 9
caccgccgct cgtactgtgc gttg                                          24

<210> SEQ ID NO 10
<211> LENGTH: 24
<212> TYPE: DNA
<213> ORGANISM: Artificial Sequence
<220> FEATURE:
<223> OTHER INFORMATION: Guide 2 reverse primer

<400> SEQUENCE: 10
aaaccaacgc acagtacgag cggc                                          24

<210> SEQ ID NO 11
<211> LENGTH: 20
<212> TYPE: DNA
<213> ORGANISM: Artificial Sequence
<220> FEATURE:
<223> OTHER INFORMATION: PUMA exon 3 forward primer

<400> SEQUENCE: 11
cacagtctct ggccttctgg                                               20

<210> SEQ ID NO 12
<211> LENGTH: 17
<212> TYPE: DNA
<213> ORGANISM: Artificial Sequence
<220> FEATURE:
<223> OTHER INFORMATION: PUMA exon 3 reverse primer
```

```
<400> SEQUENCE: 12
agctgccgca catctgg                                              17
```